US010287277B2

United States Patent
Petersen

(10) Patent No.: US 10,287,277 B2
(45) Date of Patent: May 14, 2019

(54) FUMAGILLOL DERIVATIVES AND POLYMORPHS THEREOF

(71) Applicant: SynDevRx, Inc., Cambridge, MA (US)

(72) Inventor: John S. Petersen, Acton, MA (US)

(73) Assignee: SynDevRx, Inc., Cambridge, MA (US)

( * ) Notice: Subject to any disclaimer, the term of this patent is extended or adjusted under 35 U.S.C. 154(b) by 0 days.

(21) Appl. No.: 15/946,899

(22) Filed: Apr. 6, 2018

(65) Prior Publication Data

US 2018/0291010 A1  Oct. 11, 2018

Related U.S. Application Data

(63) Continuation of application No. 15/373,874, filed on Dec. 9, 2016, now Pat. No. 9,969,722.

(60) Provisional application No. 62/265,675, filed on Dec. 10, 2015.

(51) Int. Cl.
| | | |
|---|---|---|
| C07D 303/00 | (2006.01) |
| C07D 407/08 | (2006.01) |
| C07D 303/46 | (2006.01) |
| C07C 309/29 | (2006.01) |

(52) U.S. Cl.
CPC .......... *C07D 407/08* (2013.01); *C07C 309/29* (2013.01); *C07D 303/46* (2013.01); *C07B 2200/13* (2013.01)

(58) Field of Classification Search
CPC .. C07D 407/08; C07C 309/29; C07B 2200/13
USPC ........................................................ 549/546
See application file for complete search history.

(56) References Cited

U.S. PATENT DOCUMENTS

| | | |
|---|---|---|
| 4,997,878 A | 3/1991 | Bock et al. |
| 5,037,883 A | 8/1991 | Kopecek et al. |
| 5,037,957 A | 8/1991 | Grubb et al. |
| 5,166,172 A | 11/1992 | Kishimoto et al. |
| 5,258,453 A | 11/1993 | Kopecek et al. |
| 5,773,522 A | 6/1998 | Angelucci et al. |
| 6,063,812 A | 5/2000 | Hong et al. |

(Continued)

FOREIGN PATENT DOCUMENTS

| | | |
|---|---|---|
| CA | 1305053 | 7/1992 |
| EP | 0673258 | 5/2003 |

(Continued)

OTHER PUBLICATIONS

Arico-Muendel, C.C. et al., "Carbamate Analogues of Fumagillin as Potent, Targeted Inhibitors of Methionine Aminopeptidase-2", *J. Med. Chem.*, 52:8047-8056 (2009).

(Continued)

*Primary Examiner* — Taylor V Oh
(74) *Attorney, Agent, or Firm* — Cooley LLP; Ivor R. Elrifi; Matthew Pavao

(57) ABSTRACT

The present disclosure relates to salts and polymorphs of aminoalkylfumagillol carbamates (e.g., fumagill-6-yl N-(trans-4-aminocyclohexyl)carbamate benzenesulfonic acid salt and fumagill-6-yl N-(trans-4-aminocyclohexyl)carbamate hydroxynaphthoic acid salt). The polymorphs are characterized by X-ray powder diffraction, differential scanning calorimetry, and thermogravimetric analysis, among other methods. The polymorphs and salts can be used as intermediates in the production of fumagillol derivatives (e.g., polymer-conjugated fumagillol derivatives) as well as therapeutic agents for the treatment of various diseases and conditions such as cancer.

11 Claims, 27 Drawing Sheets

(56) References Cited

U.S. PATENT DOCUMENTS

| | | |
|---|---|---|
| 6,291,671 B1 | 9/2001 | Inoue et al. |
| 6,306,819 B1 | 10/2001 | Rubnick et al. |
| 6,436,912 B1 | 8/2002 | Inoue et al. |
| 6,464,850 B1 | 10/2002 | Zhang et al. |
| 6,548,477 B1 | 4/2003 | Olson et al. |
| 6,759,509 B1 | 7/2004 | King et al. |
| 6,803,438 B1 | 10/2004 | Brocchini et al. |
| 6,811,788 B2 | 11/2004 | Yu |
| 6,811,996 B1 | 11/2004 | Inoue et al. |
| 6,835,807 B1 | 12/2004 | Susaki et al. |
| 6,949,584 B2 | 9/2005 | Folkman et al. |
| 7,041,818 B2 | 5/2006 | Susaki et al. |
| 7,091,186 B2 | 8/2006 | Senter et al. |
| 7,223,837 B2 | 5/2007 | De Groot et al. |
| 7,332,523 B2 | 2/2008 | Folkman et al. |
| 7,553,816 B2 | 6/2009 | Senter et al. |
| 7,700,280 B2 | 4/2010 | Al-Murrani |
| 7,943,569 B2 | 5/2011 | Gemeinhart et al. |
| 8,349,891 B2 | 1/2013 | Crawford et al. |
| 8,367,721 B2 | 2/2013 | Hughes et al. |
| 8,399,512 B2 | 3/2013 | Akullian et al. |
| 9,173,956 B2 | 11/2015 | Petersen et al. |
| 9,320,805 B2 | 4/2016 | Petersen |
| 9,433,600 B2 | 9/2016 | Petersen et al. |
| 9,585,909 B2 | 3/2017 | Petersen |
| 9,730,955 B2 | 8/2017 | Petersen |
| 9,750,737 B2 | 9/2017 | Petersen et al. |
| 9,757,373 B2 | 9/2017 | Petersen et al. |
| 10,010,544 B2 | 7/2018 | Petersen et al. |
| 10,159,692 B2 | 12/2018 | Petersen et al. |
| 2002/0076442 A1 | 6/2002 | Burke et al. |
| 2004/0001801 A1 | 1/2004 | Madison et al. |
| 2004/0116348 A1 | 6/2004 | Chau et al. |
| 2004/0229945 A1 | 11/2004 | Satchi-Fainaro et al. |
| 2005/0036948 A1 | 2/2005 | Kasina et al. |
| 2006/0206948 A1 | 9/2006 | Zhao |
| 2006/0276512 A1 | 12/2006 | Han et al. |
| 2007/0142302 A1 | 6/2007 | Mitra et al. |
| 2007/0287680 A1 | 12/2007 | Cuchelkar et al. |
| 2008/0112919 A1 | 5/2008 | Satchi-Fainaro et al. |
| 2008/0248030 A1 | 10/2008 | Folkman et al. |
| 2009/0093014 A1 | 4/2009 | Burnet et al. |
| 2010/0111894 A1 | 5/2010 | Benny-Ratsaby et al. |
| 2011/0263561 A1 | 10/2011 | Heinrich et al. |
| 2011/0294952 A1 | 12/2011 | Petersen |
| 2013/0064832 A1 | 3/2013 | Aikawa et al. |
| 2013/0137831 A1 | 5/2013 | Petersen |
| 2013/0216494 A1 | 8/2013 | Petersen |
| 2014/0308235 A1 | 10/2014 | Petersen et al. |
| 2015/0141580 A1 | 5/2015 | Petersen et al. |
| 2015/0374657 A1 | 12/2015 | Petersen et al. |
| 2016/0184345 A1 | 6/2016 | Petersen |
| 2016/0256483 A1 | 9/2016 | Petersen |
| 2016/0346244 A1 | 12/2016 | Petersen et al. |
| 2017/0028014 A1 | 2/2017 | Petersen et al. |
| 2017/0196830 A1 | 7/2017 | Shanahan et al. |
| 2017/0258925 A1 | 9/2017 | Petersen |
| 2018/0271856 A1 | 9/2018 | Petersen |

FOREIGN PATENT DOCUMENTS

| | | |
|---|---|---|
| WO | WO 2003/086382 | 10/2003 |
| WO | WO 2004/110358 | 12/2004 |
| WO | WO 2008/011114 A2 | 1/2008 |
| WO | WO 2009/036108 | 3/2009 |
| WO | WO 2009/051706 | 4/2009 |
| WO | WO 2009/073445 | 6/2009 |
| WO | WO 2009/141826 | 11/2009 |
| WO | WO 2010/003475 | 1/2010 |
| WO | WO 2010/065877 | 6/2010 |
| WO | WO 2010/096603 | 8/2010 |
| WO | WO 2011/127304 | 10/2011 |
| WO | WO 2011/150022 | 12/2011 |
| WO | WO 2011/150088 | 12/2011 |
| WO | WO 2012/122264 | 9/2012 |
| WO | WO 2014/169026 A1 | 10/2014 |
| WO | WO 2017/123603 A1 | 7/2017 |

OTHER PUBLICATIONS

Bae et al., "Obesity and glycemic control in pateints with diabetes mellitus: Analysis of physician electronic health records in the US from 2009-2011" J. Diabetes and its Complications, (2016) v. 30, pp. 212-220.

Bernier, S.G. et al., "Fumagillin class inhibitors of methionine aminopeptidase-2", Drugs of the Future, 30(5):497-508 (2005).

Blencowe, C.A. et al., "Self-immolative linkers in polymeric delivery systems", Polym. Chem., 2:773-790 (2011).

Brakenhielm et al. "Angiogenesis Inhibitor, TNP-470, Prevents Diet-Induced and Genetic Obesity in Mice", Circulation Research, 2004, vol. 94, p. 1579-1588.

Chau, Y. et al., "Antitumor efficacy of a novel polymer-peptide-drug conjugate in human tumor xenograft models", Int. J. Cancer, 118:1519-1526 (2006).

D'Souza, A.J.M. et al., "Release from Polymeric Prodrugs: Linkages and Their Degradation", J. Pharm. Sci., 93(8):1962-1979 (2004).

Ducry, L. and Stump, B., "Antibody-Drug Conjugates: Linking Cytotoxic Payloads to Monoclonal Antibodies", Bioconj. Chem., 21:5-13 (2010).

Esposito et al. "The metabolic syndrome and inflammation: association or causation?" Nutr. Metab. Cardiovasc. Dis. 14(5):228-232 (2004).

Golub et al. "Molecular Classification of Cancer: Class Discovery and Class Prediction by Gene Expression Monitoring", Science, vol. 286, (1999) pp. 531-537.

Han, C.K. et al., "Design and synthesis of highly potent fumagillin analogues from homology modeling for a human MetAP-2", Biorg. Med. Chem. Lett., 10:39-43 (2000).

Herbst, R.S. et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", Journal of Clinical Oncology, 20(22):4440-4447 (2002).

Hughes, "ZGN-201, a Methionine-Aminopeptidase 2 Inhibitor, Durably Eliminates Body Fat in Obese Mice Through Regulation of Fat Metabolism and Food Intake" American Diabetes Association, (2010).

Jeong, B-S. et al., "Total synthesis and antiangiogenic activity of cyclopentane analogues of fumagillol", Bioorganic and Medicinal Chemistry Letters, 15:3580-3583 (2005).

Joharapurkar, "Inhibition of the methionine aminopeptidase 2 enzyme for the treatment of obesity" Diabetes, Metabolic Syndrome and Obesity v.7, p. 73 (2014).

Kahn et al. "Mechanisms linking obesity to insulin resistance and type 2 diabetes." Nature, vol. 444, 2006, p. 840-846.

Kim et al, "5-Demethoxyfumagillol, a Potent Angiogenesis Inhibitor Isolated from Aspergillus fumigatus", Chem. Pharm. Bull., 52(4): 447-450 (2004).

Kim et al. "Assessment of the anti-obesity effects of the TNP-470 analog, CKD-732", Journal of Molecular Endocrinology, 2007, vol. 38, p. 455-465.

Klok et al., "The role of leptin and ghrelin in the regulation of food intake and body weight in humans: a review", Obesity Reviews (2007) vol. 8, pp. 21-34.

Law and Tung, "Proteolysis: A Biological Process Adapted in Drug Delivery, Therapy, and Imaging", Bioconjugate Chem., 20:1683-1695 (2009).

Lee, H.W. et al., "Design, Synthesis, and Antiangiogenic Effects of a Series of Potent Novel Fumagillin Analogues", Chem. Pharm. Bull., 55(7):1024-1029 (2007).

Lijnen et al. "Fumagillin Reduces Adipose Tissue Formation in Murine Models of Nutritionally Induced Obesity", Obesity, 2010, vol. 18, No. 12, p. 2241-2246.

(56) References Cited

OTHER PUBLICATIONS

Mann-Steinberg and Satchi-Fainaro, "TNP-470: The Resurrection of the First Synthetic Angiogenesis Inhibitor", *Folkman and Figg, Angiogenesis: An Integrative Approach from Science to Medicine*, 35:395-414 (2008).
Mason, "Proteolytic networks in Cancer" *Trends in Cell Biology*, v.21 p. 228 (2011).
Satchi-Fainaro, R. et al. "Targeting angiogenesis with a conjugate of HPMA copolymer and TNP-470", *Nature Med.*, 10(3): 255-261 (2004).
Segal, E. et al., "Design and development of polymer conjugates as anti-angiogenic agents", *Adv. Drug. Deliv. Reviews*, 61(13):1159-1176 (2009).
Shiose, Y. et al., "Relationship between Drug Release of DE-310, Macromolecular Prodrug of DX-8951f, and Cathepsins Activity in Several Tumors", *Biol. Pharm. Bull.*, 30(12):2365-2370 (2007).
Shiose, Y. et al., "Systematic Research of Peptide Spacers Controlling Drug Release from Macromolecular Prodrug System, Carboxymethyldextran Polyalcohol—Peptide—Drug Conjugates", *Bioconjugate Chem.*, 20(1):60-70 (2009).
Subr, V. et al., "Poly[M-)2-hydroxypropyl)methacrylamide] Conjugates of Methotrexate Synthesis and in vitro Drug Release", *J Controlled Release*, 49:123-132 (1997).
Sutherland, J. et al. "The Metabolic Syndrome and Inflammation" *Metabolic Syndrome and Related Disorders* 2(2):82-104 (2004).

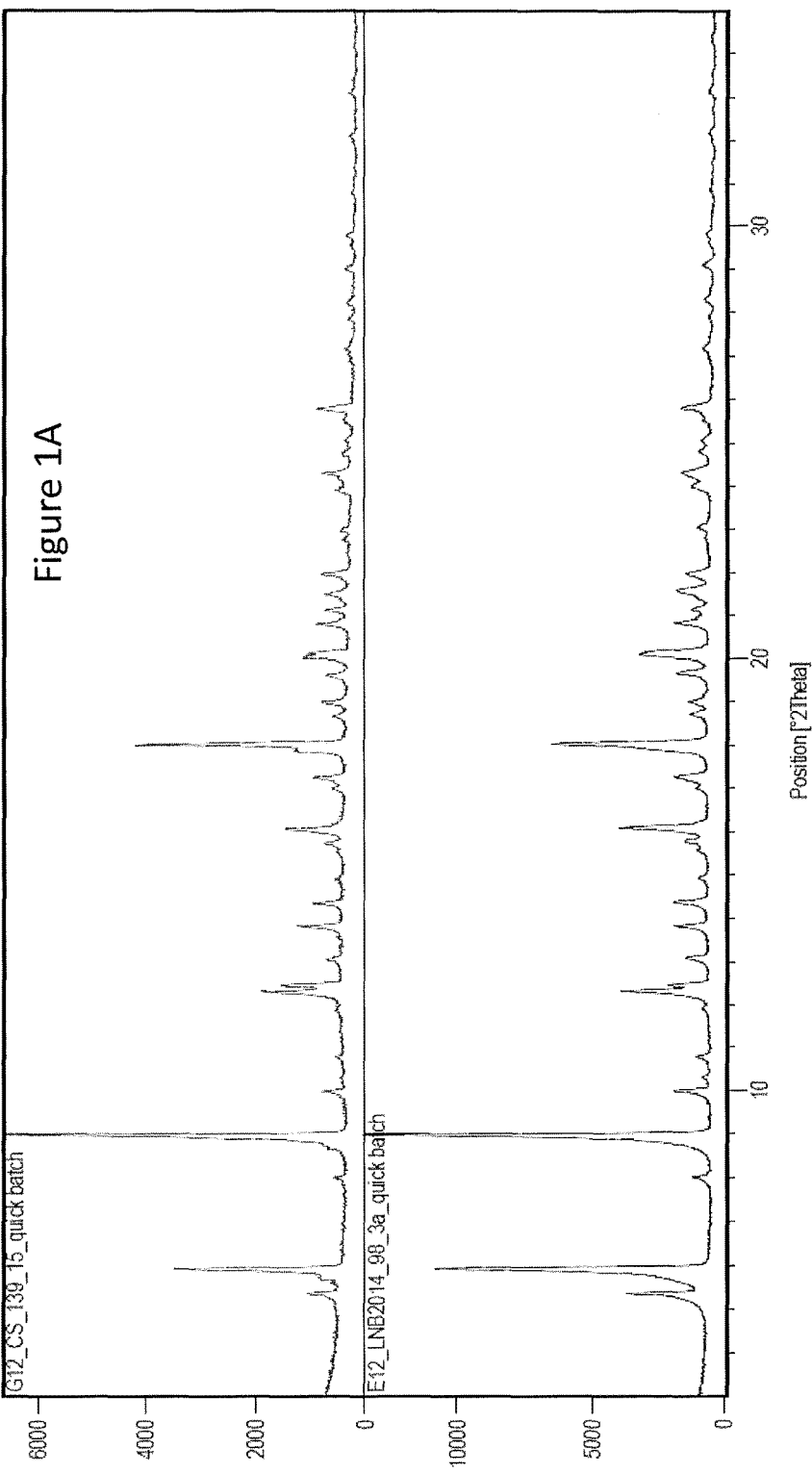

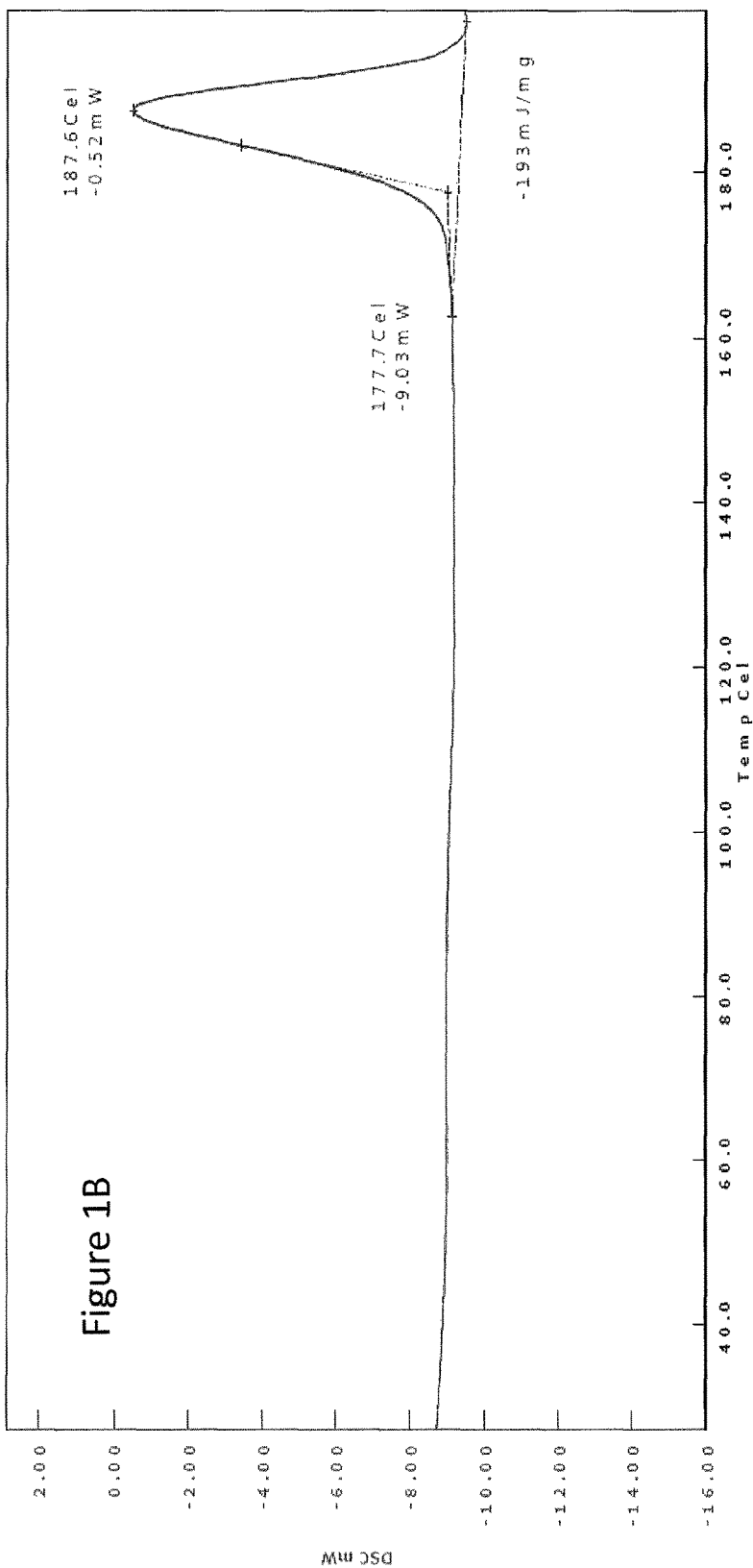

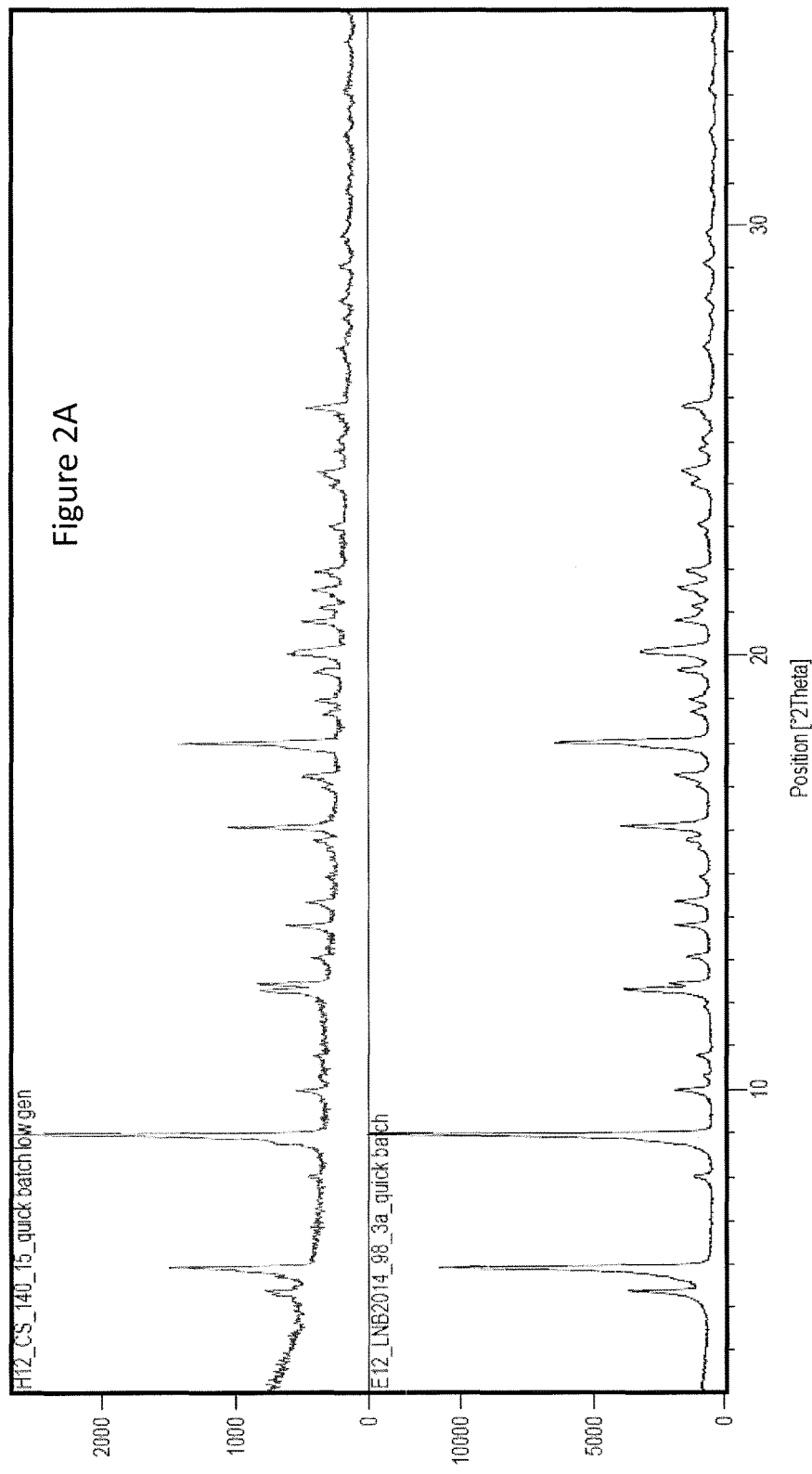

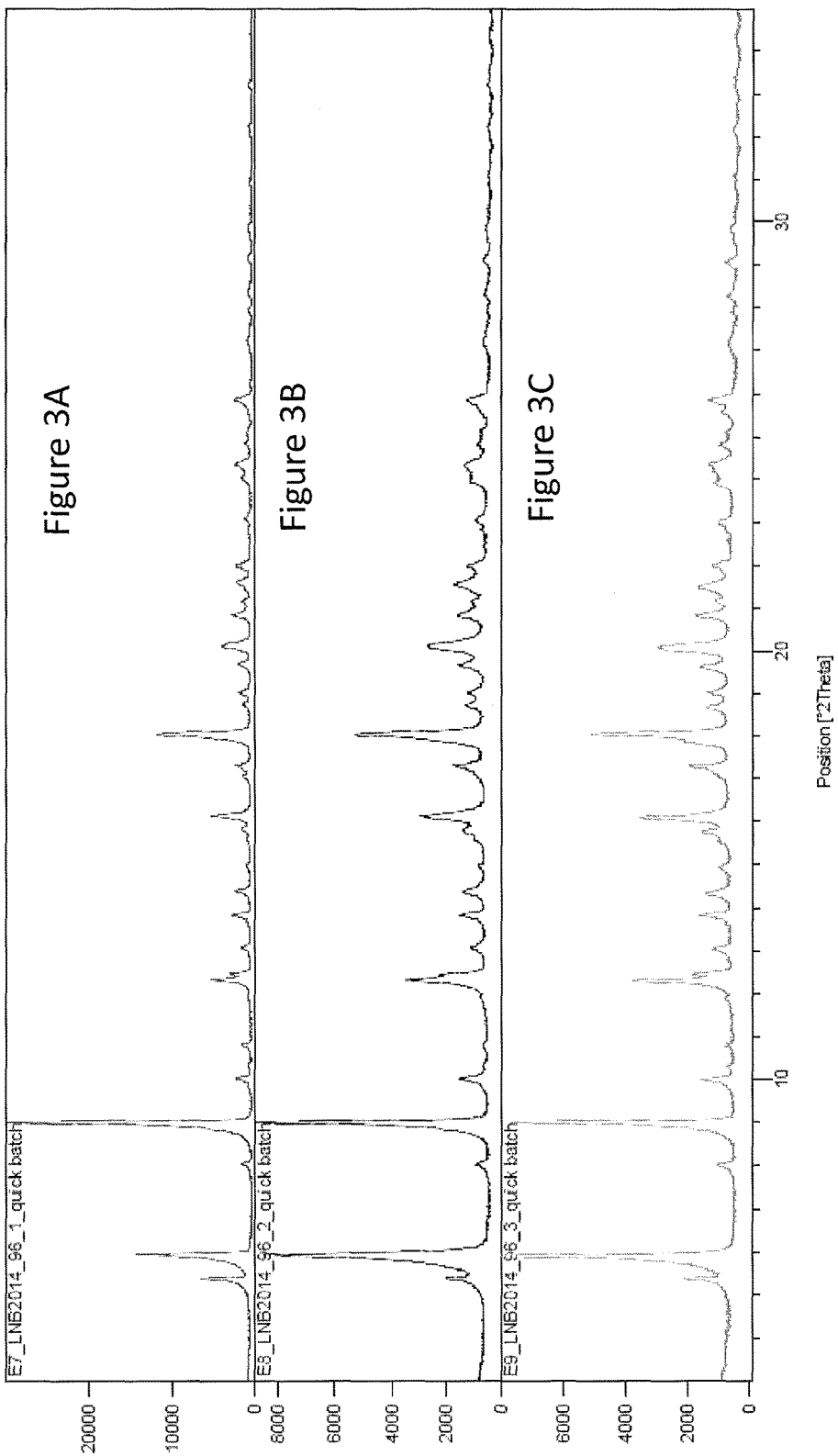

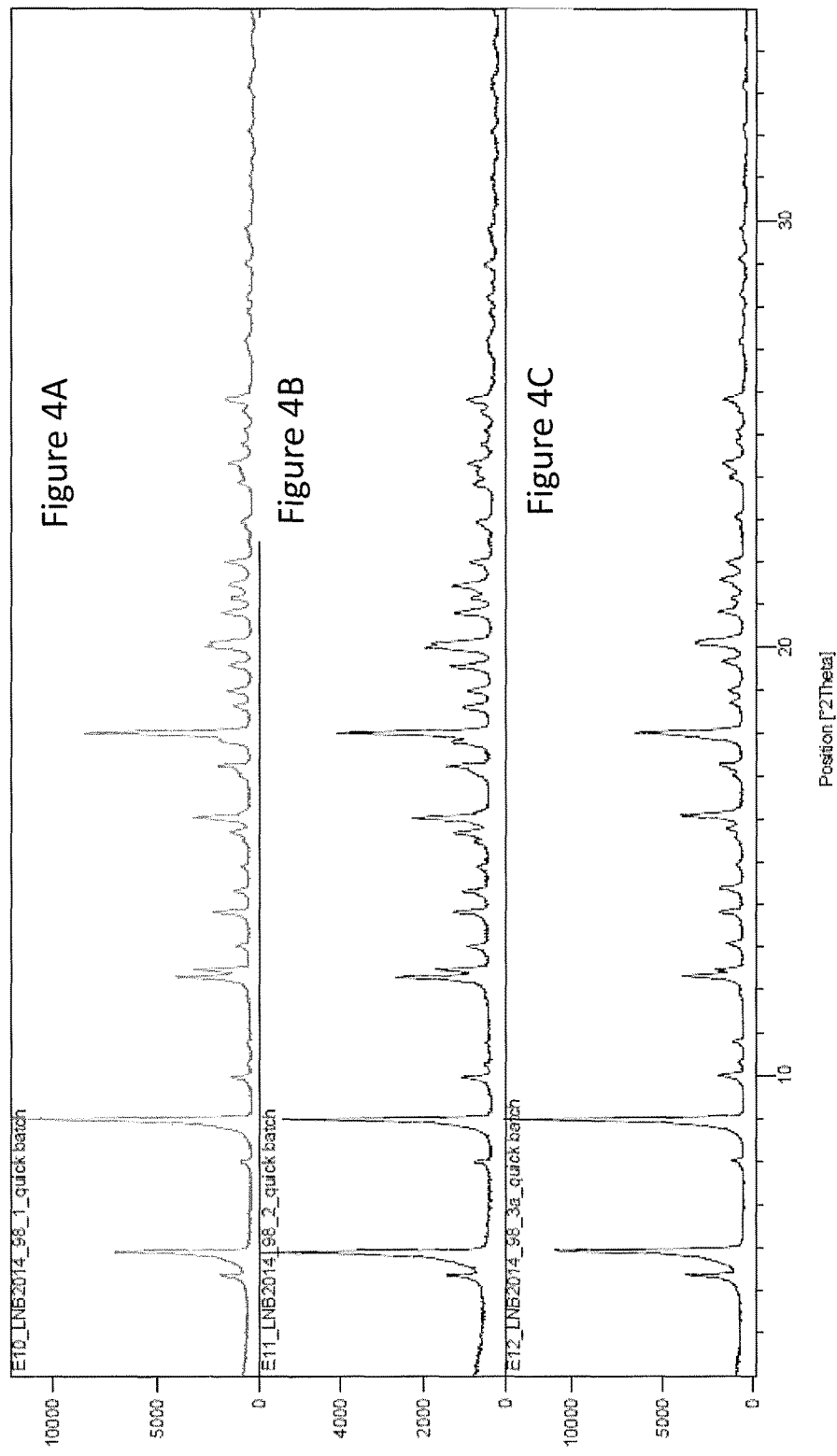

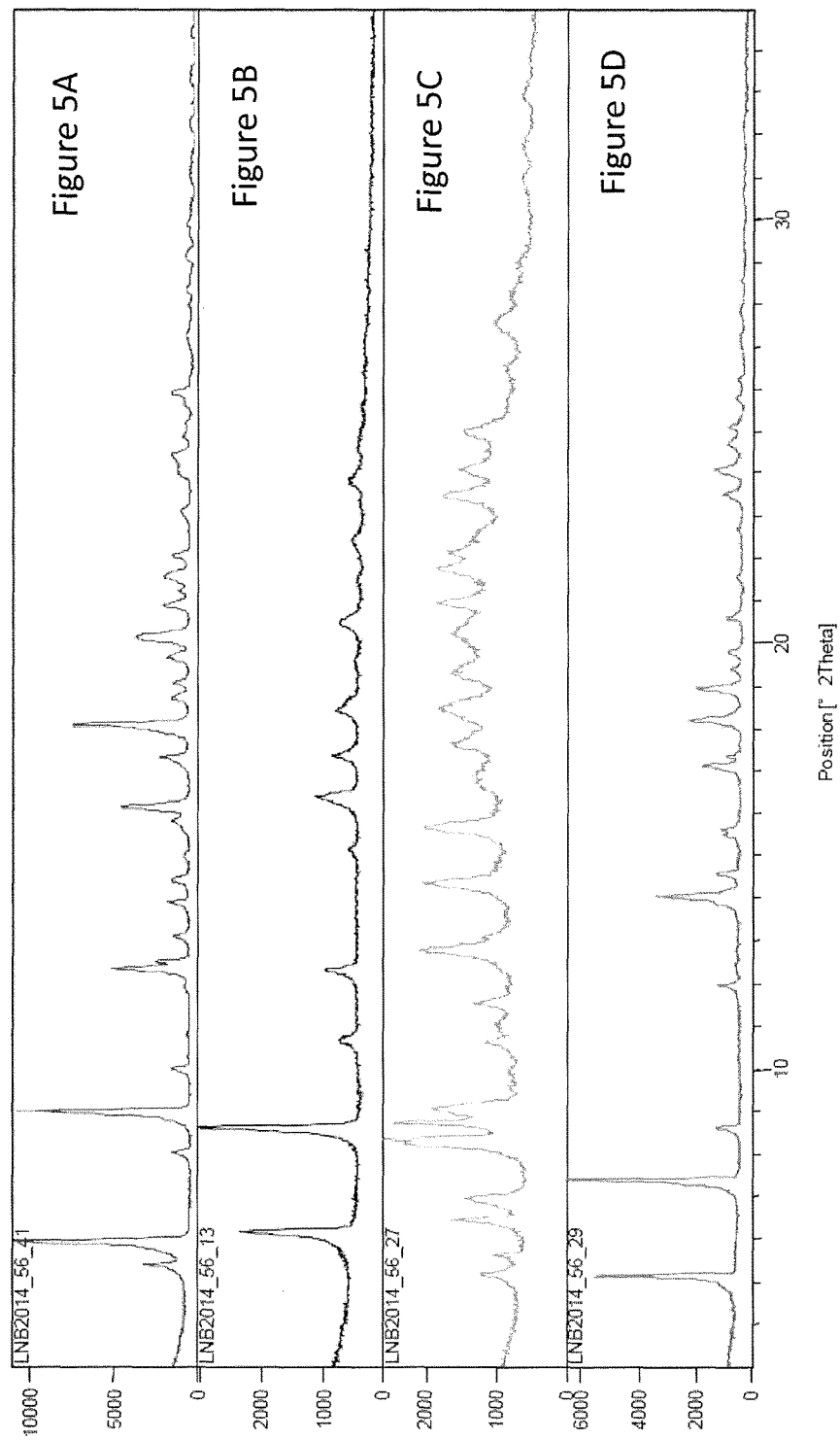

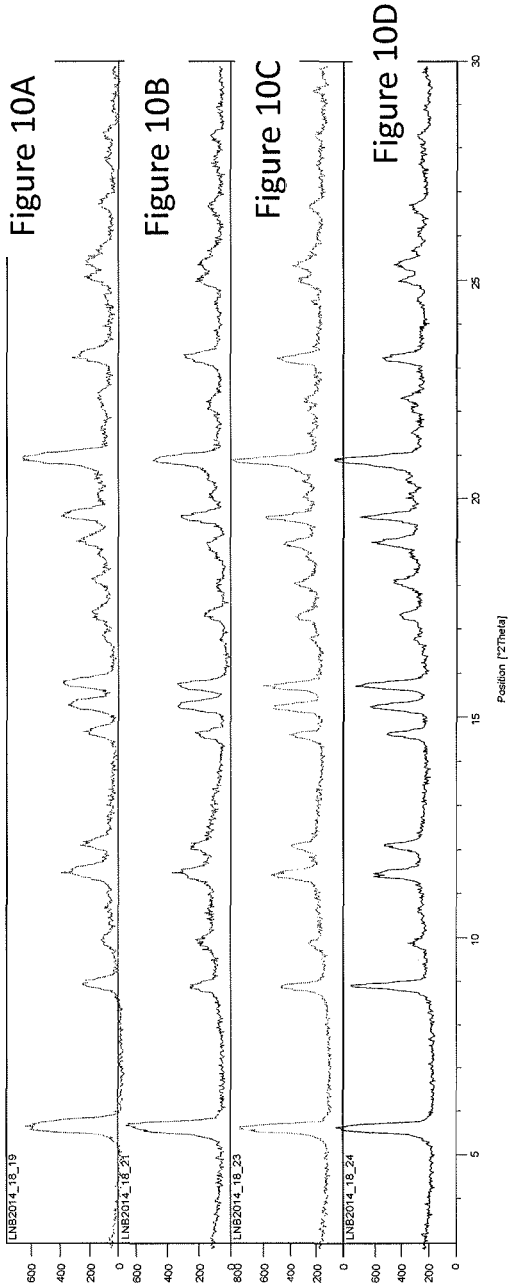

FUMAGILLOL DERIVATIVES AND POLYMORPHS THEREOF

CROSS REFERENCE TO RELATED APPLICATIONS

This application is a continuation of U.S. application Ser. No. 15/373,874, filed Dec. 9, 2016 and now allowed, which claims the benefit of priority to U.S. Provisional Patent Application Ser. No. 62/265,675, filed Dec. 10, 2015. The contents of these applications are hereby incorporated by reference in their entirety.

FIELD OF THE DISCLOSURE

The present application relates to salts and polymorphs of aminoalkylfumagillol carbamates (e.g., fumagill-6-yl N-(trans-4-aminocyclohexyl)carbamate benzenesulfonic acid salt and fumagill-6-yl N-(trans-4-aminocyclohexyl)carbamate hydroxynaphthoic acid salt). The salts and polymorphs of the present application are useful as stable intermediates in the production of fumagillol derivatives (e.g., polymer-conjugated fumagillol derivatives), or as therapeutic agents.

BACKGROUND

Fumagillin is a small molecule which has been used as an antimicrobial and antiprotozoal agent. Fumagillin's clinical application and those of fumagillol derivatives have been limited by toxicity. Formation of fumagillin-conjugated polymers for therapy requires the existence of one or more stable, pure, fumagillin derived intermediates that do not readily self-condense or hydrolyze (e.g., by reaction of an amine-modified fumagillol with an epoxide on fumagillol). Moreover, impurities covalently bonded to a polymer backbone can be difficult to remove.

SUMMARY

The present disclosure is directed to pure, stable derivatives of fumagillol (e.g., Formula I and Formula II). The derivatives can be used as synthetic intermediates to produce polymer-bound fumagillol conjugates. Alternatively, the derivatives can be used directly as therapeutic agents.

The present application is directed to salts of aminoalkylfumagillol carbamates, such as fumagill-6-yl N-(trans-4-aminocyclohexyl)carbamate benzenesulfonic acid salt, also known as (1R,4r)-4-(((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)amino)cyclohexan-1-aminium benzenesulfonate, and fumagill-6-yl N-(trans-4-aminocyclohexyl)carbamate hydroxynaphthoic acid salt, also known as (1R,4r)-4-(((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)amino)cyclohexan-1-aminium 1-hydroxy-2-naphthoate. The present disclosure also provides for stable, pure, crystalline polymorphs of both of these salts. The salts and polymorphs provided herein are stable and can be used as intermediates in the production of fumagillol derivatives (e.g., polymer-conjugated fumagillol derivatives). These derivatives are in turn useful as therapeutic agents in the treatment of a number of diseases. Additionally, the salts and polymorphs can be used directly as therapeutic agents.

In one aspect, the present disclosure describes fumagill-6-yl N-(trans-4-aminocyclohexyl)carbamate benzenesulfonic acid salt (Formula I):

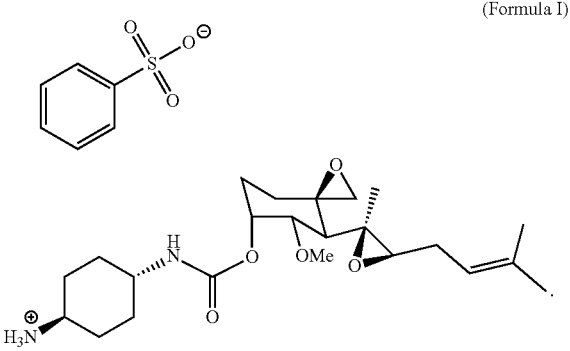

(Formula I)

In one aspect, the present disclosure provides polymorphs of fumagill-6-yl N-(trans-4-aminocyclohexyl)carbamate benzenesulfonic acid salt (Formula I) (e.g., Form I, Form II, Form III, and Form IV).

In one aspect, the present disclosure provides a polymorph (Form II) of fumagill-6-yl N-(trans-4-aminocyclohexyl)carbamate benzenesulfonic acid salt that is characterized by an X-ray powder diffraction pattern including peaks at about 6.0, 9.0, and 18.0° 2θ using Cu Kα radiation. In one or more embodiments, the Form II polymorph is characterized by an exothermic event onset at about 178° C. and a peak at about 188° C., as measured by differential scanning calorimetry. In one or more embodiments, the Form II polymorph is characterized by an exothermic onset at about 181° C. and a peak at about 189° C., as measured by thermogravimetric analysis/differential thermal analysis (TG/DTA). In one or more embodiments, Form II is characterized by an X-ray diffraction pattern substantially similar to that set forth in FIG. 5A or 6A.

In one aspect, the present disclosure provides a polymorph (Form I) of fumagill-6-yl N-(trans-4-aminocyclohexyl)carbamate benzenesulfonic acid salt that is characterized by an X-ray powder diffraction pattern including peaks at about 6.1, 8.6, and 16.4° 2θ using Cu Kα radiation. In some embodiments, Form I is characterized by an X-ray diffraction pattern substantially similar to that set forth in FIG. 5B or FIG. 6B.

In one aspect, the present disclosure provides a polymorph (Form III) of fumagill-6-yl N-(trans-4-aminocyclohexyl)carbamate benzenesulfonic acid salt that is characterized by an X-ray powder diffraction pattern including peaks at about 8.3, 12.8 and 15.7° 2θ using Cu Kα radiation. In some embodiments, Form III is characterized by an X-ray diffraction pattern substantially similar to that set forth in FIG. 5C or FIG. 6C.

In one aspect, the present disclosure provides a polymorph (Form IV) of fumagill-6-yl N-(trans-4-aminocyclohexyl)carbamate benzenesulfonic acid salt that is characterized by an X-ray powder diffraction pattern including peaks at about 5.1, 7.3 and 14.0° 2θ using Cu Kα radiation. In some embodiments, Form IV is characterized by an X-ray diffraction pattern substantially similar to that set forth in FIG. 5D or FIG. 6D.

In another aspect, the present disclosure describes fumagill-6-yl N-(trans-4-aminocyclohexyl)carbamate hydroxynaphthoic acid salt (Formula II):

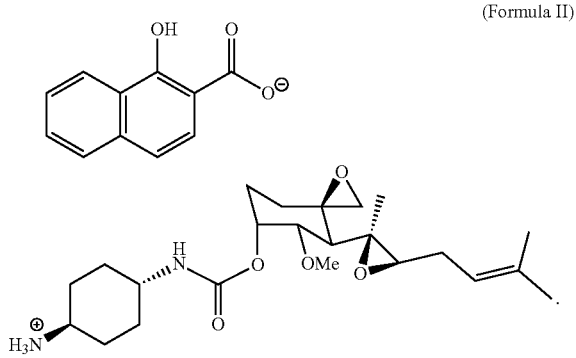

(Formula II)

In another aspect, the present disclosure describes polymorphs of fumagill-6-yl N-(trans-4-aminocyclohexyl)carbamate hydroxynaphthoic acid salt (Formula II) (e.g., Form A).

In one aspect, the present disclosure provides a polymorph (Form A) of fumagill-6-yl N-(trans-4-aminocyclohexyl)carbamate hydroxynaphthoic acid salt characterized by an X-ray powder diffraction pattern at about 5.6, 8.9, and 15.4 degrees 2θ using Cu Kα radiation. In one or more embodiments, Form A is characterized by an endothermic onset at about 182° C. and a peak at about 186° C. as measured by differential scanning calorimetry. In some embodiments, Form A is characterized by an endothermic onset at about 181° C. with a peak at about 186° C. and an exotherm at about 191° C. (peak) as measured by thermogravimetric analysis/differential thermal analysis (TG/DTA).

In another aspect, the present disclosure provides a method for preparing a polymorph of fumagill-6-yl N-(trans-4-aminocyclohexyl)carbamate benzenesulfonic acid salt (Formula I) comprising:
(i) Step 1: dissolving fumagill-6-yl N-(trans-4-aminocyclohexyl)carbamate benzenesulfonic acid salt in methanol, optionally containing MTBE, to form a solution;
(ii) Step 2: optionally adding a seed crystal (e.g., about 1 weight percent) of fumagill-6-yl N-(trans-4-aminocyclohexyl)carbamate benzenesulfonic acid salt to the solution;
(iii) Step 3: optionally separating the crystallized fumagill-6-yl N-(trans-4-aminocyclohexyl)carbamate benzenesulfonic acid salt from the solution.

In some embodiments, the method further comprises the optional Steps 1A and/or 1B after Step 1 but before Step 2:
Step 1A: cooling the solution of fumagill-6-yl N-(trans-4-aminocyclohexyl)carbamate benzenesulfonic acid salt from the previous step;
Step 1B: adding additional MTBE to the solution of fumagill-6-yl N-(trans-4-aminocyclohexyl)carbamate benzenesulfonic acid salt from the previous step.

In some embodiments, the method further comprises the optional Steps 2A and/or 2B after Step 2 but before optional Step 3:
Step 2A: cooling the solution of fumagill-6-yl N-(trans-4-aminocyclohexyl)carbamate benzenesulfonic acid salt from the previous step;
Step 2B: adding MTBE to the solution of fumagill-6-yl N-(trans-4-aminocyclohexyl)carbamate benzenesulfonic acid salt from the previous step.

In one or more embodiments, the method comprises Step 1, Step 2, and Step 3. In some embodiments, the method comprises Step 1, Step 1A, Step 2, and Step 3. In some embodiments, the method comprises Step 1, Step 1B, Step 2, and Step 3. In some embodiments, the method comprises Step 1, Step 2, Step 2A, and Step 3. In some embodiments, the method comprises Step 1, Step 2, Step 2B, and Step 3. In some embodiments, the method comprises Step 1, Step 1A, Step 2, Step 2A, and Step 3. In some embodiments, the method comprises Step 1, Step 1A, Step 2, Step 2B, and Step 3. In some embodiments, the method comprises Step 1, Step 1B, Step 2, Step 2A, and Step 3. In some embodiments, the method comprises Step 1, Step 1B, Step 2, Step 2B, and Step 3. In some embodiments, the method comprises Step 1, Step 1A, Step 1B, Step 2, and Step 3. In some embodiments, the method comprises Step 1, Step 1B, Step 1A, Step 2, and Step 3. In some embodiments, the method comprises Step 1, Step 1A, Step 1B, Step 2, Step 2A, and Step 3. In some embodiments, the method comprises Step 1, Step 1A, Step 1B, Step 2, Step 2B, and Step 3. In some embodiments, the method comprises Step 1, Step 1B, Step 1A, Step 2, Step 2A, and Step 3. In some embodiments, the method comprises Step 1, Step 1B, Step 1A, Step 2, Step 2B, and Step 3. In some embodiments, the method comprises Step 1, Step 2, Step 2A, Step 2B, and Step 3. In some embodiments, the method comprises Step 1, Step 2, Step 2B, Step 2A, and Step 3. In some embodiments, the method comprises Step 1, Step 1A, Step 2, Step 2A, Step 2B, and Step 3. In some embodiments, the method comprises Step 1, Step 1A, Step 2, Step 2B, Step 2A, and Step 3. In some embodiments, the method comprises Step 1, Step 1B, Step 2, Step 2A, Step 2B, and Step 3. In some embodiments, the method comprises Step 1, Step 1B, Step 2, Step 2B, Step 2A, and Step 3. In some embodiments, the method comprises Step 1, Step 1A, Step 1B, Step 2, Step 2A, Step 2B, and Step 3. In some embodiments, the method comprises Step 1, Step 1A, Step 1B, Step 2, Step 2B, Step 2A, and Step 3. In some embodiments, the method comprises Step 1, Step 1B, Step 1A, Step 2, Step 2A, Step 2B, and Step 3. In some embodiments, the method comprises Step 1, Step 1B, Step 1A, Step 2, Step 2B, Step 2A, and Step 3.

In one or more embodiments, the present disclosure provides a process for the reactive crystallization of a polymorph of fumagill-6-yl N-(trans-4-aminocyclohexyl)carbamate benzenesulfonic acid salt, comprising:
(i) Step 1': adding benzenesulfonic acid (e.g., a solution of benzenesulfonic acid in tert-butyl methyl ether or ethyl acetate) to a solution of fumagill-6-yl N-(trans-4-aminocyclohexyl)carbamate in a solvent (e.g., tert-butyl methyl ether, methanol, a combination of tert-butyl methyl ether and methanol, or ethyl acetate). The addition can form a precipitate which is then isolated (e.g., by filtration). The precipitate comprising fumagill-6-yl N-(trans-4-aminocyclohexyl)carbamate benzenesulfonic acid can then be re-dissolved in a solvent as in Step 1 for further recrystallization, above.

In some embodiments, the process further comprises one or more steps selected from Step 1A, Step 1B, Step 2, Step 2A, Step 2B, and Step 3, as described above.

In some embodiments, the process comprises Step 1', Step 1A, and Step 3. In some embodiments, the process comprises Step 1', Step 1A, Step 2, and Step 3. In some embodiments, the process comprises Step 1', Step 2, Step 2A, and Step 3. In some embodiments, the process comprises Step 1', Step 1B, Step 2, and Step 3. In some embodiments, the process comprises Step 1', Step 2, Step 2B, and Step 3.

In one or more embodiments, the method comprises Step 1', Step 2, and Step 3. In some embodiments, the method comprises Step 1', Step 1A, Step 2, and Step 3. In some embodiments, the method comprises Step 1', Step 1B, Step 2, and Step 3. In some embodiments, the method comprises Step 1', Step 2, Step 2A, and Step 3. In some embodiments, the method comprises Step 1', Step 2, Step 2B, and Step 3. In some embodiments, the method comprises Step 1', Step 1A, Step 2, Step 2A, and Step 3. In some embodiments, the method comprises Step 1', Step 1A, Step 2, Step 2B, and Step 3. In some embodiments, the method comprises Step 1', Step 1B, Step 2, Step 2A, and Step 3. In some embodiments, the method comprises Step 1', Step 1B, Step 2, Step 2B, and Step 3. In some embodiments, the method comprises Step 1', Step 1A, Step 1B, Step 2, and Step 3. In some embodiments, the method comprises Step 1', Step 1B, Step 1A, Step 2, and Step 3. In some embodiments, the method comprises Step 1', Step 1A, Step 1B, Step 2, Step 2A, and Step 3. In some embodiments, the method comprises Step 1', Step 1A, Step 1B, Step 2, Step 2B, and Step 3. In some embodiments, the method comprises Step 1', Step 1B, Step 1A, Step 2, Step 2A, and Step 3. In some embodiments, the method comprises Step 1', Step 1B, Step 1A, Step 2, Step 2B, and Step 3. In some embodiments, the method comprises Step 1', Step 2, Step 2A, Step 2B, and Step 3. In some embodiments, the method comprises Step 1', Step 2, Step 2B, Step 2A, and Step 3. In some embodiments, the method comprises Step 1', Step 1A, Step 2, Step 2A, Step 2B, and Step 3. In some embodiments, the method comprises Step 1', Step 1A, Step 2, Step 2B, Step 2A, and Step 3. In some embodiments, the method comprises Step 1', Step 1B, Step 2, Step 2A, Step 2B, and Step 3. In some embodiments, the method comprises Step 1', Step 1B, Step 2, Step 2B, Step 2A, and Step 3. In some embodiments, the method comprises Step 1', Step 1A, Step 1B, Step 2, Step 2A, Step 2B, and Step 3. In some embodiments, the method comprises Step 1', Step 1A, Step 1B, Step 2, Step 2B, Step 2A, and Step 3. In some embodiments, the method comprises Step 1', Step 1B, Step 1A, Step 2, Step 2A, Step 2B, and Step 3. In some embodiments, the method comprises Step 1', Step 1B, Step 1A, Step 2, Step 2B, Step 2A, and Step 3.

In one or more embodiments, the benzenesulfonic acid is added as a solution in an appropriate solvent (e.g., MTBE, methanol or a combination thereof) to the solution of solution of fumagill-6-yl N-(trans-4-aminocyclohexyl)carbamate.

In one or more embodiments, addition of any one or a combination of Steps 1A, 1B, 2A and 2B can result in increased yield and/or improved purity of the resulting polymorph.

In one aspect, the present disclosure provides a process for making a compound of Formula III:

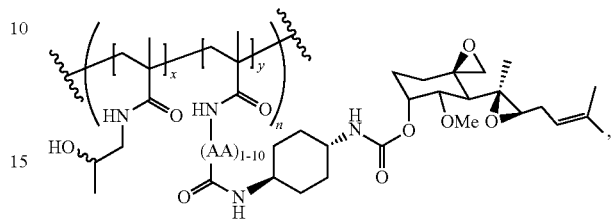

(Formula III)

wherein AA is a naturally occurring or unnatural amino acid, x is an integer in the range of 1 to about 450, y is an integer in the range of 1 to about 30, and n is an integer in the range of 1 to about 50. For instance, a compound of Formula III can be Compound 1:

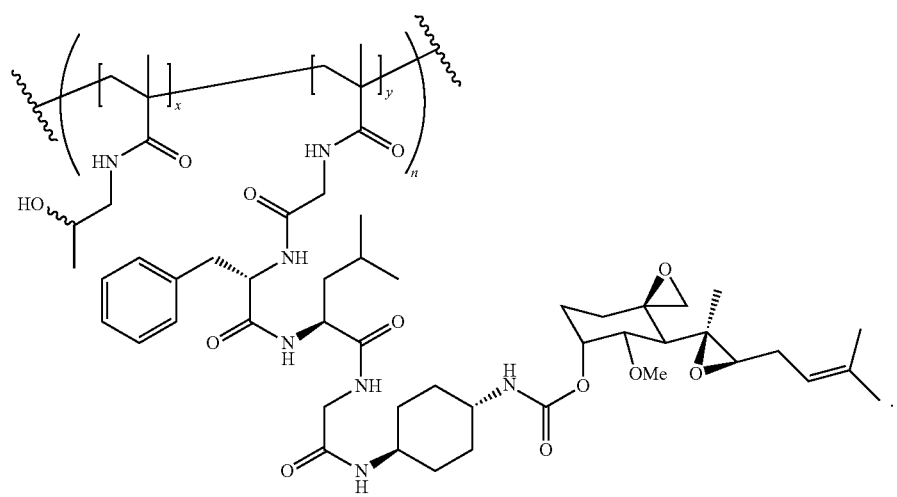

(Compound 1)

In some embodiments, the method comprises contacting a compound of Formula I or Formula II:

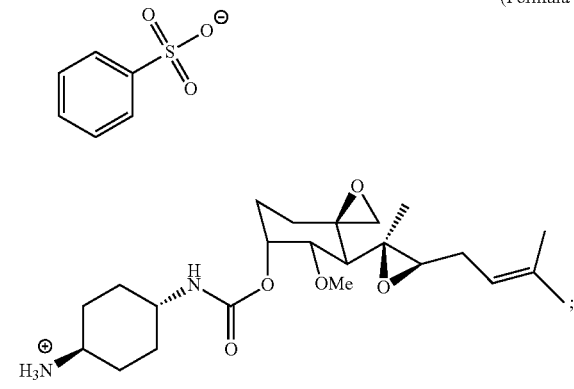

(Formula I)

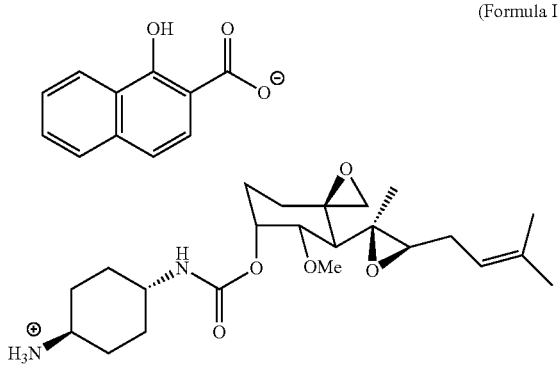

(Formula II)

with a compound of Formula IV:

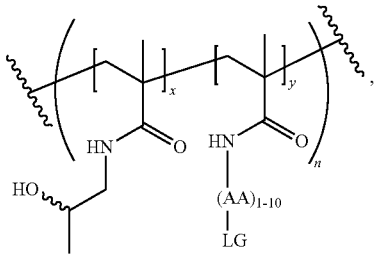

(Formula IV)

wherein x, y, and n, are each as defined as above, and LG is a leaving group (e.g., para-nitrophenyl).

In another aspect, the present disclosure provides crystallization of a compound of Formula I or Formula II from ethyl acetate.

In another aspect, the present disclosure provides the use of a compound of Formula I or Formula II for the treatment of a disease.

In one or more embodiments, the present disclosure provides a composition comprising a highly pure compound of Formula I or Formula II.

In one or more embodiments, the present disclosure provides a composition comprising a polymorph of Formula I and a pharmaceutically acceptable carrier. In one or more embodiments, the present disclosure provides a composition comprising the Form II polymorph of Formula I and a pharmaceutically acceptable carrier.

In one or more embodiments, the present disclosure provides a composition comprising a polymorph of Formula II and a pharmaceutically acceptable carrier. In one or more embodiments, the present disclosure provides a composition comprising the Form A polymorph of Formula II and a pharmaceutically acceptable carrier.

The polymorphs of fumagill-6-yl N-(trans-4-aminocyclohexyl)carbamate benzenesulfonic acid salt and fumagill-6-yl N-(trans-4-aminocyclohexyl)carbamate hydroxynaphthoic acid salt provided herein are more stable than the corresponding free base, fumagill-6-yl N-(trans-4-aminocyclohexyl)carbamate, and can be isolated in higher purity than the free base. Moreover, the polymorphs (e.g., Form II) are more stable than certain other acids salts of fumagill-6-yl N-(trans-4-aminocyclohexyl)carbamate, including the hemi-tartrate salt. Because of their increased purity and improved stability, the salts and polymorphs provided herein can be used as intermediates in the synthesis of polymer-conjugated fumagillol derivatives. The polymer conjugates can then be used as therapeutic agents for the treatment of diseases such as diseases related to MetAP2. Additionally, the salts and polymorphs can be used as therapeutic agents.

In another aspect, the present disclosure provides for the use of a compound of Formula I or Formula II or a polymorph thereof to inhibit or decrease the activity of MetAP2. In one or more embodiments, the activity of MetAP2 inhibitor can influence the initiation and development a disease, such as cancer.

In one aspect, the present disclosure provides a method of treatment of a disease, comprising administering to a subject in need thereof an effective amount of a compound of Formula I, Formula II, or Formula III.

In one aspect, the present disclosure provides the use of a compound of Formula I, Formula II, or Formula III in the manufacture of a medicament for the treatment of a disease.

In another aspect, the present disclosure provides a compound of Formula I, Formula II, or Formula III for the treatment of a disease.

The disease can be, for instance, cancer or a metabolic disease.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and are not intended to be limiting. Additional features and advantages of the technology disclosed herein will become apparent to one of skill in the art upon reading the Detailed Description, below.

BRIEF DESCRIPTION OF THE DRAWINGS

FIG. 1A shows the XRPD spectrum of a sample of the Form II polymorph of Formula I (benzenesulfonic acid salt of fumagill-6-yl N-(trans-4-aminocyclohexyl)carbamate) (top) together with a reference spectrum (bottom).

FIG. 1B shows a DSC curve of a sample of the Form II polymorph of Formula I.

FIG. 2A shows the XRPD spectrum of a sample of the Form II polymorph of Formula I (top) together with the same reference spectrum as FIG. 1A (bottom).

FIG. 3A shows an XRPD spectrum of a first sample of the Form II polymorph of Formula I prepared by a cooling method described herein as Cooling-1.

FIG. 3B shows an XRPD spectrum of a second sample of the Form II polymorph of Formula I prepared by a cooling method described herein as Cooling-1.

FIG. 3C shows an XRPD spectrum of a third sample of the Form II polymorph of Formula I prepared by a cooling method described herein as Cooling-1.

FIG. 4A shows an XRPD spectrum of a first sample of the Form II polymorph of Formula I prepared by an antisolvent method described herein Antisol-1.

FIG. 4B shows an XRPD spectrum of a second sample of the Form II polymorph of Formula I prepared by an antisolvent method described herein Antisol-1.

FIG. 4C shows an XRPD spectrum of a third sample of the Form II polymorph of Formula I prepared by an antisolvent method described herein Antisol-1.

FIG. 5A shows an XRPD spectrum of a sample of the Form II polymorph of Formula I.

FIG. 5B shows an XRPD spectrum of a sample of the Form I polymorph of Formula I.

FIG. 5C shows an XRPD spectrum of a sample of the Form III polymorph of Formula I.

FIG. 5D shows an XRPD spectrum of a sample of the Form IV polymorph of Formula I.

FIG. 10A shows an XRPD spectrum of a sample of the Form A polymorph of Formula II (fumagill-6-yl N-(trans-4-aminocyclohexyl)carbamate hydroxynaphthoic acid salt) crystallized from acetonitrile.

FIG. 10B shows an XRPD spectrum of a sample of the Form A polymorph of Formula II crystallized from ethyl acetate.

FIG. 10C shows an XRPD spectrum of a sample of the Form A polymorph of Formula II crystallized from methyl ethyl ketone.

FIG. 10D shows an XRPD spectrum of a sample of the Form A polymorph of Formula II crystallized from tetrahydrofuran.

DETAILED DESCRIPTION

Polymorphs of the Present Application

Figure 1C:
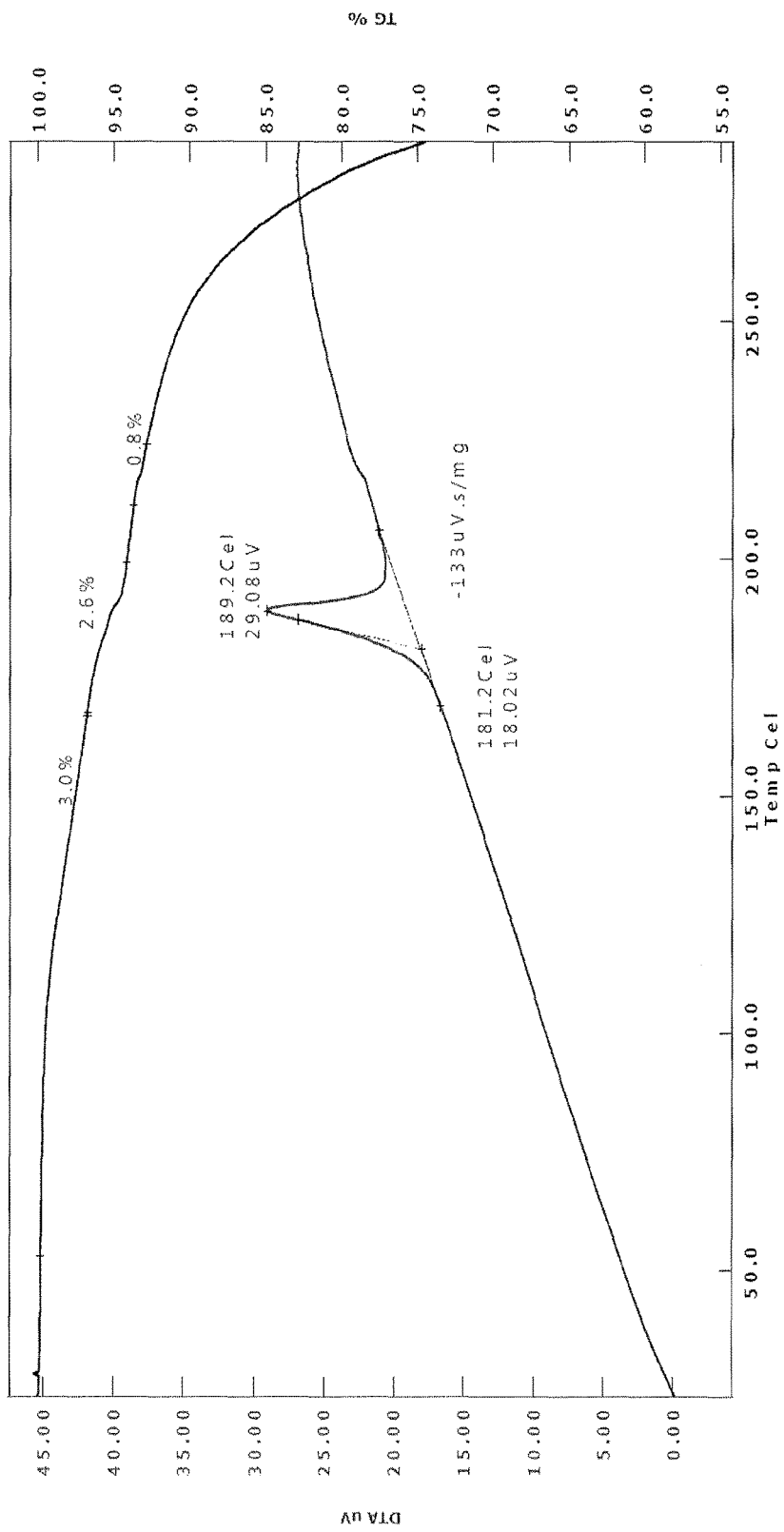
FIG. 1C shows a TG/DTA plot of a sample of the Form II polymorph of Formula I. The TG plot is the top trace and the DTA plot is the bottom trace.

The present disclosure relates to salts of aminoalkylfumagillol carbamates (e.g., benzenesulfonic acid salt and hydroxynaphthoate salt) and polymorphs thereof. Specifically, the present disclosure describes crystalline polymorphs of fumagill-6-yl N-(trans-4-aminocyclohexyl)carbamate benzenesulfonic acid salt (Formula I) and fumagill-6-yl N-(trans-4-aminocyclohexyl)carbamate hydroxynaphthoic acid salt (Formula II). The crystalline polymorphs of Formula I can be Form I, Form II, Form III, or Form IV. In some embodiments, the polymorph is Form II. In some embodiments the polymorphs are solvates. The present disclosure also provides polymorphic Form A of Formula II. The crystalline polymorphs described herein can be used as intermediates in the synthesis of polymer-conjugated derivatives of fumagillol, or as therapeutic agents.

In one or more embodiments, the present disclosure provides a composition comprising a highly pure compound of Formula I or Formula II. In some embodiments, the composition may further comprise a pharmaceutical carrier. In some embodiments, the compound of Formula I or II is highly pure, e.g., having a purity of greater than about 91%, about 92%, about 93%, about 94%, about 95%, about 96%, about 97%, about 98%, about 99%, 99.5%, about 99.9%, or about 99.99%. A compound of Formula I or II (i.e., benzenesulfonic acid salt of fumagill-6-yl N-(trans-4-aminocyclohexyl)carbamate or fumagill-6-yl N-(trans-4-aminocyclohexyl)carbamate hydroxynaphthoic acid salt) can be prepared in a high purity (e.g., a purity of greater than about 91%, about 92%, about 93%, about 94%, about 95%, about 96%, about 97%, about 98%, about 99%, 99.5%, about 99.9%, or about 99.99%) through crystallization. Without wising to be bound by theory, the high purity of a compound such as Formula I or II can be difficult to achieve with the free base (i.e., fumagill-6-yl N-(trans-4-aminocyclohexyl) carbamate free base) or certain other salts of fumagill-6-yl N-(trans-4-aminocyclohexyl)carbamate), due to a significant amount of impurities, for example, as a result of self-condensation of the free base.

In some embodiments, the polymorphs or Formula I or II described herein comprise solvates. The solvent present in the solvates can be, for instance, an organic solvent from which the polymorph is crystallized, or water. In some embodiments, the solvent can be water or MTBE. In some embodiments, the polymorphs described herein contain less than 10% solvent such as MTBE (e.g., <5%, <4%, <3%, <2%, or <1% solvent). In some embodiments, the polymorphs contain less than 1% water (e.g., <0.5%, <0.4%, <0.3%, <0.2%, or <0.1%). In addition to MTBE, the solvent can be an organic solvent used in the recrystallization process such as ethyl acetate.

As defined herein, "XRPD" or "XPD" is understood to mean X-ray powder diffraction. The abbreviation "DSC" is understood to mean differential scanning calorimetry. The abbreviation "TG" is understood to mean thermogravimetry. The abbreviation "DTA" is understood to mean differential thermal analysis and the abbreviation "TG/DTA" is understood to mean thermogravimetry/differential thermal analysis.

As defined herein, "GMP" is understood to mean Good Manufacturing Practice.

As used herein, "MTBE" means methyl tert-butyl ether, also known as tBME.

As defined herein, "pure" is understood to mean that a compound is uniform in chemical makeup. It is understood that a pure compound does not contain molecules of another chemical makeup in an appreciable amount, e.g., less than 5%, less than 4%, less than 3%, less than 2%, or less than 1%. In some instances, the purity is measured excluding any solvent (e.g., organic solvent such as MTBE and ethyl acetate, and inorganic solvent such as water).

As defined herein, "stable" or "stability" relates to the ability of a compound to remain pure for a period of time. A stable compound can be one that maintains its purity (e.g., does not have molecules of an undesired chemical formula) despite extended storage (e.g., greater than one month, greater than six months, or greater than a year). A stable compound can also be a compound that remains pure despite conditions such as high temperature or humidity.

Figure 6A:
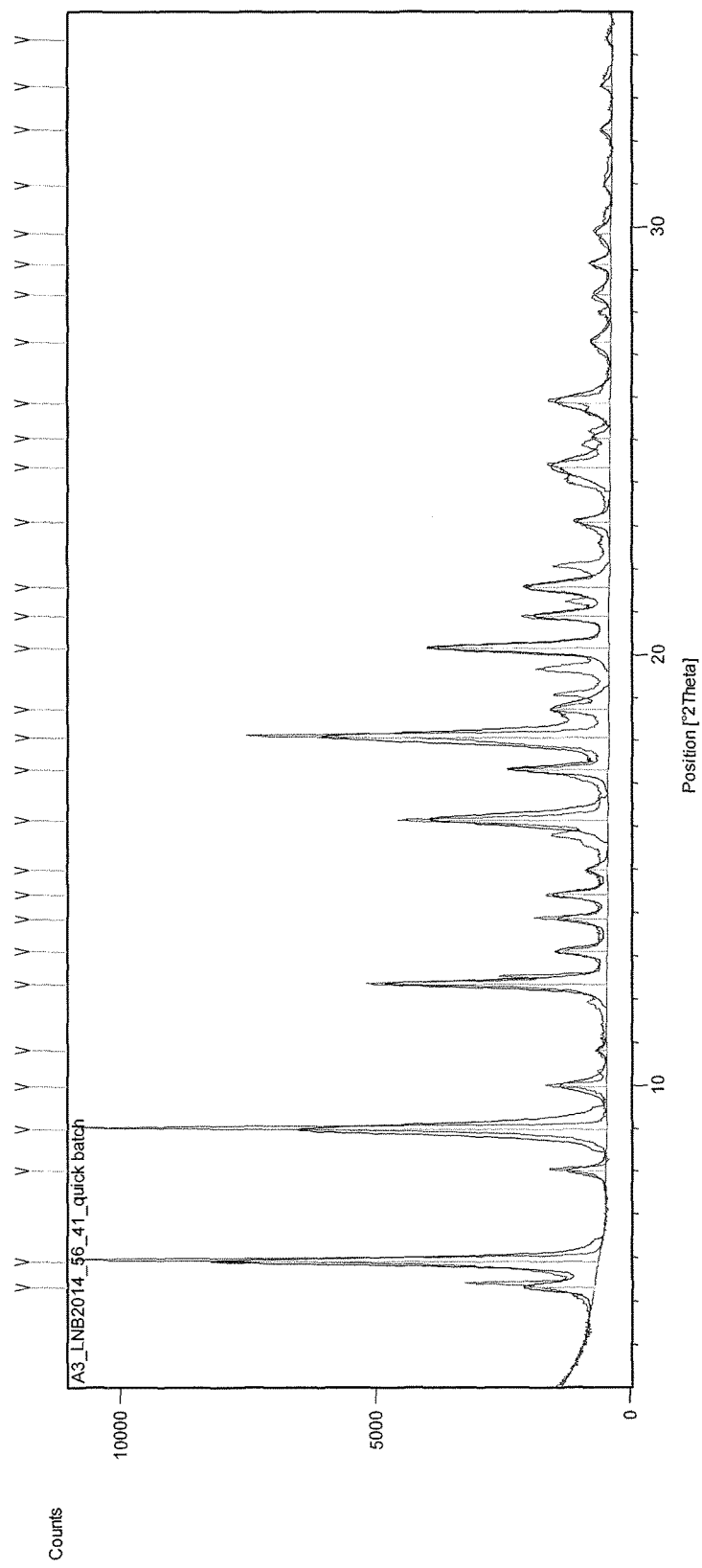
FIG. 6A shows an XRPD spectrum of a sample of the Form II polymorph of Formula I with peaks picked. The list of peaks is provided in Tables 2, 3, 4, 5, 6 and 7.
Figure 6B:
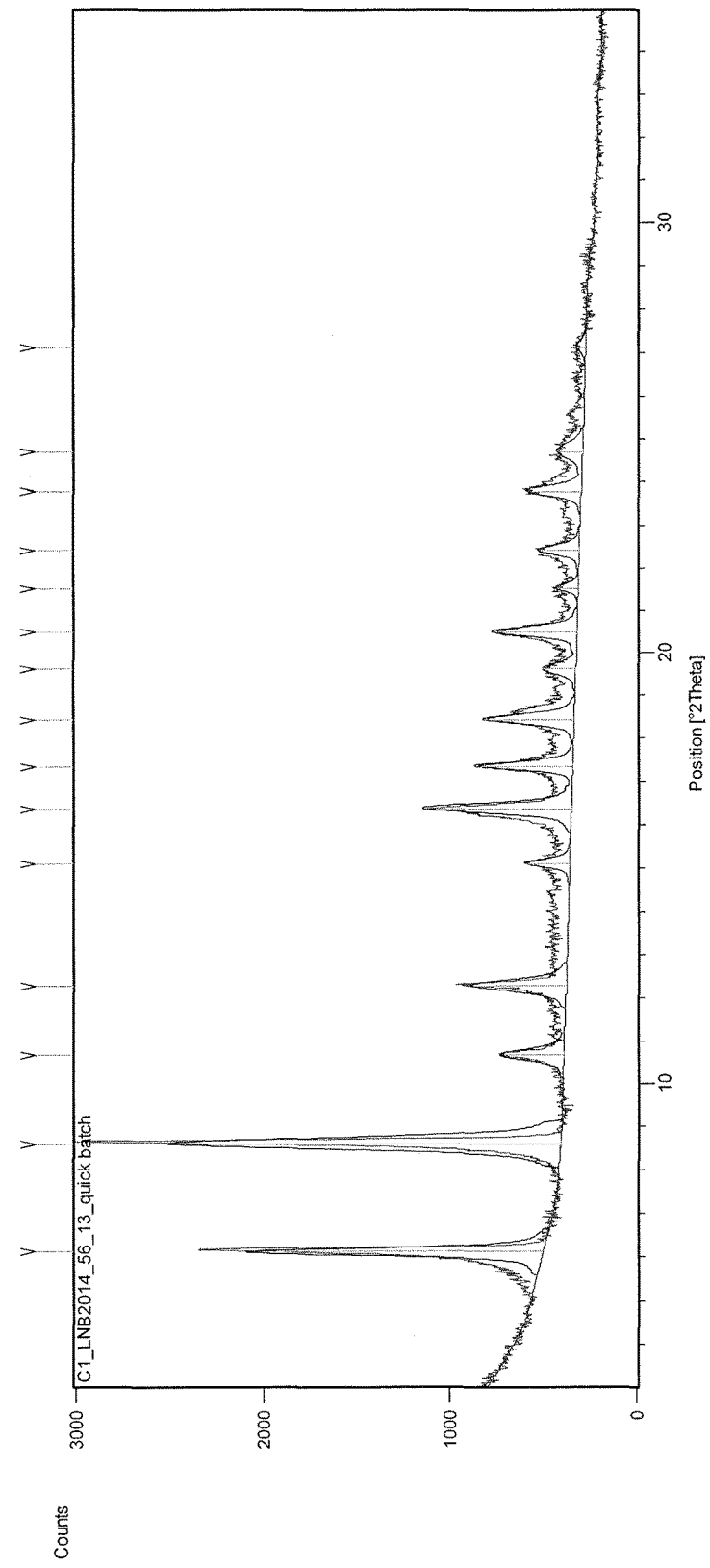
FIG. 6B shows an XRPD spectrum of a sample of the Form I polymorph of Formula I with peaks picked. The list of peaks is provided in Table 1.

Formula I: Fumagill-6-yl
N-(trans-4-aminocyclohexyl)carbamate
Benzenesulfonic Acid Salt Form I, Formula I Form I of fumagill-6-yl N-(trans-4-aminocyclohexyl)carbamate benzenesulfonic acid salt (Formula I) can be crystallized from acetonitrile, for example, at about 50° C., and from dichloromethane, for example, at about 5° C. In some embodiments, Form I of Formula I has peaks as measured by XRPD at about 6.1, 8.6, and 16.4° 2θ. For instance, Form I of Formula I can have peaks at about 6.1, 8.6, 12.3, 16.4, 17.4, and 18.4° 2θ. For instance, Form I of Formula I can have peaks at about 6.1, 8.6, 10.7, 12.3, 16.4, 17.4, 18.4, 20.5, and 23.8° 2θ. For instance, Form I of Formula I can have peaks at about 6.1, 8.6, 10.7, 12.3, 15.1, 16.4, 17.4, 18.4, 20.5, 22.4, 23.8, and 24.7° 2θ. For instance, Form I of Formula I can have peaks as those listed in Table 1. In some embodiments, Form I of Formula I has an X-ray diffraction pattern substantially similar to that set forth in FIG. 5B or 6B.

TABLE 1

XRPD Form I, Formula I

| Pos. [°2Th.] | Height [cts] | Rel. Int. [%] |
| --- | --- | --- |
| 6.1167 | 1429.4 | 75.72 |
| 8.6007 | 1887.72 | 100 |
| 10.6694 | 310.56 | 16.45 |
| 12.2829 | 461.9 | 24.47 |
| 15.1132 | 222.16 | 11.77 |
| 16.3746 | 730.79 | 38.71 |
| 17.351 | 490.17 | 25.97 |
| 18.4292 | 450.01 | 23.84 |
| 19.613 | 158.82 | 8.41 |
| 20.501 | 420.58 | 22.28 |
| 21.5361 | 114.62 | 6.08 |
| 22.4222 | 208.25 | 11.03 |
| 23.785 | 272.15 | 14.42 |
| 24.6863 | 126.02 | 6.68 |
| 27.0994 | 46.3 | 2.45 |

Form II, Formula I

Form II of fumagill-6-yl N-(trans-4-aminocyclohexyl) carbamate benzenesulfonic acid salt (Formula I) can be crystallized from a number of solvents. The solvents include, but are not limited to acetone, anisole, 1-butanol, cyclohexane, diisopropyl ether, 1,4 dioxane, ethyl acetate, heptane, hexane, isopropyl acetate, methylethyl ketone, methylisobutyl ketone, methyltetrahydrofuran, tert-butylmethyl ether, tetrahydrofuran, and toluene, and a mixture thereof.

Various batches of the Form II polymorph are described below.

Batch "GMP-1" was produced using good manufacturing practice on a 65-gram scale. The crystals had a rod-like morphology as characterized by polarized light microscopy (PLM).

Batch "GMP-2" was produced using good manufacturing practice on a 60-gram scale. The crystals had a rod-like morphology as characterized by polarized light microscopy (PLM).

Batch "Cooling-1" was produced on an 8-gram scale as set forth in Example 3, below. The batch was produced by dissolving fumagill-6-yl N-(trans-4-aminocyclohexyl)carbamate benzenesulfonic acid salt in 39 mL of a 50:50 mixture of methyl-tert-butyl ether (MTBE) and methanol. The compound was dissolved at 50° C. and slowly cooled to 5° C. before adding additional MTBE. Three samples were taken from batch Cooling-1, at points (i) before adding additional MTBE, (ii) after addition of 30 mL MTBE, and (iii) after addition of 60-mL MTBE. XRPD spectra of the three samples taken from batch Cooling-1 are shown in FIGS. 3A, 3B and 3C, respectively.

Batch "Antisol-1" was produced on an 8-gram scale as set forth in Example 4, below. The batch was produced by dissolving fumagill-6-yl N-(trans-4-aminocyclohexyl)carbamate benzenesulfonic acid salt in 39 mL of a 50:50 mixture of methyl-tert-butyl ether (MTBE) and methanol. The compound was dissolved at 50° C. and additional MTBE was added before the solution was cooled to 5° C. Three samples were taken from batch Antisol-1, at points (i) before adding additional MTBE, (ii) after addition of 30 mL MTBE, and (iii) after addition of 60-mL MTBE. XRPD spectra of the three samples taken from batch Antisol-1 are shown in FIGS. 4A, 4B and 4C, respectively.

In one aspect, the present disclosure provides a polymorph (Form II) of fumagill-6-yl N-(trans-4-aminocyclohexyl)carbamate benzenesulfonic acid salt that is characterized by an X-ray powder diffraction pattern including peaks at about 6.0, 9.0, and 18.0 (e.g., about 5.96, 9.00, and 18.02) ° 2θ using Cu Kα radiation.

In one embodiment, Form II is further characterized by an X-ray powder diffraction pattern including peaks at about 6.0, 9.0, and 18.0° 2θ using Cu Kα radiation. In one embodiment, Form II is further characterized by an X-ray powder diffraction pattern including peaks at about 6.0, 9.0, 12.3, 12.5, 16.1, and 18.0° 2θ using Cu Kα radiation. In another embodiment, Form II is further characterized by an X-ray powder diffraction pattern including peaks at about 6.0, 9.0, 12.3, 12.5, 13.8, 16.1, 18.0, 20.0, and 25.8° 2θ using Cu Kα radiation. In another embodiment, Form II is further characterized by an X-ray powder diffraction pattern including peaks at about 5.4, 6.0, 9.0, 12.3, 12.5, 13.8, 16.1, 17.3, 18.0, 20.0, 20.8, and 25.8° 2θ using Cu Kα radiation. In another embodiment, Form II is further characterized by an X-ray powder diffraction pattern including peaks at about 5.4, 6.0, 9.0, 12.3, 12.5, 13.8, 16.1, 17.3, 18.0, 20.0, 20.8, 21.5, 22.0, 24.3, and 25.8° 2θ using Cu Kα radiation. In another embodiment, Form II of Formula I is further characterized by an X-ray powder diffraction pattern including peaks as those listed in any of Tables 2-7.

In one or more embodiments, Form II is further characterized by an X-ray powder diffraction pattern substantially similar to that set forth in FIG. 1A. In one or more embodiments, Form II is further characterized by an X-ray powder diffraction pattern substantially similar to that set forth in FIG. 2A. In one or more embodiments, Form II is further characterized by an X-ray powder diffraction pattern substantially similar to that set forth in FIG. 3A, 3B or 3C. In one or more embodiments, Form II is further characterized by an X-ray powder diffraction pattern substantially similar to that set forth in FIG. 4A, 4B or 4C. In one or more embodiments, Form II is further characterized by an X-ray powder diffraction pattern substantially similar to that set forth in FIG. 5A. In one or more embodiments, Form II is further characterized by an X-ray powder diffraction pattern substantially similar to that set forth in FIG. 6A.

Figure 2B:
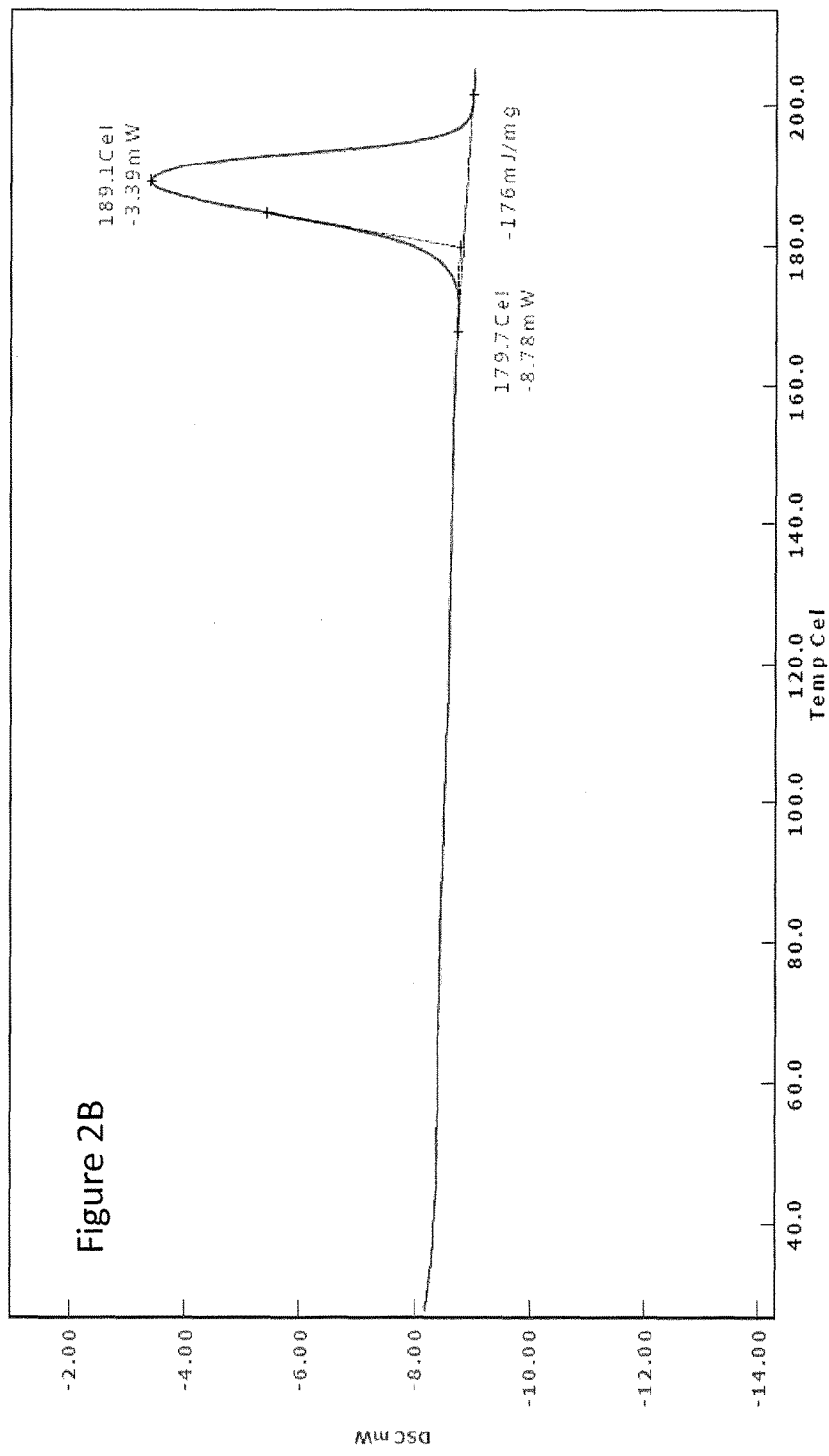
FIG. 2B shows a DSC curve of a sample of the Form II polymorph of Formula I.
Figure 2C:
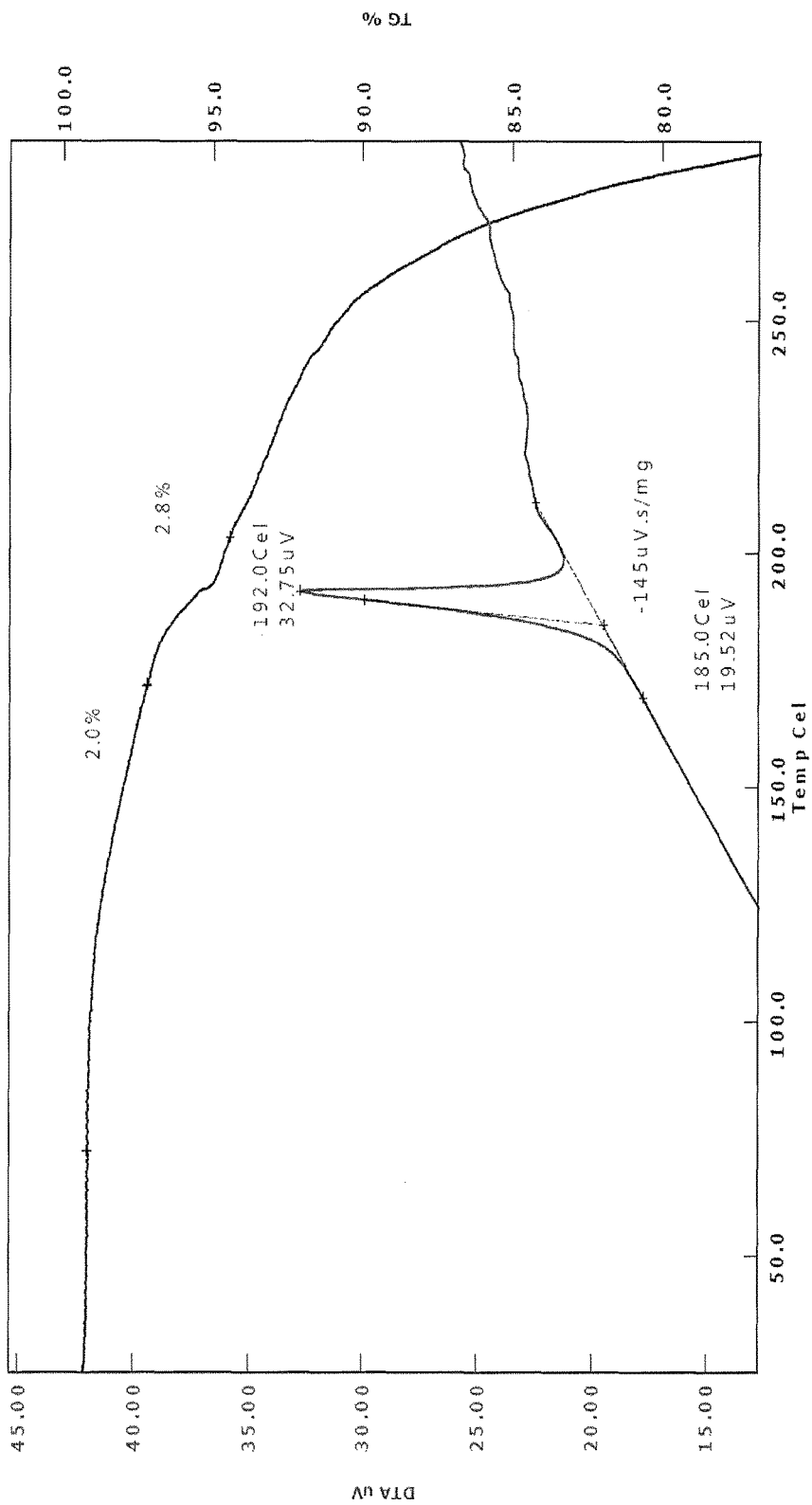
FIG. 2C shows a TG/DTA plot of a sample of the Form II polymorph of Formula I. The TG plot is the top trace and the DTA plot is the bottom trace.

In one or more embodiments, the Form II polymorph is characterized by an exothermic event onset at about 178° C. and a peak at about 188° C., as measured by differential scanning calorimetry. Set forth in FIG. 1B and FIG. 2B is a DSC plot of Form II of Formula I. In one or more embodiments, the Form II polymorph is characterized by an exothermic onset at about 181° C. and a peak at about 191° C., as measured by thermogravimetric analysis/differential thermal analysis. FIGS. 1C and 2C set forth a TG/DTA plot of a of a sample of Form II of Formula I.

As shown in the tables and figures of the present application, not all values for peaks (pos. ° 2θ) are identical for different lots of the polymorphs of the present application. An artisan of ordinary skill will understand that even different lots of the same polymorphic forms can produce slightly different characterization data, while not being appreciably different. For instance, slight variations in the calibration of the instruments used to perform a given measurement, or minor fluctuations in relative humidity between measurements can give rise to data that displays slight differences between lots. One of ordinary skill in the art will thus be able to, for instance, calibrate his or her instruments and take repeated measurements in order to minimize any discrepancies between signals to properly characterize the polymorphs of the present application. However, despite some minor variation in the batch-to-batch differences, polymorphs of the present application are identified and characterized by their characteristic peaks, such as those described above (e.g., about 6.0, 9.0, and 18.0° 2θ, for instance ±0.2° 2θ).

TABLE 2

XRPD: Form II Lot GMP-1

| Pos. [°2Th.] | Height [cts] | Rel. Int. [%] |
|---|---|---|
| 8.99 | 2292.63 | 100 |
| 18.02 | 1194.53 | 52.1 |
| 5.96 | 1055.05 | 46.02 |
| 16.08 | 794.78 | 34.67 |
| 12.48 | 528.62 | 23.06 |
| 12.32 | 508.7 | 22.19 |
| 20.04 | 353.67 | 15.43 |
| 13.82 | 326.19 | 14.23 |
| 25.78 | 310.13 | 13.53 |
| 5.39 | 306.46 | 13.37 |
| 20.79 | 281.18 | 12.26 |

TABLE 2-continued

XRPD: Form II Lot GMP-1

| Pos. [°2Th.] | Height [cts] | Rel. Int. [%] |
|---|---|---|
| 17.27 | 249.04 | 10.86 |
| 24.32 | 217.84 | 9.5 |
| 21.54 | 210.18 | 9.17 |
| 21.98 | 208.01 | 9.07 |
| 10.00 | 203.08 | 8.86 |
| 14.38 | 202.31 | 8.82 |
| 19.61 | 179.49 | 7.83 |
| 19.00 | 172.73 | 7.53 |
| 21.14 | 161.24 | 7.03 |
| 15.79 | 138.7 | 6.05 |
| 13.07 | 128.38 | 5.6 |
| 23.94 | 99.23 | 4.33 |
| 18.70 | 94.49 | 4.12 |
| 23.01 | 91.22 | 3.98 |
| 29.03 | 68.33 | 2.98 |
| 28.21 | 56.3 | 2.46 |
| 33.11 | 46.77 | 2.04 |
| 14.94 | 37.71 | 1.64 |
| 29.68 | 35.69 | 1.56 |
| 32.16 | 35.39 | 1.54 |
| 34.25 | 33.94 | 1.48 |
| 27.06 | 33.53 | 1.46 |
| 27.82 | 30.73 | 1.34 |

TABLE 3

XRPD: Form II Lot GMP-2

| Pos. [°2Th.] | Height [cts] | Rel. Int. [%] |
|---|---|---|
| 9.00 | 6533.85 | 100 |
| 18.02 | 4057.53 | 62.1 |
| 5.95 | 3332.7 | 51.01 |
| 12.32 | 1756.69 | 26.89 |
| 12.48 | 1360.92 | 20.83 |
| 16.08 | 1300.05 | 19.9 |
| 13.82 | 1085.52 | 16.61 |
| 17.87 | 1078.09 | 16.5 |
| 20.03 | 1007.35 | 15.42 |
| 20.14 | 899 | 13.76 |
| 5.39 | 896.21 | 13.72 |
| 14.36 | 815.25 | 12.48 |
| 17.26 | 784.67 | 12.01 |
| 25.79 | 758.4 | 11.61 |
| 20.79 | 745.89 | 11.42 |
| 21.97 | 669.33 | 10.24 |
| 18.99 | 652.12 | 9.98 |
| 9.99 | 648.17 | 9.92 |
| 24.31 | 646.65 | 9.9 |
| 21.13 | 598.47 | 9.16 |
| 15.74 | 595.88 | 9.12 |
| 21.51 | 585.44 | 8.96 |
| 13.06 | 579.41 | 8.87 |
| 19.62 | 557.36 | 8.53 |
| 17.02 | 499.73 | 7.65 |
| 18.69 | 465.8 | 7.13 |
| 8.01 | 426.96 | 6.53 |
| 14.91 | 405.49 | 6.21 |
| 10.78 | 392.79 | 6.01 |
| 23.90 | 380.52 | 5.82 |
| 23.00 | 305.39 | 4.67 |
| 24.78 | 276.59 | 4.23 |
| 22.78 | 260.64 | 3.99 |
| 25.52 | 242.18 | 3.71 |
| 25.08 | 220.39 | 3.37 |
| 28.99 | 209.17 | 3.2 |
| 29.76 | 200.54 | 3.07 |
| 28.22 | 197.55 | 3.02 |
| 27.13 | 184.71 | 2.83 |

TABLE 3-continued

XRPD: Form II Lot GMP-2

| Pos. [°2Th.] | Height [cts] | Rel. Int. [%] |
|---|---|---|
| 27.83 | 167.87 | 2.57 |
| 33.09 | 144.72 | 2.21 |
| 32.11 | 136.73 | 2.09 |
| 30.78 | 92.44 | 1.41 |
| 34.20 | 54.61 | 0.84 |

TABLE 4

XRPD: Form II Sample 1

| Pos. [°2θ] | Height [cts] | Rel. Int. [%] |
|---|---|---|
| 8.9883 | 29895.24 | 100 |
| 5.9444 | 24665.57 | 82.51 |
| 17.905 | 4967.24 | 16.62 |
| 12.3277 | 7943.24 | 26.57 |
| 16.1017 | 9049.99 | 30.27 |
| 20.0906 | 6290.97 | 21.04 |
| 19.6629 | 2957.3 | 9.89 |
| 17.272 | 3388.1 | 11.33 |
| 17.1718 | 1690.94 | 5.66 |
| 12.4867 | 3321.58 | 11.11 |
| 13.8231 | 3650.26 | 12.21 |
| 20.8269 | 3124.43 | 10.45 |
| 5.3838 | 6026.77 | 20.16 |
| 21.1492 | 1553.58 | 5.2 |
| 15.7853 | 2741.92 | 9.17 |

TABLE 5

XRPD: Form II Sample 2

| Pos. [°2θ] | Height [cts] | Rel. Int. [%] |
|---|---|---|
| 8.9899 | 19068.27 | 100 |
| 5.9315 | 16639.22 | 87.26 |
| 18.0439 | 12566.18 | 65.9 |
| 12.3263 | 7583.04 | 39.77 |
| 16.0756 | 6535.63 | 34.27 |
| 20.1243 | 4851.73 | 25.44 |
| 20.0439 | 4842.6 | 25.4 |
| 17.8661 | 3990.95 | 20.93 |
| 17.267 | 3364.67 | 17.65 |
| 12.4884 | 3327.18 | 17.45 |
| 13.8234 | 3066.38 | 16.08 |
| 20.8208 | 2990.29 | 15.68 |
| 5.3789 | 2987.29 | 15.67 |
| 21.5186 | 2508.08 | 13.15 |
| 15.746 | 2458.11 | 12.89 |

TABLE 6

XRPD: Form II Sample 3

| Pos. [°2θ] | Height [cts] | Rel. Int. [%] |
|---|---|---|
| 8.9857 | 8341.43 | 72.47 |
| 5.9053 | 11509.82 | 100 |
| 18.0327 | 6950.15 | 60.38 |
| 12.2907 | 5921.19 | 51.44 |
| 16.0291 | 5586.66 | 48.54 |
| 20.0889 | 4141.24 | 35.98 |

TABLE 6-continued

XRPD: Form II Sample 3

| Pos. [°2θ] | Height [cts] | Rel. Int. [%] |
|---|---|---|
| 19.9747 | 4522.96 | 39.3 |
| 17.8002 | 2620.14 | 22.76 |
| 17.2407 | 3139.83 | 27.28 |
| 12.4818 | 1890.54 | 16.43 |
| 13.8238 | 1949.89 | 16.94 |
| 20.7951 | 2335.76 | 20.29 |
| 5.3727 | 1693.62 | 14.71 |
| 21.4331 | 2515.86 | 21.86 |
| 15.6809 | 2585.84 | 22.47 |

TABLE 7

XRPD: Form II Sample 4

| Pos. [°2Th.] | Height [cts] | Rel. Int. [%] |
|---|---|---|
| 5.3093 | 1244.06 | 18.28 |
| 5.8984 | 6804.14 | 100 |
| 7.9915 | 707.93 | 10.4 |
| 8.9709 | 5449.2 | 80.09 |
| 9.9856 | 825.88 | 12.14 |
| 10.8292 | 176.02 | 2.59 |
| 12.3361 | 3965.52 | 58.28 |
| 13.0963 | 939.36 | 13.81 |
| 13.8426 | 896.8 | 13.18 |
| 14.4041 | 995.36 | 14.63 |
| 14.9915 | 377.62 | 5.55 |
| 16.1437 | 3176.27 | 46.68 |
| 17.3169 | 1815.16 | 26.68 |
| 18.058 | 5119.79 | 75.25 |
| 18.7258 | 1009.12 | 14.83 |
| 20.1593 | 3343.08 | 49.13 |
| 20.909 | 1389.65 | 20.42 |
| 21.5739 | 1544.49 | 22.7 |
| 23.0932 | 669.98 | 9.85 |
| 24.3348 | 1052.13 | 15.46 |
| 25.017 | 365.35 | 5.37 |
| 25.8461 | 973.81 | 14.31 |
| 27.263 | 378.02 | 5.56 |
| 28.4112 | 319.74 | 4.7 |
| 29.1217 | 426.3 | 6.27 |
| 29.8278 | 286.56 | 4.21 |
| 30.9418 | 143.49 | 2.11 |
| 32.2423 | 215.01 | 3.16 |
| 33.2569 | 205.76 | 3.02 |
| 34.3252 | 106.84 | 1.57 |

Polarimetry Data

Table 8 presents the polarimetry data for lots GMP-1 and GMP-2 of Formula I.

TABLE 8

Polarimetry data for Form II Lots GMP-1 and GMP-2.

| Sample | Weight (mg) | Volume (mL) | Concentration (mg/mL) | Angle (°) | Temperature (° C.) | Optical Rotation |
|---|---|---|---|---|---|---|
| GMP-1 | 12.12 | 1.1 | 1.1 | −0.315 | 25.75 | −28.59 |
| GMP-1 | 10x Dilution | | 0.11 | −0.029 | 26.01 | −26.32 |
| GMP-2 | 11.4 | 1.1 | 1.04 | −.306 | 26.2 | −29.53 |
| GMP-2 | 10x Dilution | | 0.1 | −0.03 | 26.27 | −28.95 |

Single Crystal X-Ray Analysis (SXRD)

Figure 8:
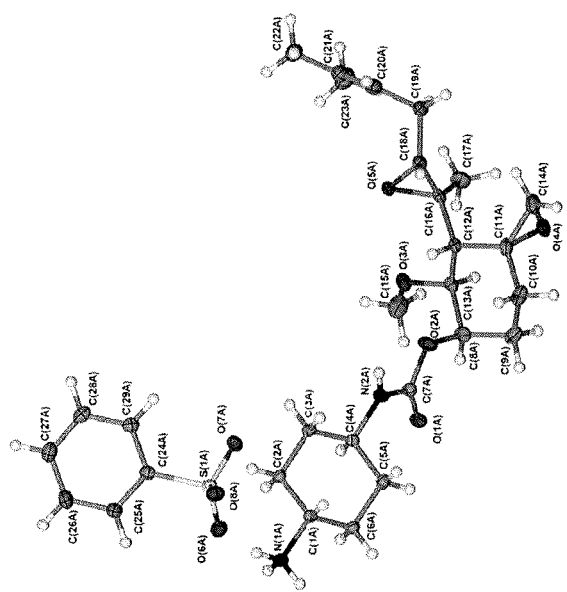
FIG. 8 shows a single molecule view by SXRD analysis of the Form II polymorph of Formula I.

A crystal structure of Formula I is given in FIG. 8. All non-hydrogen atoms are shown with thermal ellipsoids set at 30% probability levels.

The asymmetric unit was found to contain two complete formula units of protonated fumagill-6-yl N-(trans-4-aminocyclohexyl)carbamate with two associated benzenesulfonate anions only. During the refinement, large thermal displacement ellipsoids were noted for carbon atoms C(20B), C(21B), C(22B) and C(23B), of the molecule 'B' alkene moiety.

Further disorder was noted for benzenesulfonate 'molecule B' centered on sulfur atom S(1B) which also exhibited large thermal displacement ellipsoids for benzyl-ring C(24B)<C(29B). Rotational disorder in the sulfonate moiety of this molecule, centered on S(1B), was noted and successfully modelled with occupancies of 0.78:0.22 and fixed bond distances of 1.48(1) for S(1B)—O(6B) and S(1B)—O(8C), and 1.44(1) for S(1B)—O(7C).

Approximately 1.5% of the unit cell was found to be occupied by two solvent voids measuring approximately 168 Å$^3$ and 812 Å$^3$, filled with electron density equaling 74 and 137 electrons respectively. Without wising to be bound by theory, it is most likely that these arise from disordered solvent molecules therefore the electron density within these voids were modelled with small mole-fractions of solvent molecules; 0.27 equivalents of water, 0.12 equivalents of methanol and 0.06 equivalents of MTBE. Of these, partially occupied methanol and two partially occupied water molecules were refined at the unit cell origin.

To correct for extinction effects in the observed data, an extinction correction of 0.00031(3) was applied and all hydrogen atoms were placed in calculated positions and refined using a riding model with fixed Uiso of 1.2 times for all CH, CH$_2$, NH, and NH$_3$ groups, and fixed Uiso of 1.5 times for all CH$_3$ groups.

The highest residual Fourier peak was 0.80 e. Å$^3$ approx. 1.1 Å$^3$ from C(30). Without wishing to be bound by theory, this likely arises from further disorder present in the solvent void occupied by modelled MTBE molecule centered on O(9). The deepest Fourier hole was found to be –0.41 e. Å approximately 1.54 Å from H(9AA).

Form III, Formula I

Figure 6C:
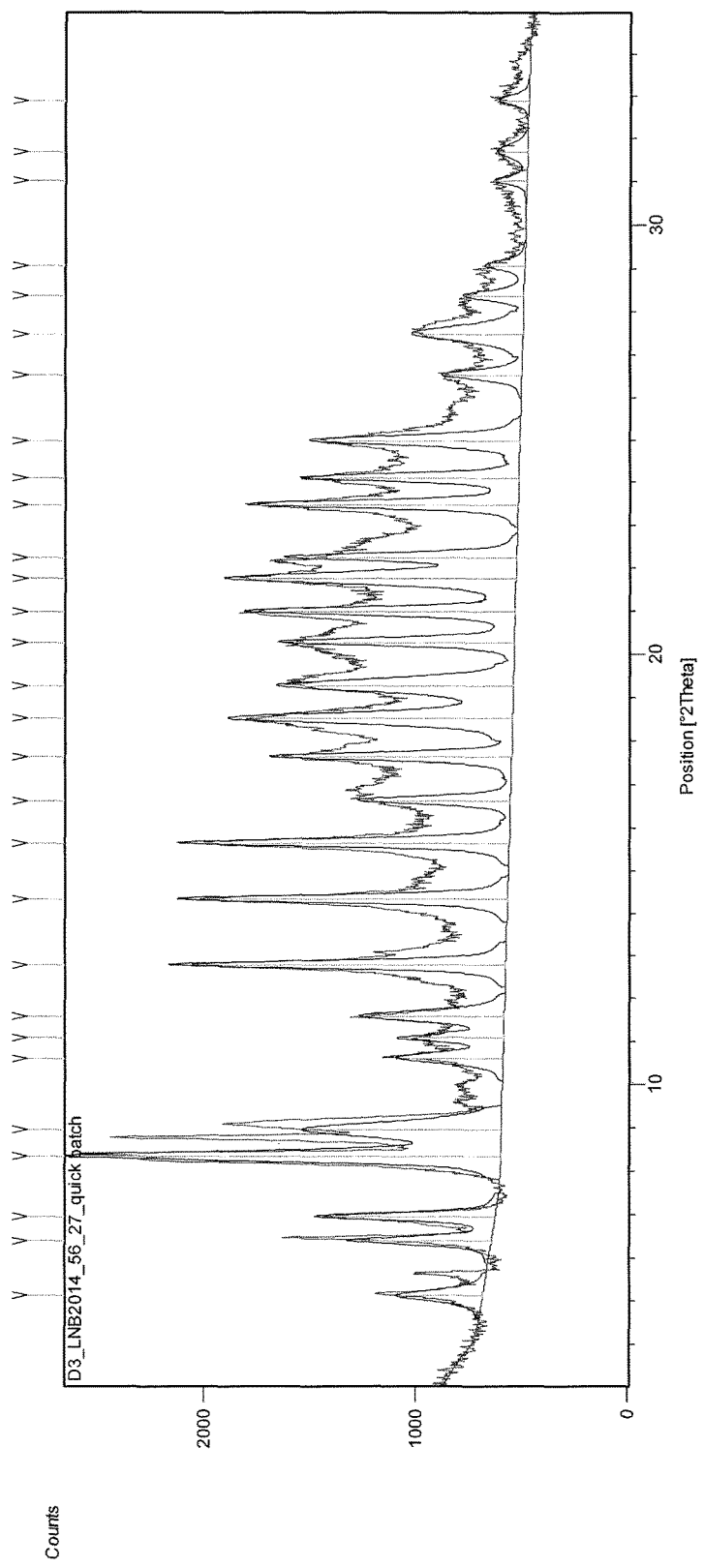
FIG. 6C shows an XRPD spectrum of a sample of the Form III polymorph of Formula I with peaks picked. The list of peaks is provided in Table 9.

The Form III polymorph of fumagill-6-yl N-(trans-4-aminocyclohexyl)carbamate benzenesulfonic acid salt can be crystallized from ethanol and isopropanol, for example, at about 50° C. to about 5° C. In some embodiments, Form III of Formula I has XRPD peaks at about 8.3, 12.8, and 15.7, ° 2 θ. In some embodiments, Form III of Formula I has XRPD peaks at about 8.3, 12.8, 14.3, 15.7, 18.5, and 21.8, ° 2 θ. In some embodiments, Form III of Formula I has XRPD peaks at about 8.3, 12.8, 14.3, 15.7, 17.6, 18.5, 21.0, 21.8, and 23.5° 2 θ. In some embodiments, Form III of Formula I has XRPD peaks at about 8.3, 12.8, 14.3, 15.7, 17.6, 18.5, 19.3, 20.3, 21.0, 21.8, 23.5, and 24.1° 2 θ. In some embodiments, Form III of Formula I has XRPD peaks at about 8.3, 9.0, 12.8, 14.3, 15.7, 17.6, 18.5, 19.3, 20.3, 21.0, 21.8, 22.2, 23.5, 24.1, and 25.0° 2 θ. In some embodiments, Form III has an X-ray diffraction pattern substantially similar to that set forth in FIG. 5C or 6C. In some embodiments, Form III of Formula I has XRPD peaks as those listed in Table 9.

TABLE 9

XRPD Form III, Formula I

| Pos. [°2Th.] | Height [cts] | Rel. Int. [%] |
|---|---|---|
| 5.1248 | 369.56 | 19.97 |
| 6.3894 | 618.31 | 33.41 |
| 6.9527 | 766.75 | 41.43 |

TABLE 9-continued

XRPD Form III, Formula I

| Pos. [°2Th.] | Height [cts] | Rel. Int. [%] |
|---|---|---|
| 8.3369 | 1850.64 | 100 |
| 8.9513 | 846.4 | 45.74 |
| 10.6059 | 450.05 | 24.32 |
| 11.072 | 411.19 | 22.22 |
| 11.5701 | 612.01 | 33.07 |
| 12.7812 | 1447.09 | 78.19 |
| 14.3353 | 1427.54 | 77.14 |
| 15.6538 | 1433.02 | 77.43 |
| 16.6351 | 670.59 | 36.24 |
| 17.628 | 1056.55 | 57.09 |
| 18.5131 | 1222.17 | 66.04 |
| 19.2685 | 1009.03 | 54.52 |
| 20.2738 | 1043.81 | 56.4 |
| 20.982 | 1198.18 | 64.74 |
| 21.7521 | 1239.19 | 66.96 |
| 22.2474 | 980.74 | 52.99 |
| 23.477 | 1216.72 | 65.75 |
| 24.0855 | 986.18 | 53.29 |
| 24.9597 | 929.76 | 50.24 |
| 26.5001 | 357.4 | 19.31 |
| 27.4588 | 483.19 | 26.11 |
| 28.3362 | 269.08 | 14.54 |
| 29.0412 | 177.76 | 9.61 |
| 30.9816 | 153.44 | 8.29 |
| 31.6617 | 133.45 | 7.21 |
| 32.864 | 136.34 | 7.37 |

Form IV, Formula I

Figure 6D:
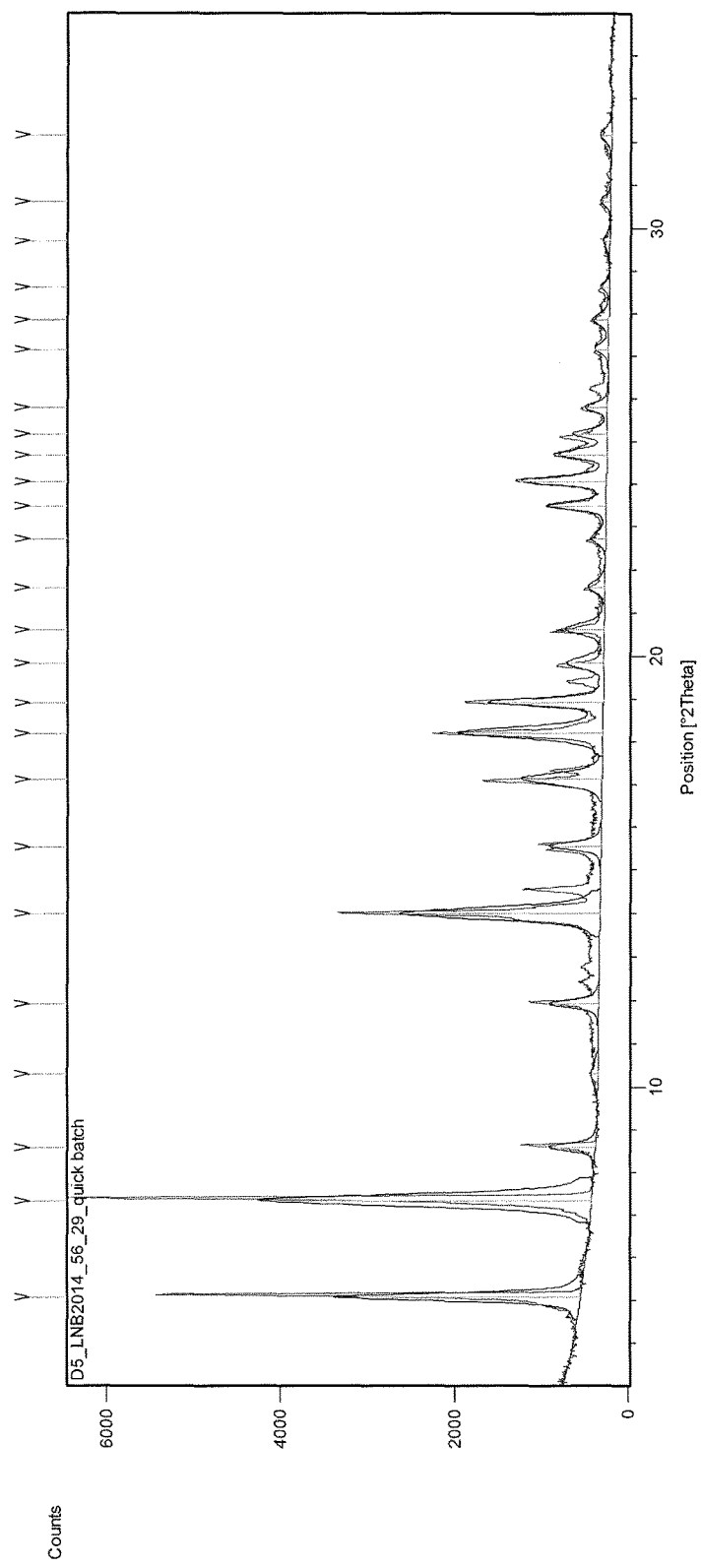
FIG. 6D shows an XRPD spectrum of a sample of the Form IV polymorph of Formula I with peaks picked. The list of peaks is provided in Table 10.

The Form IV polymorph of fumagill-6-yl N-(trans-4-aminocyclohexyl)carbamate benzenesulfonic acid salt can be crystallized from a mixture of isopropanol and water (10%), for example, at about 0° C. and 5° C. In some embodiments, Form IV has XRPD peaks at about 5.1, 7.3, and 14.0° 2 θ. In some embodiments, Form IV has XRPD peaks at about 5.1, 7.3, 14.0, 18.2, 18.9 and 24.1° 2 θ. In some embodiments, Form IV has XRPD peaks at about 5.1, 7.3, 14.0, 17.1, 18.2, 18.9, 23.5, 24.1, and 24.7° 2 θ. In some embodiments, Form IV has an X-ray diffraction pattern substantially similar to that set forth in FIG. 5D or 6D. In some embodiments, Form IV of Formula I has XRPD peaks as those listed in Table 10.

TABLE 10

XRPD Form IV, Formula I

| Pos. [°2Th.] | Height [cts] | Rel. Int. [%] |
|---|---|---|
| 5.0775 | 2559.74 | 74.35 |
| 7.3459 | 3442.92 | 100 |
| 8.5936 | 502.16 | 14.59 |
| 10.3093 | 64.58 | 1.88 |
| 11.9251 | 532.02 | 15.45 |
| 13.9944 | 2086.82 | 60.61 |
| 15.5507 | 563.93 | 16.38 |
| 17.1319 | 861.86 | 25.03 |
| 18.2148 | 1522.11 | 44.21 |
| 18.9336 | 1234.32 | 35.85 |
| 19.8473 | 395.05 | 11.47 |
| 20.6326 | 420.07 | 12.2 |
| 21.5992 | 179.33 | 5.21 |
| 22.7326 | 154.21 | 4.48 |
| 23.4964 | 655.23 | 19.03 |
| 24.0717 | 1007.8 | 29.27 |
| 24.6912 | 588.52 | 17.09 |
| 25.1577 | 373.23 | 10.84 |
| 25.7711 | 255.62 | 7.42 |
| 27.1449 | 150.16 | 4.36 |
| 27.8294 | 171.44 | 4.98 |

TABLE 10-continued

XRPD Form IV, Formula I

| Pos. [°2Th.] | Height [cts] | Rel. Int. [%] |
|---|---|---|
| 28.6064 | 103.14 | 3 |
| 29.67 | 65.19 | 1.89 |
| 30.6056 | 111.81 | 3.25 |
| 32.139 | 119.25 | 3.46 |

Figure 7:
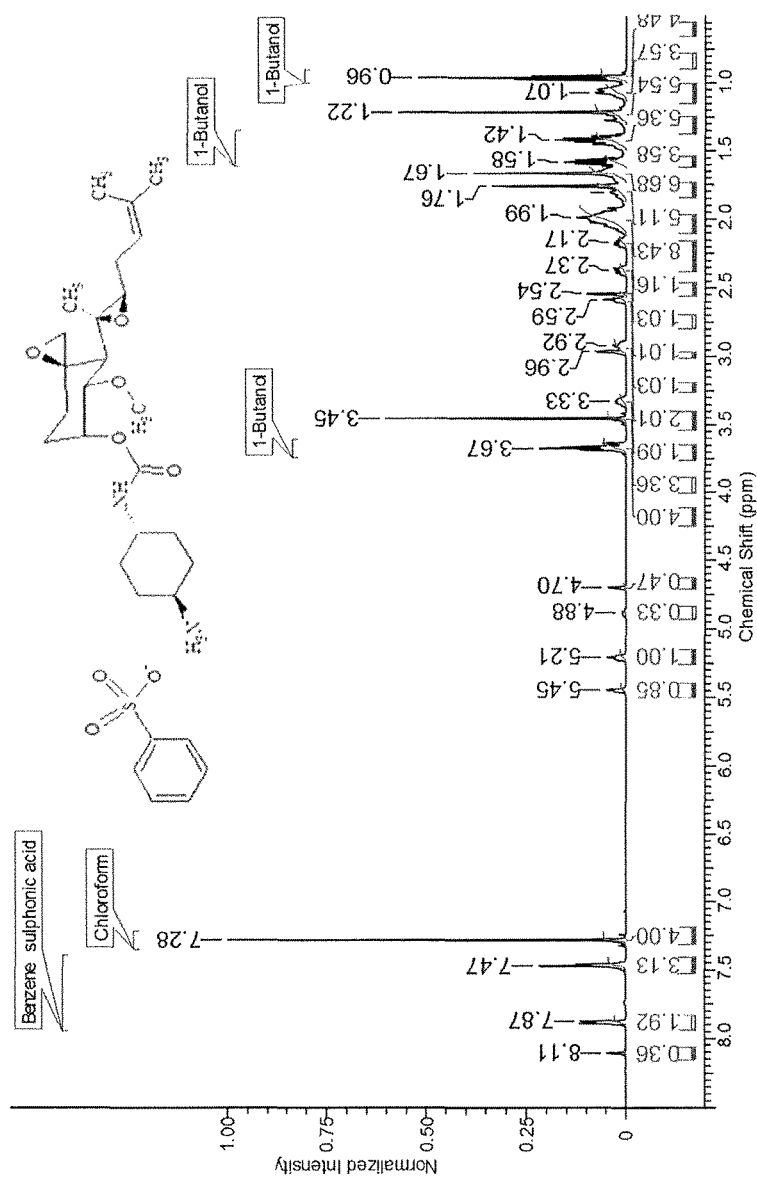
FIG. 7 shows a $^1$H NMR spectrum of Formula I, as well as solvent impurities.

The polymorphs of the present application can possess high purity. In one or more embodiments, purity can be measured by nuclear magnetic resonance (e.g., $^1$H NMR). Representative $^1$H NMR conditions are given below in the experimental section. In some embodiments, fumagill-6-yl N-(trans-4-aminocyclohexyl)carbamate benzenesulfonic acid salt can have a $^1$H NMR spectrum as set forth in FIG. 7. In some embodiments, fumagill-6-yl N-(trans-4-aminocyclohexyl)carbamate benzenesulfonic acid salt can have a $^1$H NMR spectrum as set forth below.

$^1$H NMR (500 MHz, CDCl$_3$) δ 7.89-7.87 (2H, m, ArH), 7.47-7.45 (3H, m, ArH), 5.45 (1H, br s, CH), 5.21 (1H, t, J=6.8 Hz, CH), 3.63 (1H, dd, J=11.3 2.8 Hz, CH), 3.45 (3H, s, OCH$_3$), 3.36-3.30 (1H, br m), 2.97 (1H, d, J=4.1 Hz), 2.92 (1H, t, J=11.7 Hz), 2.59 (1H, t, J=6.1 Hz, CH), 2.55 (1H, d, J=4.1 Hz), 2.40-2.35 (1H, m), 2.20-2.14 (1H, m), 2.08-1.93 (8H, m), 1.84 (1H, d, J=12.9), 1.74 (3H, s, =CCH$_3$), 1.67 (3H, s, =CCH$_3$), 1.48-1.38 (2H, m), 1.28-1.24 (1H, m), 1.22 (2H, s), 1.07 (3H, t, J=12.6 Hz).

In one or more embodiments, purity can be measured by High Performance Liquid Chromatography (HPLC) using an Evaporative Light Scattering Detector (ELSD) or a Charged Aerosol Detector (CAD). Representative HPLC experimental conditions are given below in the experimental section. In some embodiments, fumagill-6-yl N-(trans-4-aminocyclohexyl)carbamate benzenesulfonic acid salt has a retention time of about 8.75 minutes.

Figure 9:
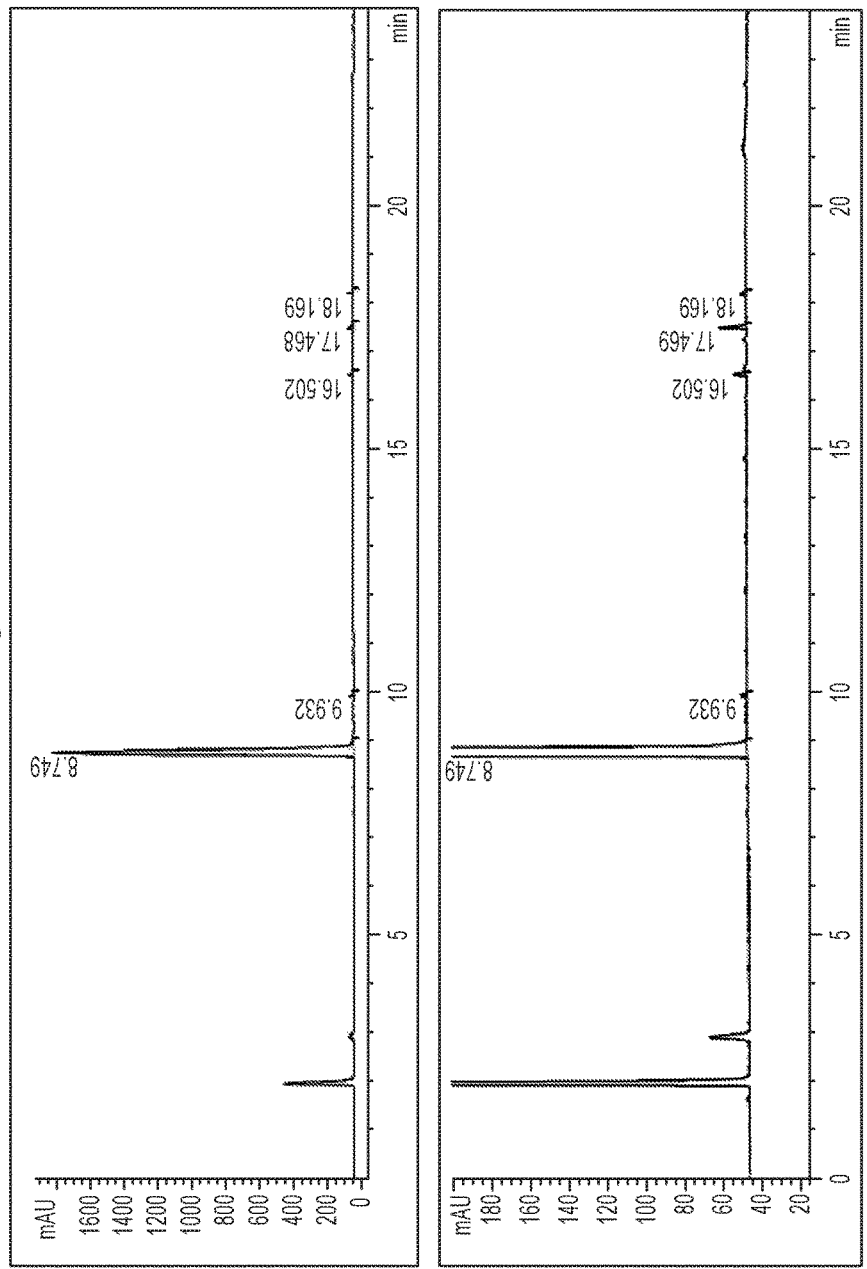
FIG. 9 shows an HPLC analysis of Formula I.
Figure 10E:
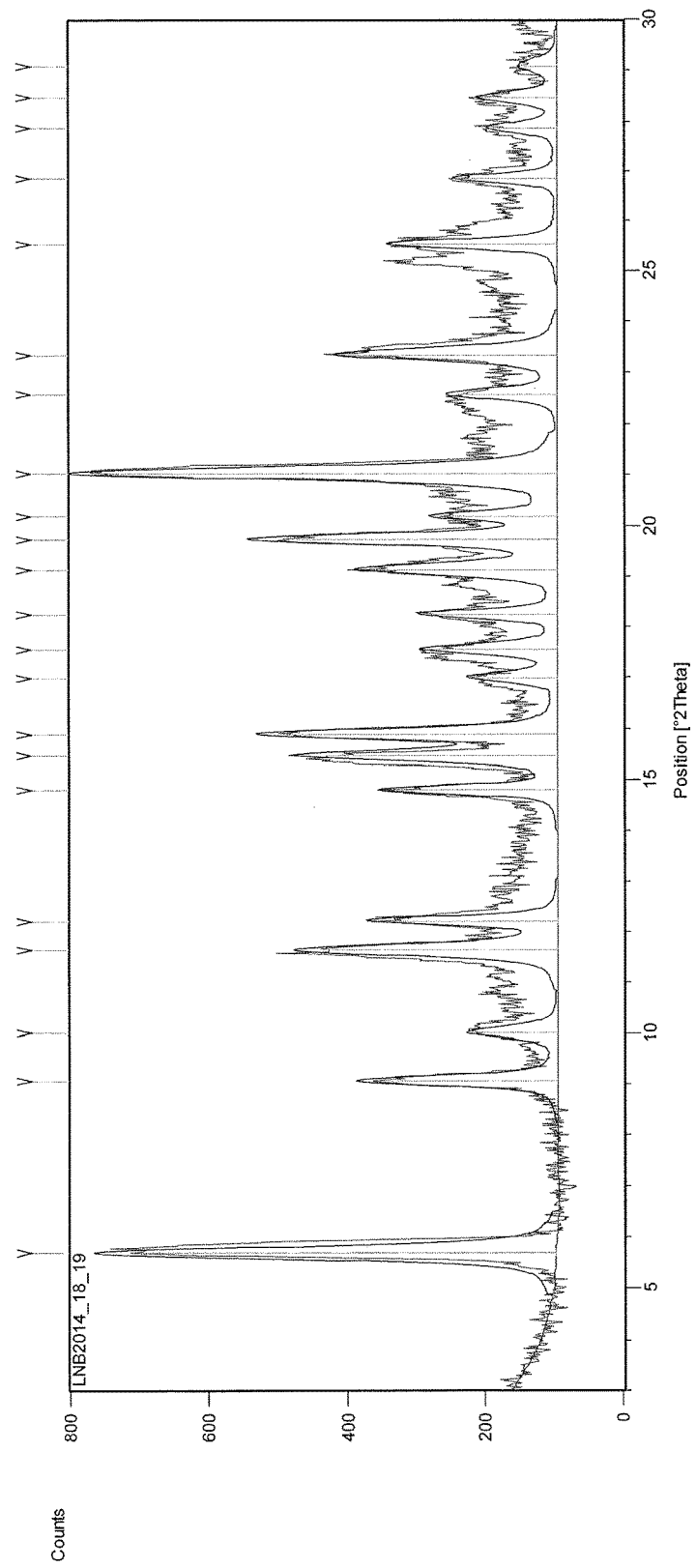
FIG. 10E shows an XRPD spectrum of a sample of the Form A polymorph of Formula II with peaks picked.

A pair of HPLC plots is shown in FIG. 9. As shown in FIG. 9 and Table 11, the following peaks were seen using HPLC analysis, demonstrating that the fumagill-6-yl N-(trans-4-aminocyclohexyl)carbamate benzenesulfonic acid salt was greater than 99% pure.

TABLE 11

HPLC Peaks for Formula I

| Peak No. | RT (min) | Type | Area | Area % | Symmetry |
|---|---|---|---|---|---|
| 1 | 8.749 | MM | 1.11855 × 10$^4$ | 99.350 | 0.666 |
| 2 | 9.932 | MM | 8.80503 | 0.078 | 0.294 |
| 3 | 16.502 | MF | 20.77493 | 0.185 | 0.353 |
| 4 | 17.469 | MM | 38.02194 | 0.338 | 0.296 |
| 5 | 18.169 | MM | 5.58436 | 0.050 | 0.432 |

In one or more embodiments, the salts (i.e., the benzenesulfonic acid salt of fumagill-6-yl N-(trans-4-aminocyclohexyl)carbamate) and polymorphs of the present application (e.g., Form II) have a purity of greater than about 90% (e.g., greater than about 91%, about 92%, about 93%, about 94%, about 95%, about 96%, about 97%, about 98%, about 99%, about 99.5%, about 99.9%, or about 99.99%). In one or more embodiments, the salts (i.e., the benzenesulfonic acid salt of fumagill-6-yl N-(trans-4-aminocyclohexyl)carbamate) and the polymorphs of the present application (e.g., Form II) have a purity of greater than about 95%. In one or more embodiments, the salts (i.e., the benzenesulfonic acid salt of fumagill-6-yl N-(trans-4-aminocyclohexyl)carbamate) and the polymorphs of the present application (e.g., Form II) have a purity of greater than about 97%. In one or more embodiments, the salts (i.e., the benzenesulfonic acid salt of fumagill-6-yl N-(trans-4-aminocyclohexyl)carbamate) and the polymorphs of the present application (e.g., Form II) have a purity of greater than about 98%. In one or more embodiments, the salts (i.e., the benzenesulfonic acid salt of fumagill-6-yl N-(trans-4-aminocyclohexyl)carbamate) and the polymorphs of the present application (e.g., Form II) have a purity of greater than about 99% (e.g., about 99.1%, 99.2%, 99.3%, 99.4%, 99.5%, 99.6%, 99.7%, 99.8%, or 99.9%).

In one or more embodiments, the salts (i.e., the benzenesulfonic acid salt of fumagill-6-yl N-(trans-4-aminocyclohexyl)carbamate) and the polymorphs of the present application (e.g., Form II) comprise less than 0.5% aminocyclohexyl impurities. In one or more embodiments, the salts (i.e., the benzenesulfonic acid salt of fumagill-6-yl N-(trans-4-aminocyclohexyl)carbamate) and the polymorphs of the present application (e.g., Form II) comprise less than 0.4%, less than 0.3%, less than 0.2%, or less than 0.1% aminocyclohexyl impurities.

Formula II: Fumagill-6-yl N-(trans-4-aminocyclohexyl)carbamate Hydroxynaphthoic Acid Salt In some embodiments, the present disclosure provides for a polymorph of fumagill-6-yl N-(trans-4-aminocyclohexyl)carbamate hydroxynaphthoic acid salt.

Form A, Formula II

Form A of fumagill-6-yl N-(trans-4-aminocyclohexyl)carbamate hydroxynaphthoic acid salt can be crystallized from a number of solvents. These solvents include but are not limited to acetonitrile, ethyl acetate, methyl ethyl ketone, and tetrahydrofuran.

In one aspect, the present disclosure provides a polymorph (Form A) of fumagill-6-yl N-(trans-4-aminocyclohexyl)carbamate hydroxynaphthoic acid salt (Formula II) that is characterized by an X-ray powder diffraction pattern at about 5.6, 8.9, and 15.4, degrees 2 θ. In one embodiment, the polymorph is further characterized by an X-ray powder diffraction pattern at about 5.6, 8.9, 11.5, 12.1, 15.4, and 20.9 degrees 2 θ. In one embodiment, the polymorph is further characterized by an X-ray powder diffraction pattern at about 5.6, 8.9, 11.5, 12.1, 15.4, 15.9, 19.7, 20.9, and 23.3 degrees 2 θ. In one embodiment, the polymorph is characterized by an X-ray powder diffraction pattern at about 5.6, 8.9, 11.5, 12.1, 14.6, 15.4, 15.9, 17.4, 18.1, 19.7, 20.9, and 23.3 degrees 2 θ. In one embodiment, the polymorph is characterized by an X-ray powder diffraction pattern including peaks as those listed in Table 12 or 13.

In one or more embodiments, Form A of fumagill-6-yl N-(trans-4-aminocyclohexyl)carbamate hydroxynaphthoic acid salt is further characterized by an X-ray diffraction pattern substantially similar to that set forth in any one of FIGS. 10A-10E.

Figure 11:
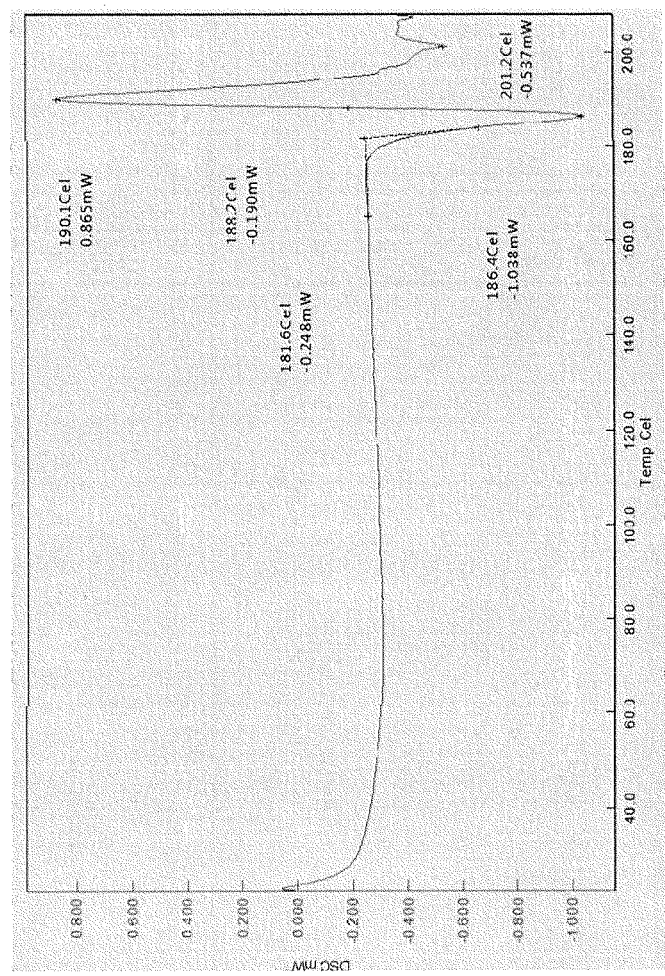
FIG. 11 shows a DSC curve of a sample of the Form A polymorph of Formula II.

In one or more embodiments, Form A of fumagill-6-yl N-(trans-4-aminocyclohexyl)carbamate hydroxynaphthoic acid salt is further characterized by an endothermic onset at about 182° C. and a peak at about 186° C. as measured by DSC. FIG. 11 shows a differential scanning calorimetry curve of a sample of Form A of Formula II.

Figure 12:
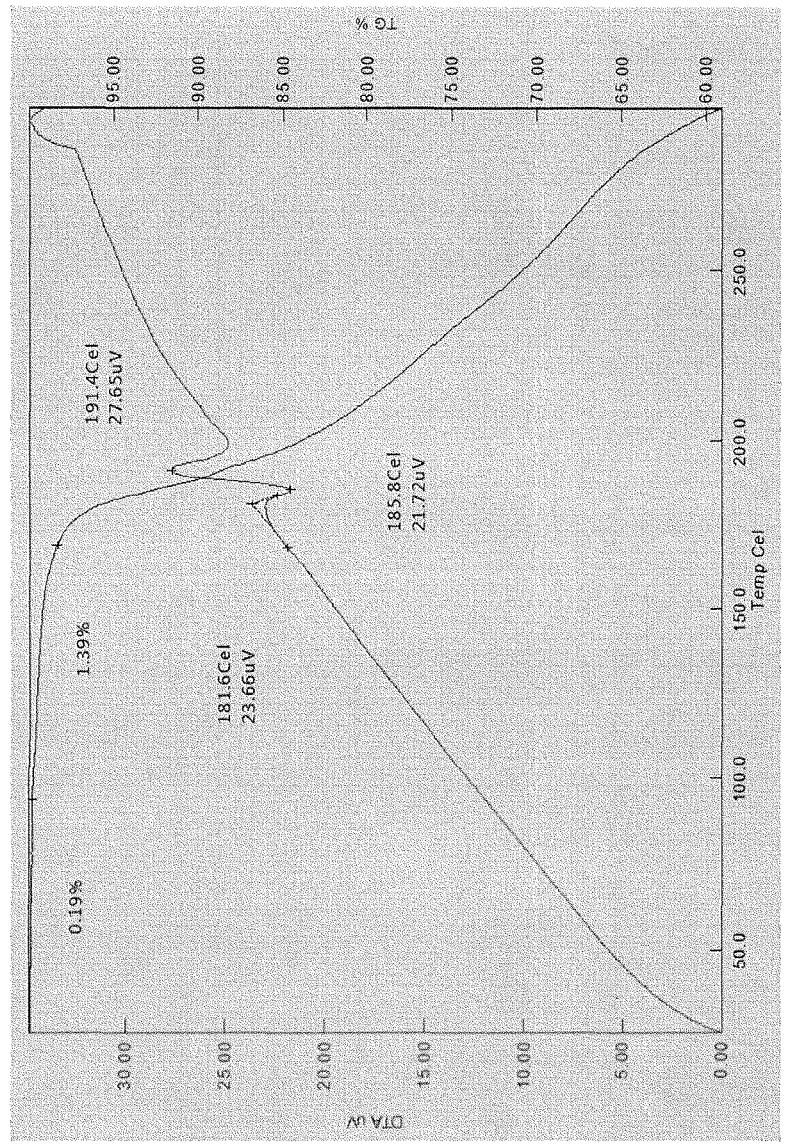
FIG. 12 shows a TG/DTA plot of a sample of the Form A polymorph of Formula II. The TG plot slopes down from left to right, and the DTA plot slopes up from left to right.

In one or more embodiments, Form A of fumagill-6-yl N-(trans-4-aminocyclohexyl)carbamate hydroxynaphthoic acid salt is further characterized by an endothermic onset at about 186° C. and a peak at about 187° C. and an exotherm at about 191° C. (peak) as measured by thermogravimetric analysis/differential thermal analysis. FIG. 12 shows a thermogravimetric analysis/differential thermal analysis plot of a sample of Form A of Formula II.

XRPD

TABLE 12

XRPD: Form A, Sample 1

| Pos. [°2Th.] | Height [cts] | Rel. Int. [%] |
|---|---|---|
| 5.6956 | 599.63 | 92.09 |
| 9.0569 | 262.37 | 40.3 |
| 10.0137 | 118.61 | 18.22 |
| 11.6512 | 341.09 | 52.39 |
| 12.2313 | 242.39 | 37.23 |
| 14.7902 | 232.74 | 35.75 |
| 15.4637 | 336.92 | 51.75 |
| 15.8821 | 386.48 | 59.36 |
| 16.9949 | 116.85 | 17.95 |
| 17.5469 | 179.39 | 27.55 |
| 18.2406 | 185.25 | 28.45 |
| 19.1325 | 261.53 | 40.17 |
| 19.7382 | 403.45 | 61.96 |
| 20.1884 | 157.67 | 24.22 |
| 21.0152 | 651.11 | 100 |
| 22.5661 | 146.19 | 22.45 |
| 23.3409 | 296.97 | 45.61 |
| 25.516 | 238.09 | 36.57 |
| 26.8343 | 146.66 | 22.53 |
| 27.856 | 94.23 | 14.47 |
| 28.4573 | 108.59 | 16.68 |
| 29.0808 | 49.76 | 7.64 |

TABLE 13

XRPD: Form A, Sample 2

| Pos. [°2Th.] | Height [cts] | Rel. Int. [%] |
|---|---|---|
| 5.5828 | 253.59 | 100 |
| 8.8636 | 243.99 | 96.21 |
| 11.4267 | 138.44 | 54.59 |
| 12.0735 | 144.39 | 56.94 |
| 14.5046 | 46.24 | 18.24 |
| 15.2983 | 28.62 | 11.29 |
| 17.3229 | 32.59 | 12.85 |
| 18.0214 | 65.49 | 25.83 |
| 18.9576 | 107.63 | 42.44 |
| 19.678 | 46.2 | 18.22 |
| 20.868 | 122.31 | 48.23 |
| 22.2225 | 21.72 | 8.56 |
| 23.2571 | 57.8 | 22.79 |
| 24.4664 | 12.31 | 4.86 |
| 25.2213 | 30.75 | 12.12 |
| 26.6598 | 13.23 | 5.22 |
| 28.086 | 5.49 | 2.16 |

Figure 13:
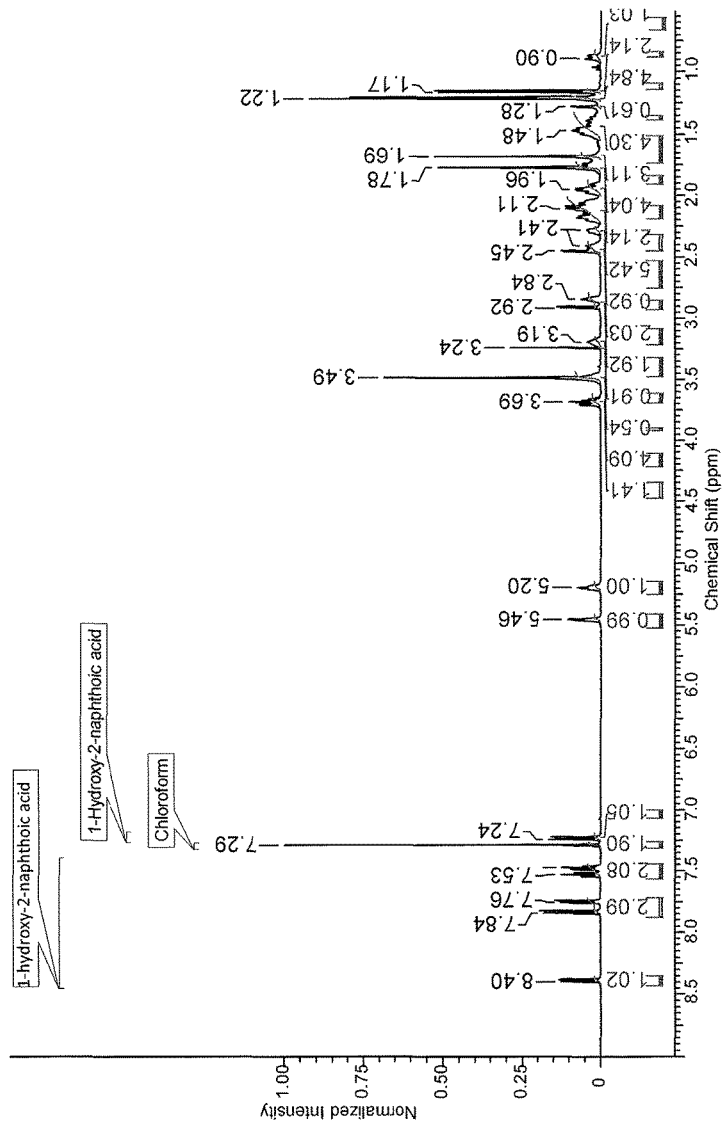
FIG. 13 shows a $^1$H NMR spectrum of Formula II.

In one or more embodiments, the compound of Formula II can have a $^1$H NMR spectrum as shown in FIG. 13. In some embodiments, the compound of Formula II can have a $^1$H NMR spectrum as set forth below:

$^1$H NMR (500 MHz, CDCl$_3$) δ 8.39 (1H, d, J=8.2 Hz, ArH), 7.83 (1H, d, J=8.8 Hz, ArH), 7.76 (1H, d, J=8.2 Hz, ArH), 7.54-7.46 (2H, td, J=27.2 7.3 Hz), 7.23 (1H, d, J=8.5 Hz), 5.45 (1H. br s), 5.19 (1H, t, J=6.8 Hz, CH), 3.69 (1H, dd, J=11.7 2.2 Hz, CH), 3.48 (3H, s, OCH$_3$), 3.19 (1H, t, J=10.9 Hz), 2.91 (1H, d, J=3.8 Hz), 2.84 (1H, t, J=6.3 Hz), 2.46 (1H, d, J=4.1 Hz, CH), 2.42 (1H, t, J=7.9 Hz), 2.29 (1H, d, J=9.8 Hz), 2.20-2.03 (7H, m), 1.98-1.91 (2H, m), 1.77 (3H, s, =CCH$_3$), 1.68 (3H, s, =CCH$_3$), 1.52-1.36 (4H, m), 1.20 (3H, s, CCH$_3$), 0.88 (1H, d, J=13.2 Hz).

Figure 14A:
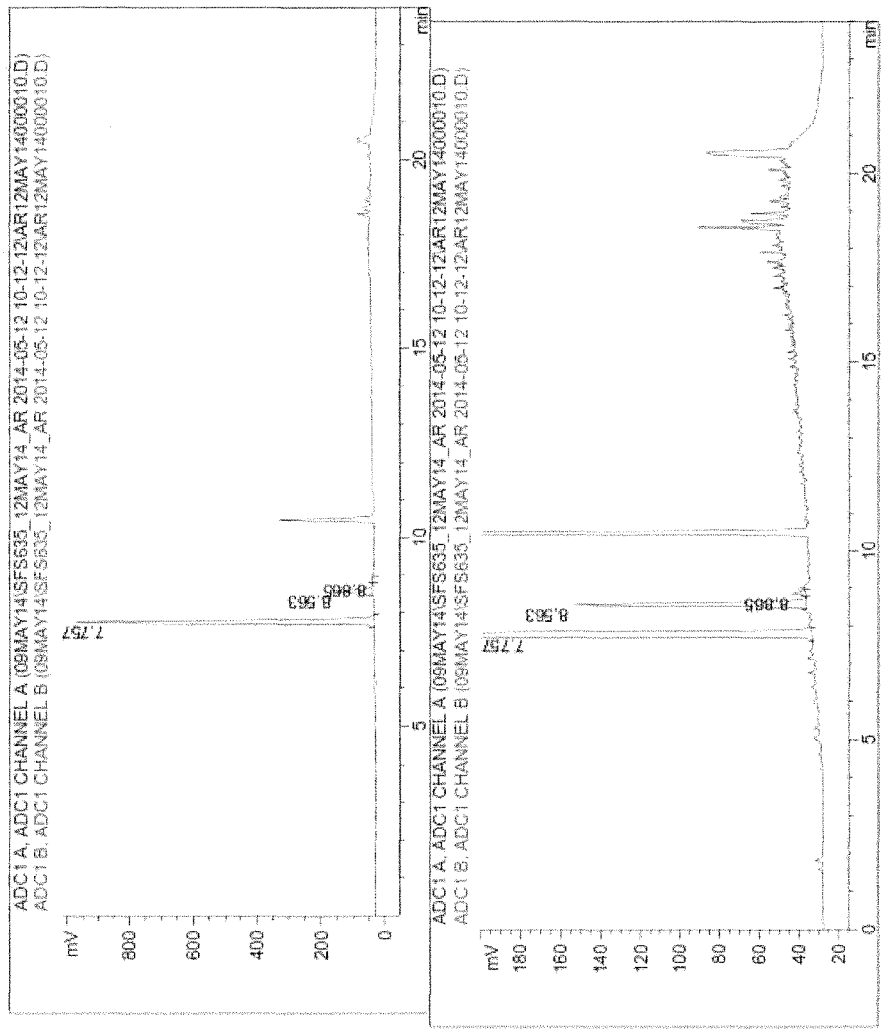
FIG. 14A shows an HPLC analysis of hydroxynaphthoate salt of fumagill-6-yl N-(trans-4-aminocyclohexyl)carbamate (Formula II) taken from the mother liquor. Shown is the same plot at lower (top) and higher resolution (bottom).
Figure 14B:
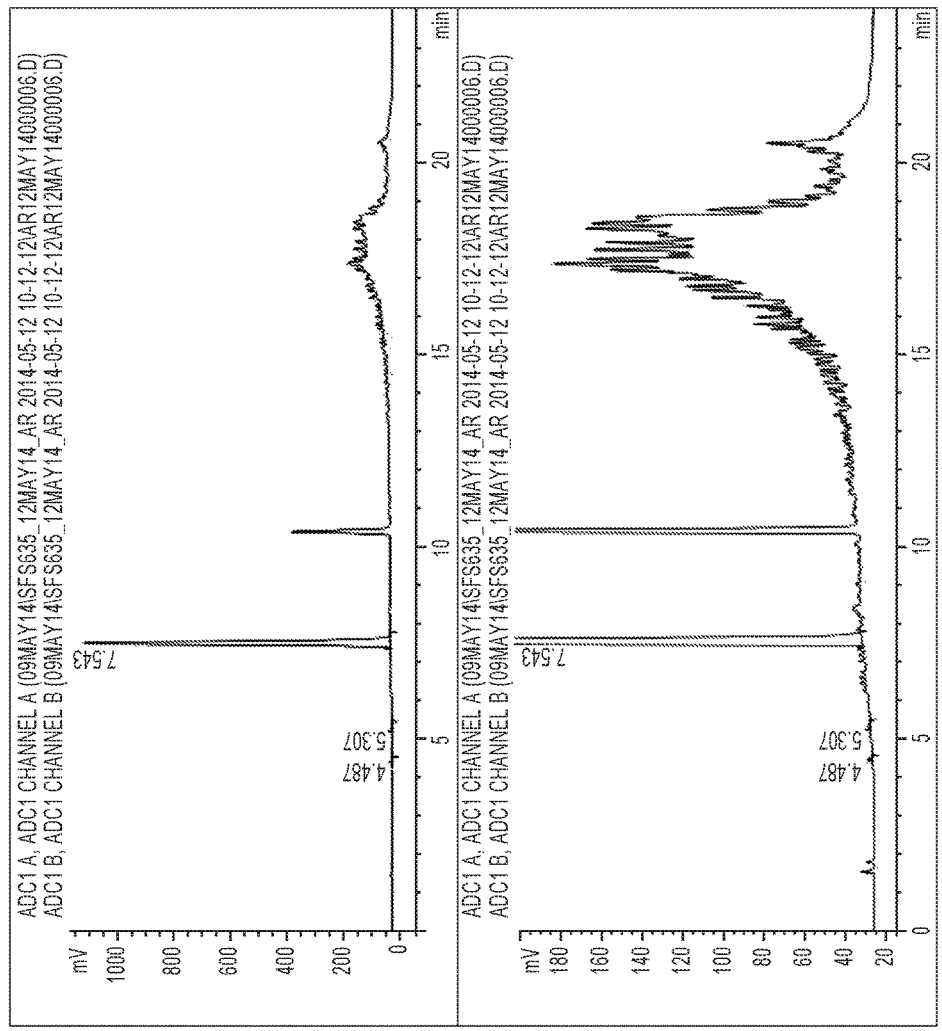
FIG. 14B shows an HPLC analysis of hydroxynaphthoate salt of fumagill-6-yl N-(trans-4-aminocyclohexyl)carbamate (Formula II) taken from solid compound. Shown is the same plot at lower (top) and higher resolution (bottom).

In one or more embodiments, the compound of Formula II can have an HPLC plots as given in FIG. 14A and FIG. 14B. As set forth in FIG. 14A, the top plot is a low-resolution plot of the mother liquor, whereas the lower plot shows the same analysis at a higher resolution. The peaks corresponding to FIG. 14A are given below in Table 14A. As set forth in FIG. 14B, the top plot is a low-resolution plot of solid Formula II product, whereas the lower plot shows the same analysis at higher resolution. The peaks corresponding to FIG. 14B are given below in Table 14B.

TABLE 14A

HPLC Peaks for Formula II - Mother Liquor

| Peak No. | RT (min) | Type | Area | Area % | Symmetry |
|---|---|---|---|---|---|
| 1 | 7.757 | MM | 5403.40820 | 88.086 | 0.763 |
| 2 | 8.563 | MM | 698.02496 | 11.379 | 0.715 |
| 3 | 8.865 | MM | 32.83583 | 0.535 | 0.862 |

TABLE 14B

HPLC Peaks for Formula II - Solid Product

| Peak No. | RT (min) | Type | Area | Area % | Symmetry |
|---|---|---|---|---|---|
| 1 | 4.487 | MM | 6.63760 | 0.082 | 0.457 |
| 2 | 5.307 | MM | 9.91478 | 0.122 | 0.242 |
| 3 | 7.543 | MM | 8111.79004 | 99.796 | 0.942 |

In one or more embodiments, the salts presented herein (i.e., the benzenesulfonic and hydroxynaphthoic acid salts of fumagill-6-yl N-(trans-4-aminocyclohexyl)carbamate) and the polymorphs of the present application (e.g., Form II and Form A) comprise less than 0.5% of the following Compound 2:

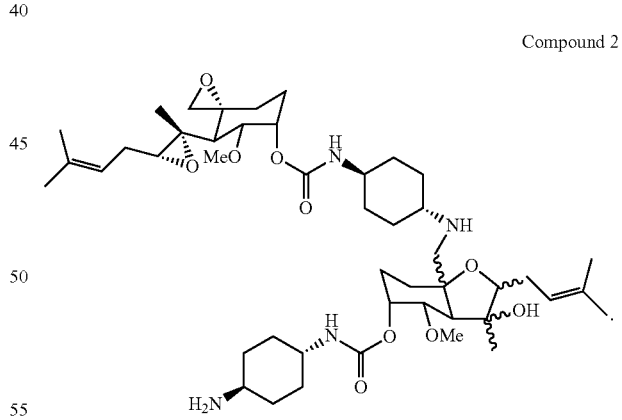

Compound 2

In one or more embodiments, the salts (i.e., the benzenesulfonic acid salt of fumagill-6-yl N-(trans-4-aminocyclohexyl)carbamate) and the polymorphs of the present application (e.g., Form II) comprise less than 0.4%, less than 0.3%, less than 0.2%, or less than 0.1% Compound 2.

In one or more embodiments, the salts (i.e., the benzenesulfonic acid salt of fumagill-6-yl N-(trans-4-aminocyclohexyl)carbamate) and the polymorphs of the present application (e.g., Form II and Form A) comprise less than 0.5% of the following Compound 3:

Compound 3

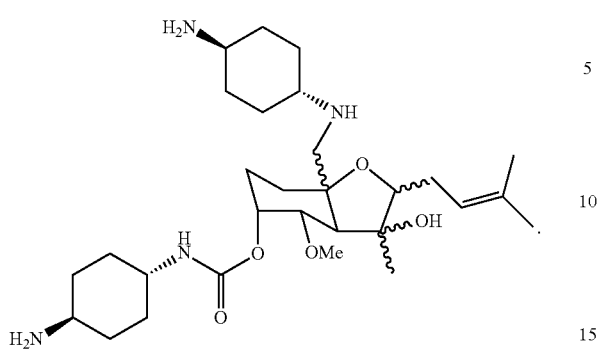

In one or more embodiments, the salts (i.e., the benzenesulfonic acid salt of fumagill-6-yl N-(trans-4-aminocyclohexyl)carbamate) and the polymorphs of the present application (e.g., Form II) comprise less than 0.4%, less than 0.3%, less than 0.2%, or less than 0.1% Compound 3.

In one or more embodiments, the salts (i.e., the benzenesulfonic acid salt of fumagill-6-yl N-(trans-4-aminocyclohexyl)carbamate) and the polymorphs of the present application (e.g., Form II and Form A) comprise less than 0.5% of the following Compound 4:

Compound 4

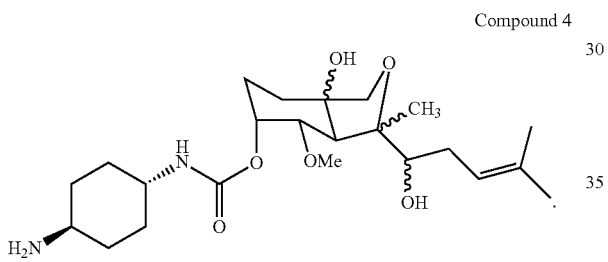

In one or more embodiments, the salts (i.e., the benzenesulfonic acid salt of fumagill-6-yl N-(trans-4-aminocyclohexyl)carbamate) and the polymorphs of the present application (e.g., Form II) comprise less than 0.4%, less than 0.3%, less than 0.2%, or less than 0.1% Compound 4.

In one or more embodiments, the salts (i.e., the benzenesulfonic acid salt of fumagill-6-yl N-(trans-4-aminocyclohexyl)carbamate) and the polymorphs of the present application (e.g., Form II and Form A) comprise less than 0.5% of the following Compound 5:

Compound 5

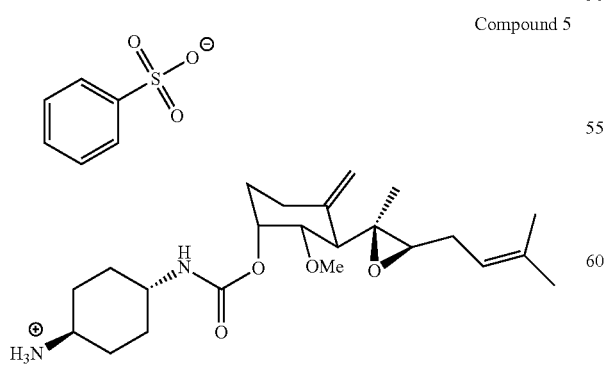

In one or more embodiments, the salts (e.g., the benzenesulfonic acid salt of fumagill-6-yl N-(trans-4-aminocyclohexyl)carbamate) and the polymorphs of the present application (e.g., Form II) comprise less than 0.4%, less than 0.3%, less than 0.2%, or less than 0.1% Compound 5.

In one or more embodiments, the salts (i.e., the benzenesulfonic acid salt of fumagill-6-yl N-(trans-4-aminocyclohexyl)carbamate) and the polymorphs of the present application (e.g., Form II and Form A) comprise less than 0.5% of the following Compound 6:

Compound 6

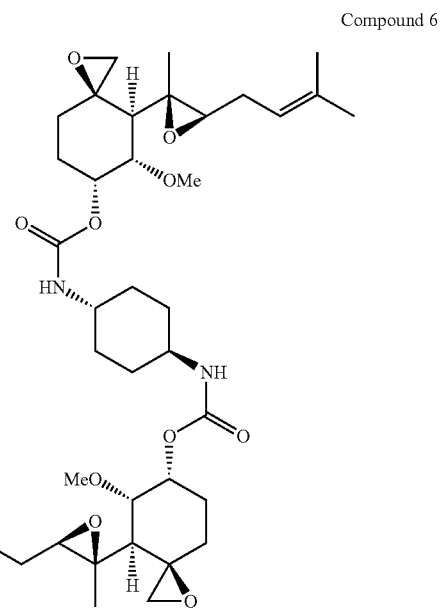

In one or more embodiments, the salts (e.g., the benzenesulfonic acid salt of fumagill-6-yl N-(trans-4-aminocyclohexyl)carbamate) and the polymorphs of the present application (e.g., Form II) comprise less than 0.4%, less than 0.3%, less than 0.2%, or less than 0.1% Compound 6.

In some embodiments, the salts (i.e., the benzenesulfonic acid salt of fumagill-6-yl N-(trans-4-aminocyclohexyl)carbamate) and the polymorphs (e.g., Form II and Form A) of the present application are highly stable. Stability as defined herein is understood as the ability of a compound to maintain a certain, preferably high level of purity for an extended period of time. In some embodiments, stability can be defined as remaining greater than 95% pure for at least six months. In some embodiments, the polymorphs of the present application can retain their purity for long periods of time and even at elevated temperatures and/or relative humidity. In some embodiments, the polymorphs of the present application can retain their purity for over 1 month, 2 months, 3 months, or 6 months at elevated temperatures (e.g., greater than 25° C., greater than 30° C., or greater than 35° C.) and/or elevated relative humidity (e.g., greater than 50% RH, greater than 60% RH, greater than 75% RH, or greater than 90% RH). In some embodiments, the compounds of the disclosure (e.g., Form II of Formula I and Form A of Formula II) can also retain their purity for extended periods at lower temperatures. For example, the compounds of the disclosure can retain purity for 6 months or more at about −20° C.; or for 6 months or more at about 0-5° C.

In some embodiments, the polymorphs of the present application can retain their purity for at least 1 month; at least 2 months; at least 3 months; at least 4 months; at least 5 months; at least 6 months; at least a year; and at least 2 years. In some embodiments, the polymorphs of the present application can retain their purity at temperatures of about 25° C.; about 30° C.; about 35° C.; about 40° C.; about 45° C.; and about 50° C. In some embodiments, the polymorphs of the present invention can retain their purity at about 60% relative humidity; about 65% relative humidity; about 70% relative humidity; about 75% relative humidity; about 80% relative humidity; about 85% relative humidity; about 90% relative humidity; about 90% relative humidity; about 95% relative humidity; and about 100% relative humidity.

In some embodiments, the compounds of the present disclosure are stable at about 5° C.±3° C., about 25° C.±2° C. and 60% relative humidity±5% relative humidity, about 30° C.±2° C. and 65% relative humidity±5% relative humidity, and about 40° C.±2° C. and 75% relative humidity±5% relative humidity.

Table 15 below shows purity data for Form II of Formula I after being kept at 25° C., 60% relative humidity, for six months and Table 16 below shows purity data for Form II of Formula I after being kept at 40° C., 75% relative humidity for six months. As shown below, the compounds can remain >99% pure after being held at 25° C. and 60% relative humidity for six months. The compounds can remain >95% pure after being held at 40° C. and 75% relative humidity for six months.

Methods of Preparing the Polymorphs

The Form II polymorph of Formula I can be prepared by recrystallizing fumagill-6-yl N-(trans-4-aminocyclohexyl) carbamate benzenesulfonic acid salt from a number of different solvents. In some preferred embodiments, the Form II polymorph is prepared from a mixture of MTBE and/or methanol. In some embodiments, the ratio of MTBE to methanol is 50:50. Two methods of recrystallizing fumagill-6-yl N-(trans-4-aminocyclohexyl)carbamate benzenesulfonic acid salt to produce the Form II polymorph are given below.

In any of the embodiments set forth below, the ratio of methanol to methyl tert-butyl ether can be any ratio between 1:99 and 99:1. In any of the embodiments set forth below, Step 1 can take place at any temperature (e.g., between about 25° C. and about 60° C.; or between about 40° C. and about 60° C.). In any of the embodiments below, step 1 Å can comprise cooling the solution to about 25° C. (e.g., from a temperature of about 40° C.). In some embodiments, step 1 Å can comprise cooling the solution to between about 0° C. and 10° C. (e.g., about 2° C. to about 8° C.). In some embodiments, step 2 Å can comprise further cooling the solution. For instance, the solution can be cooled to about 25° C. in step 1 Å and further cooled to about 2° C. to about

TABLE 15

Stability of Form II of Formula I, 25° C., 60% RH

| | 0 Months | 1 Month | 2 Months | 3 Months | 6 months |
|---|---|---|---|---|---|
| Appearance | White powder, visually free of contamination | White powder, visually free of contamination | White powder, visually free of contamination | White powder, visually free of contamination | White powder, visually free of contamination |
| Water Content | 0.41% | 0.60% | 0.57% | 1.73% | 1.58% |
| Largest individual unknown impurity | <0.1% | <0.1% | <0.1% | <0.1% | <0.1% |
| Impurity Compound 4 | <0.1% | ND | 0.1% | 0.1% | 0.1% |
| Impurity Compound 2 | <0.1% | 0.3% | 0.4% | 0.5% | 0.6% |
| Impurity Compound 5 | 0.1% | 0.1% | 0.1% | 0.1% | 0.1% |
| Total Impurities | 0.1% | 0.5% | 0.5% | 0.7% | 0.9% |

TABLE 16

Stability of Form II of Formula I, 40° C., 75% RH

| | 0 Months | 1 Month | 2 Months | 3 Months | 6 months |
|---|---|---|---|---|---|
| Appearance | White powder, visually free of contamination | White powder, visually free of contamination | White powder, visually free of contamination | White powder, visually free of contamination | White powder, visually free of contamination |
| Water Content | 0.41% | 1.54% | 1.19% | 2.57% | 3.19% |
| Largest individual unknown impurity | <0.1% | 0.2% | 0.3% | 0.4% | 0.3% |
| Impurity Compound 4 | <0.1% | ND | 0.3% | 0.5% | 1.4% |
| Impurity Compound 2 | <0.1% | 1.0% | 1.4% | 1.6% | 1.5% |
| Impurity Compound 5 | 0.1% | 0.1% | 0.1% | 0.2% | 0.5% |
| Total Impurities | 0.1% | 1.5% | 2.4% | 3.1% | 4.2% |

8° C. in step 2A. In some embodiments, Step 1 Å is omitted and Step 2 Å can comprise cooling the solution from about 40° to about 25° C. or to between about 2° C. and 8° C.

In some embodiments, the present disclosure provides a method for preparing a polymorph (e.g., Form II) of fumagill-6-yl N-(trans-4-aminocyclohexyl)carbamate benzenesulfonic acid salt (Formula I) comprising:
(i) Step 1: dissolving fumagill-6-yl N-(trans-4-aminocyclohexyl)carbamate benzenesulfonic acid salt in methanol, optionally containing MTBE, to form a solution;
(ii) Step 2: optionally adding a seed crystal (e.g., about 1 weight percent) of fumagill-6-yl N-(trans-4-aminocyclohexyl)carbamate benzenesulfonic acid salt to the solution;
(iii) Step 3: optionally separating the crystallized fumagill-6-yl N-(trans-4-aminocyclohexyl)carbamate benzenesulfonic acid salt from the solution.

In some embodiments, the method further comprises the optional Steps 1 Å and/or 1B after Step 1 but before Step 2:
Step 1A: cooling the solution of fumagill-6-yl N-(trans-4-aminocyclohexyl)carbamate benzenesulfonic acid salt from the previous step;
Step 1B: adding additional MTBE to the solution of fumagill-6-yl N-(trans-4-aminocyclohexyl)carbamate benzenesulfonic acid salt from the previous step.

In some embodiments, the method further comprises the optional Steps 2 Å and/or 2B after Step 2 but before optional Step 3:
Step 2A: cooling the solution of fumagill-6-yl N-(trans-4-aminocyclohexyl)carbamate benzenesulfonic acid salt from the previous step;
Step 2B: adding MTBE to the solution of fumagill-6-yl N-(trans-4-aminocyclohexyl)carbamate benzenesulfonic acid salt from the previous step.

In one embodiment, Step 1 is conducted at ambient temperature or room temperature (e.g., from about 20° C. to about 25° C.). In one embodiment, Step 1 comprises warming (e.g., to about 38-50° C., or to about 40° C.) the fumagill-6-yl N-(trans-4-aminocyclohexyl)carbamate benzenesulfonic acid salt in methanol, optionally containing MTBE, to facilitate the dissolution.

A polymorph of fumagill-6-yl N-(trans-4-aminocyclohexyl)carbamate benzenesulfonic acid salt (Formula I) can be prepared by performing steps 1, 2 and 3 and any combination of steps 1A, 1B, 2A and 2B, as described above.

In one embodiment, the present disclosure provides a method for preparing a polymorph of fumagill-6-yl N-(trans-4-aminocyclohexyl)carbamate benzenesulfonic acid salt (e.g., Form II), comprising:
(1) adding fumagill-6-yl N-(trans-4-aminocyclohexyl)carbamate benzenesulfonic acid salt to a volume of methanol to form a solution;
(1B) adding a volume of tert-butyl methyl ether to the solution;
(1A) cooling the solution;
(2) adding a seed crystal (e.g., about 1 weight percent) of fumagill-6-yl N-(trans-4-aminocyclohexyl)carbamate benzenesulfonic acid salt to the solution;
(2A) cooling the solution;
(2B) adding additional tert-butyl methyl ether to the solution to produce a crystalline form of fumagill-6-yl N-(trans-4-aminocyclohexyl)carbamate benzenesulfonic acid salt; and
(3) filtering the solution to isolate the crystalline fumagill-6-yl N-(trans-4-aminocyclohexyl)carbamate benzenesulfonic acid salt.

In one or more embodiments of any of the above-aspects, the ratio between the methanol and fumagill-6-yl N-(trans-4-aminocyclohexyl)carbamate benzenesulfonic acid salt in step (1) is about 5:3 (liter/mol). In one or more embodiments, about 1 liter of methanol is used to dissolve about 0.6 mol of fumagill-6-yl N-(trans-4-aminocyclohexyl)carbamate benzenesulfonic acid salt in step (i). In one or more embodiments of the above-method, the mixture in step (1) is warmed to about 38-50° C. to form a solution. In one or more embodiments of any of the above-methods, the mixture in step (1) is warmed, e.g., to about 40° C., to form a solution.

In one or more embodiments, the volume of tert-butyl methyl ether added in step (1B) is about 1-1.5 times the volume of methanol used in step (1). In one or more embodiments, the volume of tert-butyl methyl ether added in step (1B) is about 1.25 times the volume of methanol used in step (1). In one or more embodiments, the solution becomes cloudy after the addition of tert-butyl methyl ether.

In one or more embodiments, step (1A) comprises cooling the solution to about 30-36° C. In one or more embodiments, step (1A) comprises cooling the solution to about 35° C. In one or more embodiments, the cooling in step (1A) is conducted slowly. In one or more embodiments, the cooling is completed in about an hour.

In one or more embodiments, the seed crystal (e.g., about 1 weight percent) of fumagill-6-yl N-(trans-4 aminocyclohexyl)carbamate benzenesulfonic acid salt added in step (2) is ground before it is added.

In one or more embodiments, step (2A) comprises cooling the solution to about 2-8° C. In one or more embodiments, step (2A) further comprises maintaining the temperature of the solution (i.e., at about 2-8° C.) for a period of time (e.g., about 5-20 minutes). In one or more embodiments, step (2A) further comprises maintaining the temperature of the solution (i.e., at about 2-8° C.) for about 10 minutes.

In one or more embodiments, the volume of additional tert-butyl methyl ether added in step (2B) is about 4-8 times the volume of methanol used in step (1). In one or more embodiments, the volume of additional tert-butyl methyl ether added in step (2B) is about 6.5 times the volume of methanol used in step (1). In one or more embodiments, the temperature in step (2B) is maintained at about 2-8° C. In one or more embodiments, the temperature in step (2B) is maintained at about 2-8° C. for a period of time (e.g., about an hour).

In one or more embodiments, the crystalline form of fumagill-6-yl N-(trans-4-aminocyclohexyl)carbamate benzenesulfonic acid salt is further washed with tert-butyl methyl ether after step (3). In one or more embodiments, the crystalline form of fumagill-6-yl N-(trans-4-aminocyclohexyl)carbamate benzenesulfonic acid salt can be further dried in vacuo. In one or more embodiments, the crystalline form of fumagill-6-yl N-(trans-4-aminocyclohexyl)carbamate benzenesulfonic acid salt can be further dried in vacuo at about 40° C.

In one or more embodiments, application of the steps provided herein, or a combination thereof for the formation of Form II and Form A (e.g., Step 1, Step 1', Step 1A, Step 1B, Step 2, Step 2A, Step 2B, Step 3) can result in increased purity and or increased yield. In some embodiments, application of the steps provided herein can improve the yield over simply applying Steps 1, 2 and 3. For instance, application of the steps herein can improve the yield by about 10%, about 20%, about 30%, about 40%, about 50%, about 60%, about 70%, about 80%, about 90%, or about 100%. The yield of Form II or Form A can be about 80%, about 85%, about 90%, about 95%, about 96%, about 97%, about 98%, about 99%, about 99.5%, or about 99.9% or greater. Additionally, the purity of the Form II or Form A produced can be increased by application of the methods provided herein (e.g., Step 1, Step 1', Step 1A, Step 1B, Step 2, Step 2A, Step 2B, Step 3). In some embodiments, application of the steps provided herein can improve the purity over simply applying Steps 1, 2 and 3. For instance, application of the steps herein can improve the purity by about 10%, about 20%, about 30%, about 40%, about 50%, about 60%, about 70%, about 80%, about 90%, or about 100%. The purity of Form II or Form A can be about 80%, about 85%, about 90%, about 95%, about 96%, about 97%, about 98%, about 99%, about 99.5%, or about 99.9% or greater.

In another embodiment, the present disclosure provides a method for preparing a polymorph of fumagill-6-yl N-(trans-4-aminocyclohexyl)carbamate benzenesulfonic acid salt (e.g., Form II), comprising:

(1) dissolving fumagill-6-yl N-(trans-4-aminocyclohexyl) carbamate benzenesulfonic acid salt in a mixture of tert-butyl methyl ether and methanol to form a solution;

(1A) cooling the solution;

(2) adding a seed crystal (e.g., about 1 weight percent) of fumagill-6-yl N-(trans-4-aminocyclohexyl)carbamate benzenesulfonic acid salt to the solution;

(2A) continuing to cool the solution;

(2B) adding an additional amount of tert-butyl methyl ether to the solution to produce a crystalline form of fumagill-6-yl N-(trans-4-aminocyclohexyl)carbamate benzenesulfonic acid salt; and (3) filtering the solution to isolate the crystalline form of fumagill-6-yl N-(trans-4-aminocyclohexyl)carbamate benzenesulfonic acid salt.

In one or more embodiments, the ratio of tert-butyl methyl ether and methanol in step (1) is between about 50:50 and about 20:80. In one or more embodiments, the ratio is about 50:50. In one or more embodiments, the dissolution is conducted at about 40-60° C. In one or more embodiments, the dissolution is conducted at about 50° C. In one or more embodiments, the solution of fumagill-6-yl N-(trans-4-aminocyclohexyl)carbamate benzenesulfonic acid salt produced in step (i) is stirred for about 15 minutes to 1 hour. In one or more embodiments, the solution of fumagill-6-yl N-(trans-4-aminocyclohexyl)carbamate benzenesulfonic acid salt produced in step (1) is stirred for about 30 minutes at 50° C. to ensure dissolution prior to cooling.

In one or more embodiments, step (1A) comprises cooling at a rate of about 0.1-0.5° C. per minute. In one or more embodiments, step (1A) comprises cooling at a rate of about 0.2° C. per minute. In one or more embodiments, step (ii) comprises cooling to about 30-45° C. In one or more embodiments, step (1A) comprises cooling to about 37° C.

In one or more embodiments, the seed crystal (e.g., about 1 weight percent) of fumagill-6-yl N-(trans-4 aminocyclohexyl)carbamate benzenesulfonic acid salt added in step (2) is ground before it is added.

In one or more embodiments, step (2A) comprises cooling at a rate of about 0.1-0.5° C. per minute. In one or more embodiments, step (2A) comprises cooling at a rate of about 0.2° C. per minute. In one or more embodiments, step (2A) comprises cooling to below 10° C. In one or more embodiments, step (2A) comprises cooling to about 5° C.

In one or more embodiments, the amount of tert-butyl methyl ether added in step (2B) is about 10-50% of the amount of the mixture of tert-butyl methyl ether and methanol used in step (1). In one or more embodiments, the amount of tert-butyl methyl ether added in step (2B) is about 15% of the amount of the mixture of tert-butyl methyl ether and methanol used in step (1). In one or more embodiments, the amount of tert-butyl methyl ether added in step (2B) is about 30% of the amount of the mixture of tert-butyl methyl ether and methanol used in step (1).

In one or more embodiments, the crystalline form of fumagill-6-yl N-(trans-4-aminocyclohexyl)carbamate benzenesulfonic acid salt is further washed with tert-butyl methyl ether after step (3). In one or more embodiments, the crystalline form of fumagill-6-yl N-(trans-4-aminocyclohexyl)carbamate benzenesulfonic acid salt can be further dried in vacuo. In one or more embodiments, the crystalline form of fumagill-6-yl N-(trans-4-aminocyclohexyl)carbamate benzenesulfonic acid salt can be further dried in vacuo at about 40° C.

In another embodiment, the present disclosure provides a method for preparing a polymorph of fumagill-6-yl N-(trans-4-aminocyclohexyl)carbamate benzenesulfonic acid salt (e.g., Form II), comprising:

(1) dissolving fumagill-6-yl N-(trans-4-aminocyclohexyl) carbamate benzenesulfonic acid salt in a mixture of tert-butyl methyl ether and methanol to form a solution;

(1B) adding tert-butyl methyl ether to the solution;

(2) adding a seed crystal (e.g., about 1 weight percent) of fumagill-6-yl N-(trans-4-aminocyclohexyl)carbamate benzenesulfonic acid salt to the solution;

(2B) adding additional amount of tert-butyl methyl ether to the solution;

(2A) cooling the solution to produce a crystalline form of fumagill-6-yl N-(trans-4-aminocyclohexyl)carbamate benzenesulfonic acid salt; and (3) filtering the solution to separate the crystalline form of fumagill-6-yl N-(trans-4-aminocyclohexyl)carbamate benzenesulfonic acid salt.

In one or more embodiments, the ratio of tert-butyl methyl ether and methanol in step (1) is between about 50:50 and about 20:80. In one or more embodiments, the ratio is about 50:50. In one or more embodiments, the dissolution is conducted at about 40-60° C. In one or more embodiments, the dissolution is conducted at about 50° C. In one or more embodiments, the solution of fumagill-6-yl N-(trans-4-aminocyclohexyl)carbamate benzenesulfonic acid salt produced in step (1) is stirred for about 15 minutes to 1 hour. In one or more embodiments, the solution of fumagill-6-yl N-(trans-4-aminocyclohexyl)carbamate benzenesulfonic acid salt produced in step (1) is stirred for about 30 minutes at 50° C. to ensure dissolution prior to cooling.

In one or more embodiments, the volume of tert-butyl methyl ether added in step (1B) is about 1-1.5 times the volume of methanol used in step (1). In one or more embodiments, the volume of tert-butyl methyl ether added in step (1B) is about 1.25 times the volume of methanol used in step (1). In one or more embodiments, the solution becomes cloudy after the addition of tert-butyl methyl ether.

In one or more embodiments, the seed crystal (e.g., about 1 weight percent) of fumagill-6-yl N-(trans-4 aminocyclohexyl)carbamate benzenesulfonic acid salt added in step (2) is ground before it is added.

In one or more embodiments, the amount of tert-butyl methyl ether added in step (2B) is about 10-50% of the amount of the mixture of tert-butyl methyl ether and methanol used in step (1). In one or more embodiments, the amount of tert-butyl methyl ether added in step (2B) is about 15% of the amount of the mixture of tert-butyl methyl ether and methanol used in step (1). In one or more embodiments, the amount of tert-butyl methyl ether added in step (2B) is about 30% of the amount of the mixture of tert-butyl methyl ether and methanol used in step (1).

In one or more embodiments, step (2A) comprises cooling at a rate of about 0.1-0.5° C. per minute. In one or more embodiments, step (2A) comprises cooling at a rate of about 0.2° C. per minute. In one or more embodiments, step (2A) comprises cooling to below 10° C. In one or more embodiments, step (2A) comprises cooling to about 5° C.

In one or more embodiments, the crystalline form of fumagill-6-yl N-(trans-4-aminocyclohexyl)carbamate benzenesulfonic acid salt is further washed with tert-butyl methyl ether after step (3). In one or more embodiments, the crystalline form of fumagill-6-yl N-(trans-4-aminocyclohexyl)carbamate benzenesulfonic acid salt can be further dried in vacuo. In one or more embodiments, the crystalline form of fumagill-6-yl N-(trans-4-aminocyclohexyl)carbamate benzenesulfonic acid salt can be further dried in vacuo at about 40° C.

Cooling Recrystallization

In some embodiments, the Form II polymorph of fumagill-6-yl N-(trans-4-aminocyclohexyl)carbamate benzenesulfonic acid salt can be crystallized from a mixture of MTBE and methanol by dissolving solid fumagill-6-yl N-(trans-4-aminocyclohexyl)carbamate benzenesulfonic acid salt in MTBE and methanol at about 50° C. and cooling the resulting mixture before adding additional MTBE to the mixture to complete the crystallization. In some embodiments, the mixture of MTBE and methanol is a 50:50 mixture. The ratio of MTBE to methanol can be any ratio between 1:99 and 99:1. In some preferred embodiments, the ratio of MBTE to methanol is less than about 8:2. In some embodiments, the ratio of MBTE to methanol is between about 8:2 and about 9:1. In some embodiments, the purity of the resulting fumagill-6-yl N-(trans-4-aminocyclohexyl)carbamate benzenesulfonic acid salt can be adversely affected if significantly more MBTE is used. In some embodiments, the purity of the resulting fumagill-6-yl N-(trans-4-aminocyclohexyl)carbamate benzenesulfonic acid salt can be adversely affected if the ration of MBTE to methanol is greater than about 9:1. In some embodiments, the fumagill-6-yl N-(trans-4-aminocyclohexyl)carbamate benzenesulfonic acid salt is dissolved at a temperature of about 50° C. The fumagill-6-yl N-(trans-4-aminocyclohexyl)carbamate benzenesulfonic acid salt can also be dissolved at about 40° C., about 35° C., about 25° C., or any specific temperature between 50° and 5° C. XRPD spectra for the material produced by the Cooling Recrystallization procedure are shown in FIG. 3. FIG. 3A shows an XRPD spectrum of material from the first sample (i.e., before addition of further MTBE), and FIG. 3B shows an XRPD spectrum of material from the second sample (i.e., after addition of 30 mL MTBE). FIG. 3C shows an XRPD spectrum of the final dried material.

Antisolvent Recrystallization

In some embodiments, the Form II polymorph of fumagill-6-yl N-(trans-4-aminocyclohexyl)carbamate benzenesulfonic acid salt can be crystallized from a mixture of MTBE and methanol by dissolving solid fumagill-6-yl N-(trans-4-aminocyclohexyl)carbamate benzenesulfonic acid salt in MTBE and methanol at about 50° C. and adding additional MTBE before cooling the resulting mixture to complete the crystallization. The ratio of MTBE to methanol can be any ratio between 1:99 and 99:1. In some embodiments, the fumagill-6-yl N-(trans-4-aminocyclohexyl)carbamate benzenesulfonic acid salt is dissolved at a temperature of about 50° C. The fumagill-6-yl N-(trans-4-aminocyclohexyl)carbamate benzenesulfonic acid salt can also be dissolved at about 40° C., about 35° C., about 25° C., or any specific temperature between 50° and 5° C. XRPD spectra for the material produced by the Antisolvent Recrystallization procedure are shown in FIG. 4. FIG. 4A shows an XRPD spectrum of material from the first sample (i.e., after addition of about 30 mL MTBE), and FIG. 4B shows an XRPD spectrum of material from the second sample (i.e., after addition of 60 mL MTBE). FIG. 4C shows an XRPD spectrum of the final dried material.

Crystallization from Ethyl Acetate

In some embodiments, Formula I and/or Formula II can be crystallized directly from ethyl acetate (e.g., as set forth in Example 5, below). In some embodiments, the crystallization can take place directly from ethyl acetate without first having to acidify the Formula I and/or Formula II free base and extract it into an aqueous layer before basifying the aqueous layer and extracting the free base back into the organic solvent. This can have the advantage of being operationally simpler than recrystallization from methanol and/or tert-butyl methyl ether, and can have the advantage of using less organic solvent while still maintaining purity of the final product (i.e., Formula I and/or Formula II).

Accordingly, in some embodiments, the present disclosure provides a process for preparing a polymorph of fumagill-6-yl N-(trans-4-aminocyclohexyl)carbamate benzenesulfonic acid salt (e.g., Form II), comprising:

(i) dissolving fumagill-6-yl N-(trans-4-aminocyclohexyl) carbamate in ethyl acetate to form a solution;

(ii) adding benzenesulfonic acid to the solution of fumagill-6-yl N-(trans-4-aminocyclohexyl)carbamate in ethyl acetate; and (iii) filtering the resulting fumagill-6-yl N-(trans-4-aminocyclohexyl)carbamate benzenesulfonic acid salt.

In some embodiments, the benzenesulfonic acid is added as a solution in ethyl acetate. In some embodiments, the benzenesulfonic acid is added at a temperature of about 8-12° C. In some embodiments, the method further comprises cooling the mixture of fumagill-6-yl N-(trans-4-aminocyclohexyl)carbamate and benzenesulfonic acid to about 0-5° C. Accordingly, in some embodiments, the crystallization from ethyl acetate is a reactive crystallization. In some embodiments, the water content in the ethyl acetate free base solution before adding the benzenesulfonic acid/ethyl acetate solution is in the range of 1.0-1.3%.

Synthesis of fumagill-6-yl N-(trans-4-aminocyclohexyl)carbamate Benzenesulfonic Acid Salt (Formula I)

fumagill-6-yl N-(trans-4-aminocyclohexyl)carbamate benzenesulfonic acid salt can be prepared from the treatment of fumagill-6-yl, p-nitrophenyl carbonate with an excess of trans-1,4-diaminocyclohexane as shown in Scheme 1, below. The free base product is ultimately extracted into MTBE and treated with benzenesulfonic acid as set forth in Example 1, below.

Scheme 1. Synthesis of fumagill-6-yl N-(trans-4-aminocyclohexyl)carbamate benzenesulfonic acid salt from fumagill-6-yl, p-nitrophenyl carbonate

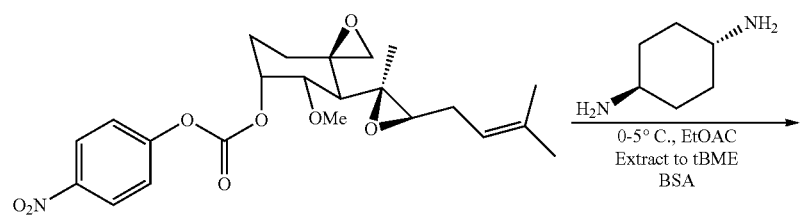

-continued

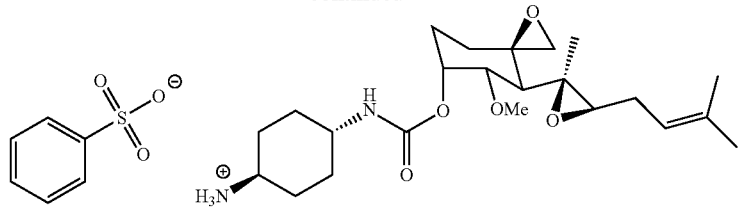

Without wishing to be bound by theory, it was found that the free base form of Formula I, i.e., fumagill-6-yl N-(trans-4-aminocyclohexyl)carbamate, is inherently unstable due to the presence of both a primary amine and two epoxides. Moreover, it was found that the hemi-tartrate version of Formula I (not pictured) contained significant amounts of self-condensation products Compound 2 and Compound 3, as well as the hydrolysis product Compound 4, each shown above. The hemi-tartrate and benzenesulfonic acid salts also contained an impurity related to the fumagillin (natural product) starting material, Compound 5 (shown above). Extensive experimental efforts could not reduce the impurity levels in the hemi-tartrate to pharmaceutically acceptable levels. Accordingly, it is understood that the fumagill-6-yl N-(trans-4-aminocyclohexyl)carbamate benzenesulfonic acid salt and polymorphs thereof of the present disclosure (e.g., Form II) are more stable than the corresponding hemi-tartrate salts and free base.

In contrast to the free base and other salt forms described above, the polymorphs described herein (e.g., Form II) are stable at standard temperature and pressure, for example, as established by the ICH standards for the evaluation of pharmaceutical substances. Accordingly, the polymorphs described herein can be used as robust chemical intermediates as set forth below.

In some embodiments, the present disclosure provides a reactive crystallization of a compound of Formula I from the corresponding free base as described in Example 1 and/or Example 5. This process avoids the isolation of free base epoxide, which can in some embodiments undergo self-condensation.

Use of fumagill-6-yl N-(trans-4-aminocyclohexyl)carbamate benzenesulfonic acid salt fumagill-6-yl N-(trans-4-aminocyclohexyl)carbamate Benzenesulfonic Acid Salt (Formula I) is useful as an intermediate in the synthesis of polymer-conjugated derivatives of fumagillol or fumagillin such as compounds of Formula III:

(Formula III)

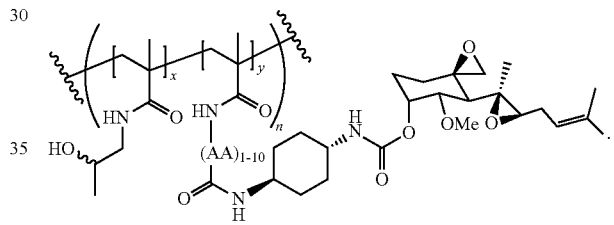

In one aspect, the present disclosure provides a process for making Compound 1:

(Compound 1)

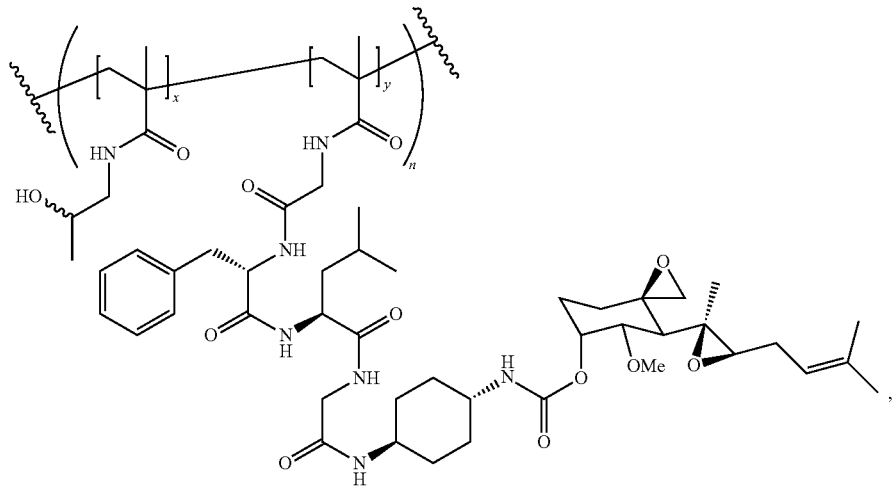

comprising contacting a compound of Formula I or Formula II:

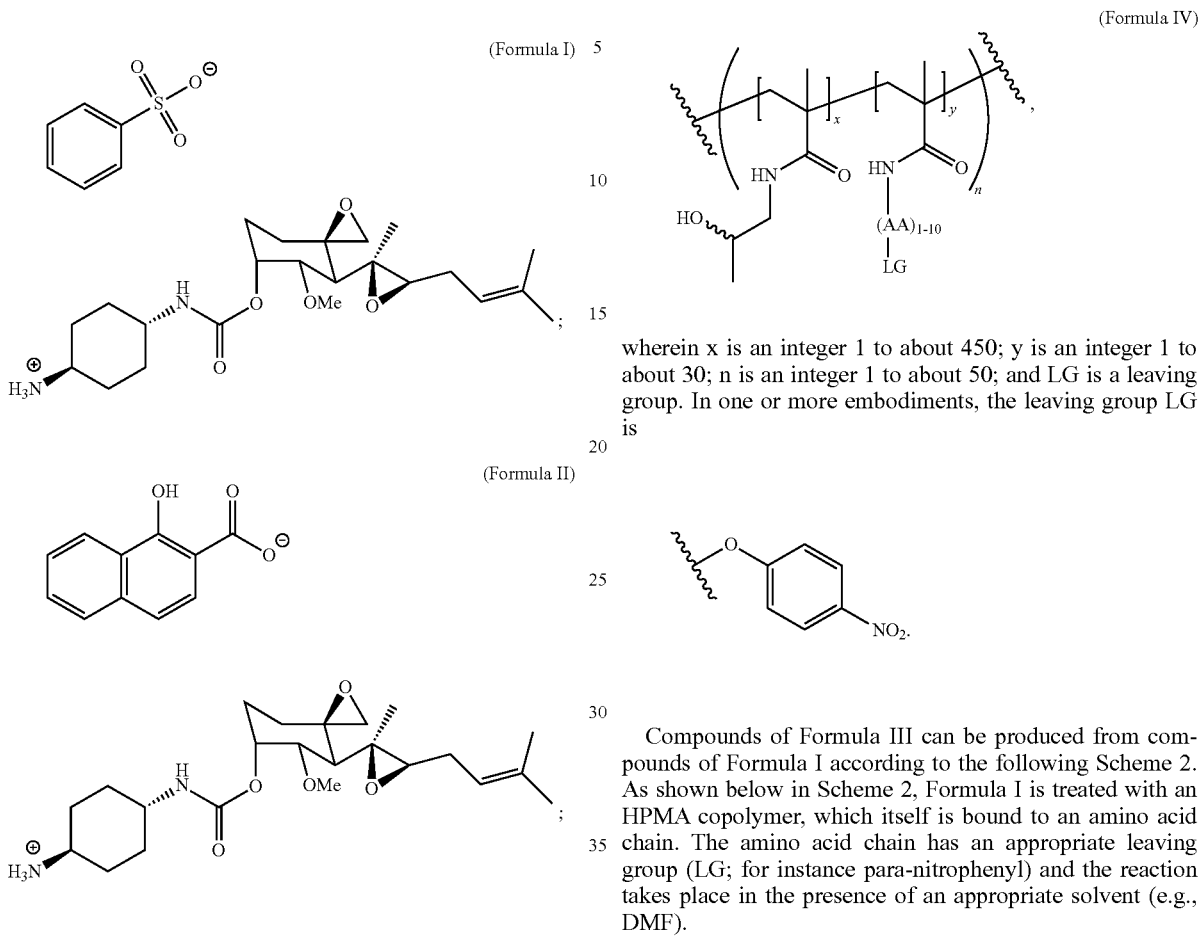

wherein x is an integer 1 to about 450; y is an integer 1 to about 30; n is an integer 1 to about 50; and LG is a leaving group. In one or more embodiments, the leaving group LG is Compounds of Formula III can be produced from compounds of Formula I according to the following Scheme 2. As shown below in Scheme 2, Formula I is treated with an HPMA copolymer, which itself is bound to an amino acid chain. The amino acid chain has an appropriate leaving group (LG; for instance para-nitrophenyl) and the reaction takes place in the presence of an appropriate solvent (e.g., DMF).

Scheme 2. Exemplary Preparation of Compound I of Formula III from Formula I.

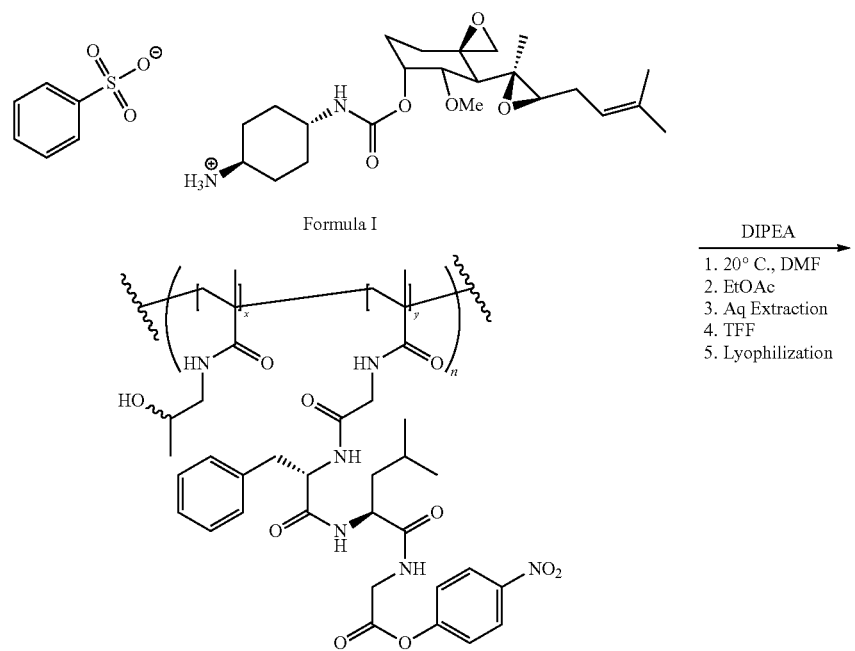

-continued

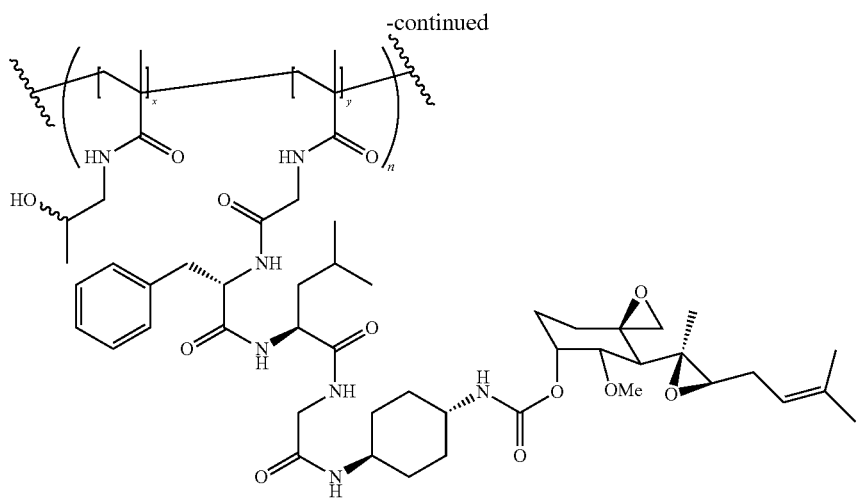

Certain impurities during the synthesis of compounds of Formula I or II, such as Compounds 2, 3, 4 and 5, as described above, can also react in the same manner as Formula I or II and conjugate to the polymer. This can interfere with the reaction, and also reduce the purity of Formula III because polymer-bound impurities are difficult to remove. The polymorphs of the present application, as shown above, possess high purity, and in particular, comprise minimal amount of Compounds 2, 3, 4 and 5. Accordingly, the polymorphs of the present application are particularly suitable as intermediates for the preparation of compounds of Formula III, and can be used to prepare Formula III in good yield and high purity. Without wishing to be bound by theory, use of a salt presented herein (e.g., Formula I or Formula II) as an intermediate of a compound of Formula III can provide a higher yield and greater purity compared with using the corresponding free base.

Figure 15A:
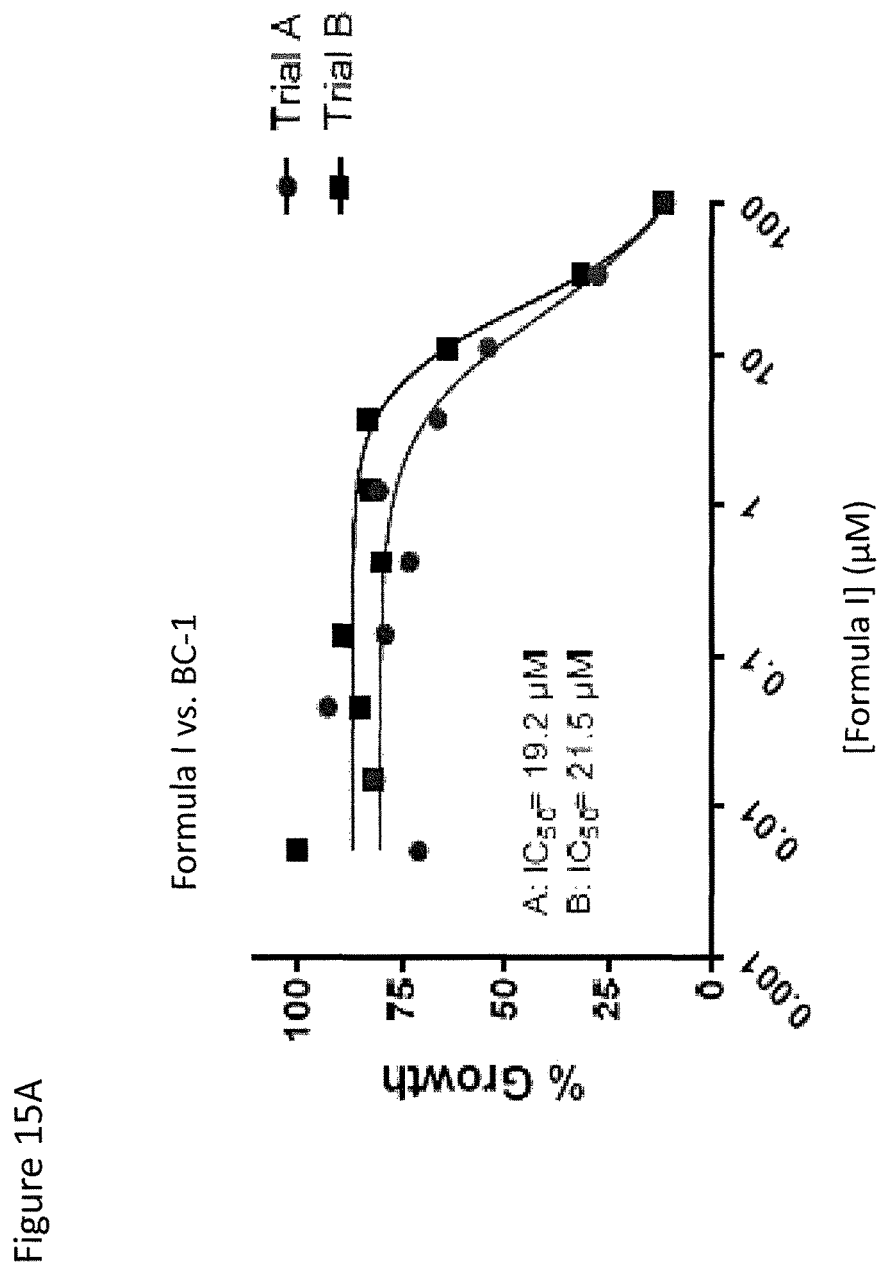
FIG. 15A shows the effect of Formula I on B-cell lymphoma cells as a function of concentration.
Figure 15B:
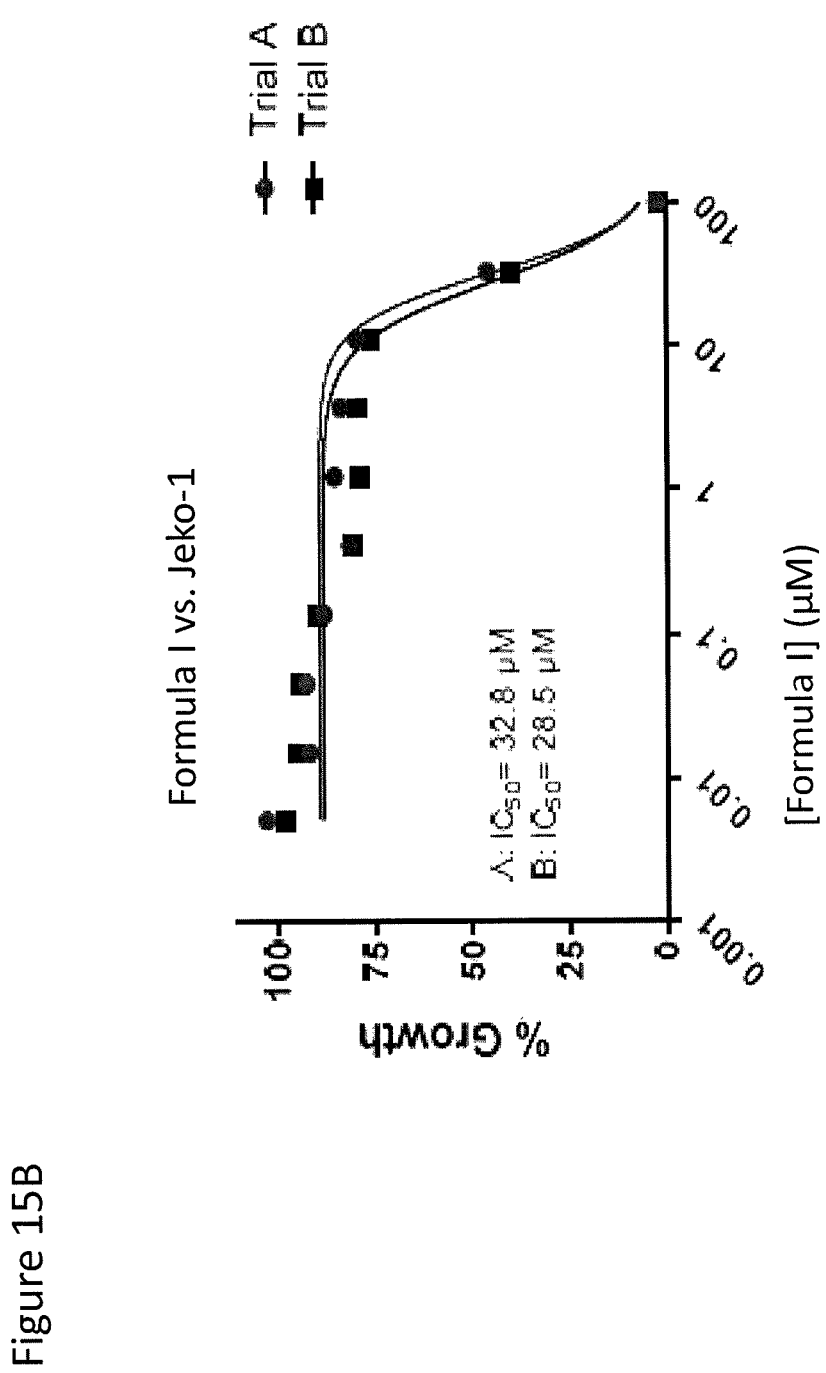
FIG. 15B shows the effect of Formula I on mantle cell lymphoma cells as a function of concentration.
Figure 15C:
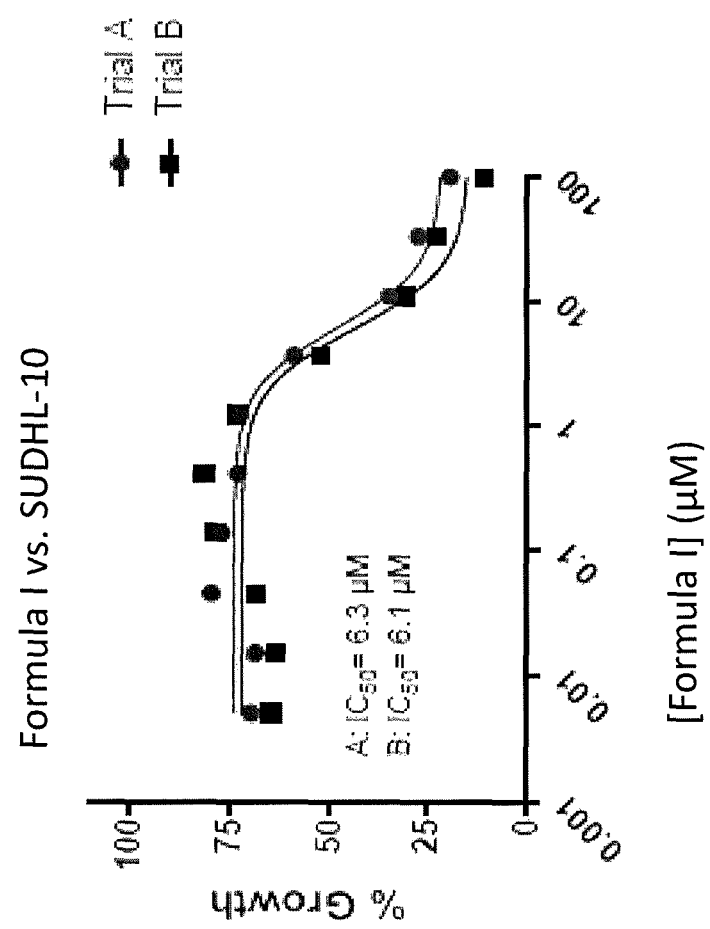
FIG. 15C shows the effect of Formula I on diffuse large B-cell lymphoma cells as a function of concentration.
Figure 15D:
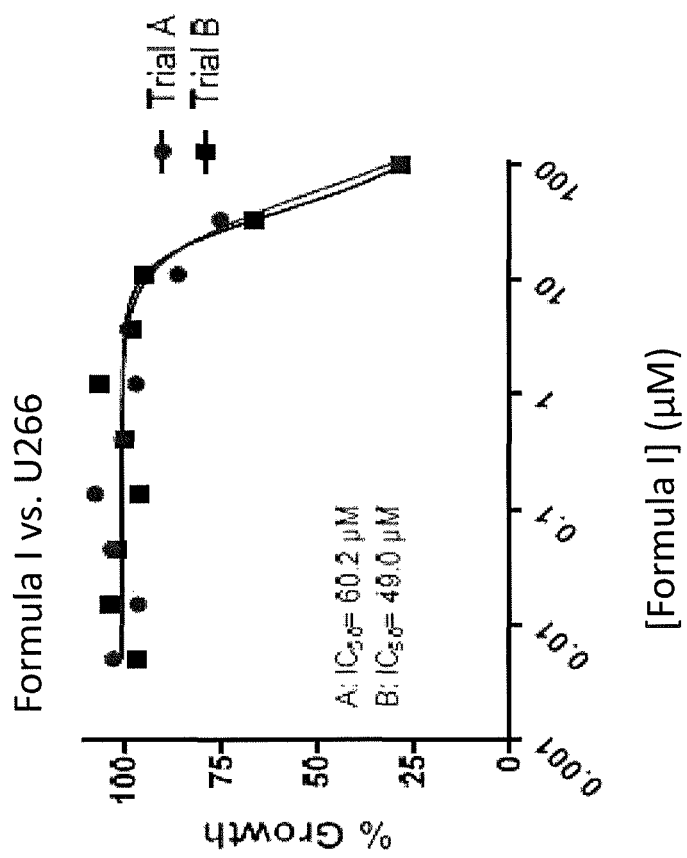
FIG. 15D shows the effect of Formula I on myeloma cells as a function of concentration.

Compounds of Formula I or Formula II and the polymorphs of the present application can be useful in the inhibition of MetAP2. In some embodiments, the compounds of Formula I or Formula II or the polymorphs of the present application can be used as inhibitors of MetAP2. Thus, the compounds of Formula I or Formula II or the polymorphs of the present application (e.g., Form II, Form A) can be used to treat diseases or conditions wherein MetAP2 plays a role (e.g., in the onset, regulation, and/or development of the diseases or conditions), such as cancer (e.g., a hematologic cancer such as lymphoma). For example, FIG. 15 shows the effect of compounds of the present disclosure on cancer cells. FIG. 15A shows the effect of Formula I on B-cell lymphoma cells as a function of concentration. FIG. 15B shows the effect of Formula I on mantle cell lymphoma cells as a function of concentration. FIG. 15C shows the effect of Formula I on diffuse large B-cell lymphoma cells as a function of concentration. FIG. 15D shows the effect of Formula I on myeloma cells as a function of concentration.

Another aspect of the present disclosure relates to a pharmaceutical composition, comprising a compound of Formula I and/or Formula II, and a pharmaceutically acceptable carrier or excipient.

Another aspect of the present disclosure relates to a pharmaceutical composition comprising a polymorph of the present application (e.g., the Form II polymorph of Formula I), and a pharmaceutically acceptable carrier.

In providing a mammal with one or more of the compounds or polymorphs of the present application, the dosage of administered compound(s) or polymorphs will vary depending upon such factors as the mammal's age, weight, height, sex, general medical condition, previous medical history, disease progression, tumor burden, route of administration, formulation and the like. For example, a suitable dose of a compound of the disclosure for a mammal in need of treatment as described herein is in the range of about 0.01 mg to about 2000 mg compound per kilogram of body weight. In addition, in the case of Formula II, due to the effects of being bound to the polymer, the agent may be administered at lower doses than typically used in the treatment of a particular disorder. Surprisingly, in some embodiments the polymer conjugates of the disclosure are more active on a weight/weight basis than the corresponding small molecules.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims. All solvents and other chemical reagents were obtained from commercial sources (e.g., Sigma-Aldrich (St. Louis, Mo.)) and were used without further purification unless noted otherwise.

Abbreviations

Definitions used in the following examples and elsewhere herein are:
EA Ethyl acetate
DAC trans-1,4-Diaminocyclohexane
KF Karl Fischer water content titration
IPC In-process control
BSA Benzenesulfonic acid
$K_2CO_3$ Potassium carbonate
NaCl Sodium chloride
$Na_2SO_4$ Sodium Sulfate
XRPD Analysis Unless otherwise specified, XRPD analysis was carried out on a panalytical X'pert pro, scanning the samples between 3 and 35° 2Θ. The material was gently ground and loaded onto a multi well plate with mylar polymer film to support the sample. the multi well plate was then loaded into the diffractometer running in transmission mode and analyzed, using the following experimental conditions:

Raw Data Origin: XRD measurement (*.XRDML)
Scan Axis: Gonio
Start Position [°2Θ]: 3.0066
End Position [°2Θ]: 34.9866
Step Size [°2Θ]: 0.0130
Scan Step Time [s]: 18.8700
Scan Type: Continuous
PSD Mode: Scanning
PSD Length [°2Θ]: 3.35
Offset [°2Θ]: 0.0000
Divergence Slit Type: Fixed
Divergence Slit Size [° ]: 1.0000
Measurement Temperature [° C.]: 25.00
Anode Material: Cu
K-Alpha1 [Å]: 1.54060
K-Alpha2 [Å]: 1.54443
K-Beta [Å]: 1.39225
K-A2/K-A1 Ratio: 0.50000
Generator Settings: 40 mA, 40 kV
Goniometer Radius [mm]: 240.00
Dist. Focus-Diverg. Slit [mm]: 91.00
Incident Beam Monochromator: No
Spinning: No Thermogravimetric Analysis and Differential Thermal Analysis (TGA/D DTA)

Unless otherwise specified, TG/DTA was carried out by the following procedure. Approximately 3 mg of material was weighed into an open aluminum pan and loaded into a simultaneous thermogravimetric/differential thermal analyzer (TG/DTA) and held at room temperature. The sample was then heated at a rate of 10° C./min from 25° C. to 300° C. during which time the change in sample weight was recorded along with any differential thermal events (DTA). Nitrogen was used as the purge gas at a flow rate of 300 cm$^3$/min.

Differential Scanning Calorimetry (DSC)

Unless otherwise specified, DSC was carried out by the following procedure. Approximately 2 mg of material was weighed into an aluminum DSC pan and sealed nonhermetically with a pierced aluminum lid. The sample pan was then loaded into a Seiko DSC6200 (equipped with a cooler) cooled and held at 20° C. Once a stable heat-flow response was obtained, the sample and reference were heated to 220° C. at a rate of 10° C./min and the resulting heat flow response monitored. The sample was cooled back to 20° C. and re-heated to 220° C. and the resulting heat flow response monitored.

Polarized Light Microscopy (PLM)

Approximately 1 mg of solid was added to a glass microscope slide. The solids were suspended in a single drop of silicon oil and covered with a glass cover slide. The samples were analyzed with polarized and non-polarized light at a magnification of 20×.

Polarimetry

For each sample, a 10 mg/mL solution in methanol was prepared. 100 µL aliquots were taken from each of the solutions and used to prepare 1 mg/mL solutions in methanol. The dilute solutions were used to confirm the results of the tests performed on the 10 mg/mL solutions.

Analysis was performed on a Schmidt and Haensch Polartronic H532 polarimeter. The sample was analyzed in a 100 mm cell. The samples were analyzed using light at a wavelength of 589 nm, and at a temperature of 26° C. The specific rotation was calculated the following equation:

$$\alpha D26 = (\text{Angle measured} * 100) / (\text{Concentration} * \text{Path Length}).$$

Single Crystal X-Ray Analysis (SXRD)

SXRD analysis was conducted on an Agilent Technologies (Dual Source) SuperNova diffractometer using monochromated Mo Kα (λ=0.71073 A) radiation. The diffractometer was fitted with an Oxford Cryosystems low temperature device to enable data collection to be performed at 120(10) K. The data collected were corrected for absorption effects based on gaussian integration over a multifaceted crystal model, implemented as a part of the CrysAlisPro software package (Agilent Technologies, 2014).

The structure was solved by direct methods (SHELXS97)1 and developed by full least squares refinement on F2 (SHELXL97)1 interfaced via the OLEX2 software package. Images produced for this report were done so via a local program.

Data were collected, solved and refined in the trigonal space-group R3. A search for higher symmetry using the ADDSYMM2 routine of PLATON3 failed to uncover any higher symmetry.

All fully-occupied non-hydrogen atoms were located in the Fourier map and their positions refined prior to refining as anisotropic ellipsoids to describe their thermal behavior.

$^1$H Nuclear Magnetic Resonance ($^1$H NMR)

$^1$H NMR spectra were recorded on a Bruker PRO500 (500 MHz) spectrometer or a Bruker AVA500 (500 MHz) spectrometer. Chemical shifts (δ) are quoted in parts per million (ppm) downfield of tetramethylsilane, using residual protonated solvent as internal standard (CDCl$_3$ at 7.26 ppm). Experiments were performed in deuterated chloroform and each sample was prepared at about a 10 mM concentration.

High Performance Liquid Chromatography (HPLC)

Unless otherwise specified, HPLC was carried out using the following experimental conditions:

Column: Agilent Eclipse XDB C18 5 µm, 150×4.6 mm column
Mobile Phase A: 0.1% Trifluoroacetic Acid
Mobile Phase B: 0.1% Trifluoroacetic Acid in Acetonitrile
Diluent 1:1 Water:Acetonitrile
Flow Rate: 1.0 mL/min
Runtime: 24 minutes
Detector: Evaporative Light Scattering Detector (ELSD)
Detector Pressure: 3.6 bar
Detector Gain: 8
Detector Temperature: 50° C.
Detector Gas: Nitrogen
Column Temperature: 25° C.
Autosampler Temperature: 5° C.
Injection Volume: 10 µL (sample volume may be adjusted as required)
Gradient program:

| Time (minutes) | Solvent B (%) |
|---|---|
| 0.0 | 5 |
| 15.0 | 95 |
| 18.0 | 95 |
| 20.0 | 5 |
| 24.0 | 5 |

Example 1—Synthesis and Reactive Crystallization of Fumagill-6-yl N-(trans-4-aminocyclohexyl)carbamate Benzenesulfonic Acid Salt

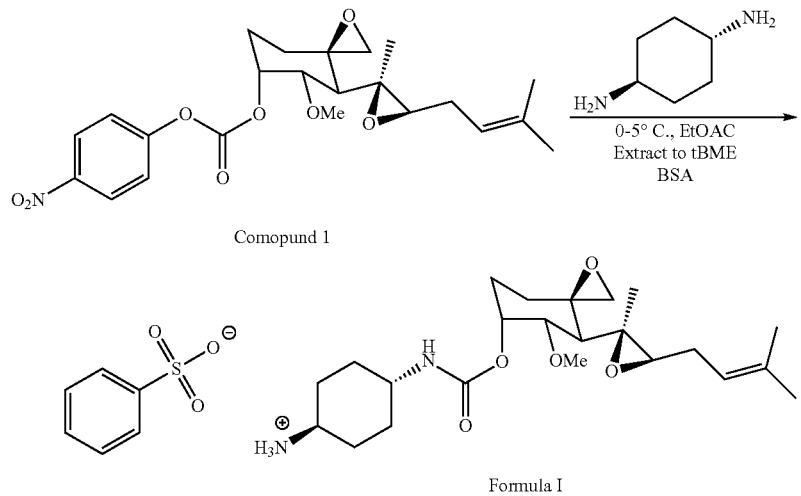

A solution of trans-1,4-diaminocyclohexane (102.2 g, 895 mmol, 4.9 eq) dissolved in ethyl acetate (2.8 L) was cooled to 0-5° C. Fumagill-6-yl p-nitrophenyl carbonate (80.8 g, 181 mmol, 1 eq) was dissolved in ethyl acetate (3.2 L) and added over 30 to 90 minutes to the stirred solution of trans-1,4-diaminocyclohexane while maintaining the temperature at 0-5° C. The reaction mixture was stirred for at least 120 minutes at 0-5° C. until the carbonate was <2% of the starting concentration by an HPLC-UV in-process control. The batch was filtered to remove solid byproducts and the solids rinsed with ethyl acetate (2×1.2 L). The ethyl acetate solution was washed with water (0.5 L) and the aqueous phase discarded. The ethyl acetate was extracted with a solution of water (1.6 L) and 10% citric acid (0.24 L). The pH of the aqueous phase was about 6; the ethyl acetate discarded. The aqueous solution was adjusted to pH 10.3 using 1N sodium carbonate (0.87 L). The product in the form of the free base was extracted into MTBE (4×1.6 L). The organic phases were dried with sodium sulfate (4×128 g) as a drying agent. The organic extracts were combined and filtered to remove the drying agent. The drying agent was washed with MTBE (1.4 L). The fumagill-6-yl N-(trans-4-aminocyclohexyl)carbamate (free base) in MTBE was cooled to 0-5° C. and seeded with fumagill-6-yl N-(trans-4-aminocyclohexyl)carbamate benzenesulfonic acid salt (0.8 g). A solution of benzenesulfonic acid (17.7 g, 0.62 eq) in MTBE (0.43 L) was slowly added while the batch was maintained at 0-5° C. The batch was cooled to −20° C. The solids were collected by filtration, washed with MTBE (0.5 L), and dried at ≤35° C. under vacuum to yield fumagill-6-yl N-(trans-4-aminocyclohexyl)carbamate benzenesulfonic acid salt (68.3 g, 62%, Formula I).

Example 2—Recrystallization of Fumagill-6-yl N-(trans-4-aminocyclohexyl)carbamate Benzenesulfonic Acid Salt A stirred suspension of fumagill-6-yl N-(trans-4-aminocyclohexyl)carbamate benzenesulfonic acid salt (68.3 g, 118 mmole, Formula I) in methanol (200 mL) was warmed to 40° C. until a clear solution was obtained. While maintaining a batch temperature of 40° C., MTBE (250 mL) was slowly added until the solution became cloudy. The batch was cooled to 35° C. over an hour. Seeds of fumagill-6-yl N-(trans-4-aminocyclohexyl)carbamate benzenesulfonic acid salt (684 mg, 1.2 mmole, 1 wt %) were charged. The batch was cooled in 5° C. steps, allowing 30 minutes at each step until the batch reached 2-8° C. and held at 2-8° C. for 10 minutes. Additional MTBE (combined total of 8.8 volumes) was added over 60 minutes, and the batch was held at 2-8° C. for at least 60 minutes. The solids were collected by filtration, washed with MTBE (410 mL), and dried at ≤35° C. under vacuum to yield the desired product (64.6 g, 95%) as the Form II polymorph.

Example 3—Cooling Crystallization of Fumagill-6-yl N-(trans-4-aminocyclohexyl)carbamate Benzenesulfonic Acid Salt fumagill-6-yl N-(trans-4-aminocyclohexyl)carbamate benzenesulfonic acid salt (8.1992 g) was dissolved in 39 mL of MTBE:methanol (50:50) to give a starting concentration of approximately 210 mg/mL. The solution was stirred at 50° C. for 30 minutes and monitored by focused beam reflectance measurement (FBRM) to ensure dissolution. The solution was cooled to 5° C. at a rate of 0.2° C./minute. At 37° C., 0.08 g (ca. 1%) seed material was gently ground using a mortar and pestle and added to the mixture. When the temperature of the solution reached 5° C., a sample was withdrawn and MTBE was added at a rate of 30 mL/hour until 30 mL MTBE had been added. A second sample was withdrawn, and MTBE addition was continued until 60 mL had been added. The crystallization was then stirred for a further 15 minutes. The final slurry was filtered and the resulting material dried in vacuo at 40° C. for about 16 hours.

XRPD spectra for the material produced by the above-described procedure are shown in FIG. 3. FIG. 3A shows an XRPD spectrum of material from the first sample (i.e., before addition of further MTBE), and FIG. 3B shows an XRPD spectrum of material from the second sample (i.e., after addition of 30 mL MTBE). FIG. 3C shows an XRPD spectrum of the final dried material.

Example 4—Antisolvent Crystallization of Fumagill-6-yl N-(trans-4-aminocyclohexyl)carbamate Benzenesulfonic Acid Salt fumagill-6-yl N-(trans-4-aminocyclohexyl)carbamate benzenesulfonic acid salt (8.0514 g) was dissolved in 39 mL of MTBE:methanol (50:50) to give a starting concentration of approximately 210 mg/mL. The solution was stirred at 50° C. for 30 minutes and monitored by focused beam reflectance measurement (FBRM) to ensure dissolution. An aliquot of MTBE was added to the vessel at a rate of 30 mL/hour. After 10.4 mL MTBE had been added, 0.08 g (ca. 1%) seed material was gently ground with a mortar and pestle and added to the mixture. After 30 mL MTBE was added, a sample was withdrawn. Addition of MTBE was continued and a second sample was withdrawn after the addition of 60 mL MTBE. The solution was then cooled to 5° C. at a rate of 0.2° C./minute. The crystallization was then stirred for a further 15 minutes. the final slurry was filtered and the resulting material dried in vacuo at 40° C. for about 16 hours.

XRPD spectra for the material produced by the above-described procedure are shown in FIG. 4. FIG. 4A shows an XRPD spectrum of material from the first sample (i.e., after addition of about 30 mL MTBE), and FIG. 4B shows an XRPD spectrum of material from the second sample (i.e., after addition of 60 mL MTBE). FIG. 4C shows an XRPD spectrum of the final dried material.

Example 5—Synthesis of Fumagill-6-yl N-(trans-4-aminocyclohexyl)carbamate Benzenesulfonic Acid Salt and Crystallization from Ethyl Acetate fumagill-6-yl N-(trans-4-aminocyclohexyl)carbamate benzenesulfonic acid salt was prepared as set forth below. The procedure set forth in Table 17 below demonstrates that it is possible to purify a compound of Formula I directly without having to first acidify the Formula I free base and extract it into the aqueous layer, before basifying the aqueous layer and extracting the free base back into the organic solvent as set forth in Example 1. Without wishing to be bound by theory, this procedure can enable the use of smaller quantities of organic solvent (e.g., methyl tert-butyl ether). This procedure can also be operationally simpler than the process set forth above in Example 1.

TABLE 17

Synthesis of fumagill-6-yl N-(trans-4-aminocyclohexyl)carbamate Benzenesulfonic Acid Salt and Crystallization from Ethyl Acetate

| Step | Operation | Timescale for 50 g batch | In-Process Control (IPC) |
|---|---|---|---|
| 1 | Nitrogen exchange reactor 1 and 2 | 1.3 h | |
| 2 | Add EA and DAC into reactor 2 | 0.2 h | |
| 3 | Warm reactor 2 to ~65-75° C. to dissolve DAC | 1.5 h | |
| 4 | Stir ~0.5-1 h | 0.5 h | |
| 5 | Cool reactor 2 to ~0-5° C. | 1.5 h | |
| 6 | Polish filter contents of reactor 2 into reactor 1, and rinse the filter cake with EA | 0.3 h | |
| 7 | Wash reactor 2 | 0.2 h | |
| 8 | Add fumagill-6-yl, p-nitrophenyl carbonate and EA into reactor 2 | 0.2 h | |
| 9 | Cool reactor 2 to ~0-5° C. | 0.7 h | |
| 10 | Add the mixture of reactor 2 into reactor 1 at ~0-5° C. (including rinsing reactor 2 with EA and adding the EA to reactor 1). | 2.3 h | |
| 11 | In-process control (IPC) at ~0-5° C. 1 h later and sample every ~1-1.5 h | 2 h | No fumagill-6-yl p-nitrophenyl carbonate was detected |
| 12 | Filter reaction mixture and wash filter cake with EA | 0.5 h | |
| 13 | Wash reactor 1 with water, acetone and EA until water content of EA is ≤1.0% as measured by KF. | 1.0 h | 0.05% |
| 14 | Wash the filtrate with brine | 0.5 h | |
| 15 | Wash the filtrate with $K_2CO_3$ and NaCl solution | 0.5 h | |
| 16 | Wash the filtrate with brine | 0.5 h | |
| 17 | Dry the filtrate with $Na_2SO_4$ | 1.0 h | |
| 18 | Filter and wash filter cake with EA. | 0.5 h | KF, 1.15%; assay, 78.19% |
| 19 | Cool filtrate to ~8-12° C. | 0.5 h | |
| 20 | Dissolve BSA in EA and cool the BSA solution to ~8-12° C. | 0.5 h | |
| 21 | Add BSA solution to the filtrate from Step 19 at ~8-12° C. | 1 h | |
| 22 | Stir reaction mixture ~20-40 min after the BSA solution is added. | 0.6 h | |
| 23 | Cool reaction mixture to ~0-5° C. | 0.5 h | |
| 24 | Stir reaction mixture ~1-2 h at ~0-5° C. | 2 h | |
| 25 | Filter reaction mixture | 0.5 h | KF: 0.76%; purity: 98.9% |
| 26 | Triturate and wash the cake with EA once | | KF: 0.13%; purity: 99.28% |

TABLE 17-continued

Synthesis of fumagill-6-yl N-(trans-4-aminocyclohexyl)carbamate
Benzenesulfonic Acid Salt and Crystallization from Ethyl Acetate

| Step | Operation | Timescale for 50 g batch | In-Process Control (IPC) |
|---|---|---|---|
| 27 | Triturate and wash the cake with EA twice | | KF: 0.13%; purity: 99.32% |
| 28 | Dry 10 hand first IPC | 10 h | KF: 0.25%: purity: 99.53% |
| 29 | Dry 24 h and second IPC (final analysis) | 24 h | KF: 0.22% purity: 99.51% EA: 0.16% yield: 77% |

As set forth above in Table 17, the water content in step 18 is kept between 1 and 1.3%. Without wishing to be bound by theory, keeping the water content within this range can help facilitate crystallization of the compound of Formula I directly from ethyl acetate in good purity (e.g., >95%). As set forth in Step 29, the yield was increased using this method by about 10-15% compared with the method of Example 1.

The quantities of materials used in the protocol set forth above are given in Table 18, below:

As set forth in Table 18, benzenesulfonic acid monohydrate (i.e., about 12-13% water and about 1-2% impurities) was used in step 20. Without wising to be bound by theory, using about 0.78-0.8 equivalents of benzenesulfonic acid was found to lead to the highest yields and highest purity of Formula I.

Without wishing to be bound by theory, the ethyl acetate trituration and washes in steps 26 and 27 were performed to reduce water content to an acceptable level prior to drying to minimize the risk of water degradation of Formula I.

TABLE 18

Material Quantities used in Synthesis of fumagill-6-yl N-(trans-4-aminocyclohexyl)carbamate Benzenesulfonic Acid Salt

| Step | Material | FW | Input (g) | Volume (mL) | mmol | eq. | mL solvent per g fumagill-6-yl p-nitrophenyl carbonate | g solvent or reagent per g fumagill-6-yl p-nitrophenyl carbonate |
|---|---|---|---|---|---|---|---|---|
| 2 | EA (KF: 0.09%) | | 1525.0 | 1690 | | | 33.81 | 30.50 |
| 2 | DAC | 114.19 | 63.8 | | 558.7 | 5.0 | | 1.276 |
| 6 | EA | | 50.0 | 55.5 | | | 1.11 | 1.00 |
| 7 | EA | | 2285.5 | 2564 | | | 50.69 | 45.71 |
| 8 | EA | | 1600.0 | 1774 | | | 35.48 | 32.00 |
| 8 | fumagill-6-yl, p-nitrophenyl carbonate | 447.48 | 50.0 | | 111.7 | 1.0 | | 1.00 |
| 10 | EA | | 200.0 | 222 | | | 4.44 | 4.00 |
| 12 | EA | | 450.0 | 499 | | | 9.98 | 9.00 |
| 13 | Purified water | | 2857.0 | 2857.0 | | | 57.14 | 57.14 |
| 13 | Acetone | | 2241.3 | 2857.0 | | | 57.14 | 44.83 |
| 13 | EA | | 1428.5 | 1583.5 | | | 31.67 | 28.57 |
| 14 | Purified water | | 1020.0 | 1020.0 | | | 20.40 | 20.40 |
| 14 | NaCl | | 265.0 | | | | | 5.30 |
| 15 | Purified water | | 980.0 | 980.0 | | | 19.60 | 19.60 |
| 15 | NaCl | | 176.0 | | | | | 3.52 |
| 15 | $K_2CO_3$ | | 25.5 | | | | | 0.51 |
| 16 | Purified water | | 735.0 | 735.0 | | | | 14.70 |
| 16 | NaCl | | 265.0 | | | | | 5.30 |
| 17 | $Na_2SO_4$ | | 400.0 | | | | | 8.00 |
| 18 | EA | | 450.0 | 499.0 | | | 9.98 | 9.00 |
| 20 | BSA monohydrate (assay: 85.86%) | 158.2 | 16.06 | | | 0.78 | | |
| 20 | EA | | 78.5 | 86.5 | | | 1.73 | 1.57 |
| 26 | EA | | 451.5 | 500 | | | 10.00 | 9.03 |
| 27 | EA | | 451.5 | 500 | | | 10.00 | 9.03 |

Example 6—In Process Controls for Synthesis of Fumagill-6-yl N-(trans-4-aminocyclohexyl)carbamate Benzenesulfonic Acid Salt The HPLC conditions used for this Example are set forth below:

| | |
|---|---|
| Column | ZORBAX Eclipse XDB C18, 4.6 × 150 mm, 5 μm |
| Flow rate | 1.0 mL/min |
| Column temperature | 25 C. |
| Detector | CAD Gain = 100 Pa, Filter-1 s, Temp-Low (35° C.) |
| Injector | 10 μL |
| Mobile phase A | 0.1% TFA in Water |
| Mobile phase B | 0.1% TFA in Acetonitrile |

| T/min | 0.0 | 8.0 | 15.0 | 25.0 | 29.0 | 30.0 | 35.0 |
|---|---|---|---|---|---|---|---|
| Gradient % B | 5 | 20 | 40 | 95 | 95 | 5 | 5 |

| Needle wash | Acetonitrile |
|---|---|

Table 19 below shows the results of in-process controls as measured by high-pressure liquid chromatography (HPLC) for various batches of fumagill-6-yl N-(trans-4-aminocyclohexyl)carbamate benzenesulfonic acid salt (Formula I). Formula I had a retention time of 16.18 min and a relative retention time of 1. Various impurities, including Compound 2 and Compound 4 are defined by their retention times in Table 19.

As set forth in Table 19, Lots 1-3 are control standards. Lot 1 was produced by the method of Example 1. Lot 2 and Lot 3 are comparison batches, wherein Lot 3 was recrystallized using methanol and methyl tert-butyl ether.

Lots 4-10 are in-process controls measured during the process set forth in Example 5, above. Lot 4 gives HPLC data taken after 1 hour of step 11 of Table 17. Lot 5 gives HPLC data after drying with $Na_2SO_4$ in step 17. Lot 6 gives HPLC data after filtering in step 25. Lot 7 gives HPLC data after washing Formula I once with ethyl acetate. Lot 8 gives HPLC data after washing Formula I twice with ethyl acetate. Lot 9 gives HPLC data after filtering Formula I and drying for 10 hours. Lot 10 gives HPLC data after filtering Formula I and drying for 24 hours. As set forth in the analysis of Lot 10, the purity of Formula I after 24 hours of drying was the same as Lot 1, produced by the method of Example 1 without recrystallizing from methanol/methyl tert-butyl ether.

TABLE 19

In-Process Controls Measured by HPLC for Different Synthesis Methods

| | | Cmpd. 4 Retention Time | | | | | | | F.I. |
|---|---|---|---|---|---|---|---|---|---|
| | | 12.62 | 12.82 | 13.11 | 13.32 | 14.50 | 15.38 | 15.53 | 16.18 |
| | | Relative Retention Time | | | | | | | |
| Lot# | Note | 0.78 | 0.79 | 0.81 | 0.82 | 0.94 | 0.95 | 0.96 | 1.00 |
| 1 | | | <0.05 | | | | | | 99.44 |
| 2 | | <0.05 | <0.05 | | <0.05 | | 0.10 | 0.11 | 97.15 |
| 3 | | | <0.05 | | | | <0.05 | | 99.41 |
| 4 | IPC 1 h | | <0.05 | | <0.05 | | <0.05 | | 93.76 |
| 5 | KF: 1.15% Filtrate after dried by $Na_2SO_4$ | | | | <0.05 | | | | 93.52 |
| 6 | KF: 0.76% (before drying) | <0.05 | <0.05 | <0.05 | 0.05 | <0.05 | <0.05 | | 99.31 |
| 7 | KF: 0.13% (EA wash one time) | <0.05 | <0.05 | <0.05 | <0.05 | <0.05 | <0.05 | | 99.57 |
| 8 | KF: 0.13% (EA wash twice time) | <0.05 | <0.05 | <0.05 | <0.05 | <0.05 | <0.05 | | 99.63 |
| 9 | Drying 10 h | <0.05 | <0.05 | <0.05 | <0.05 | <0.05 | 0.05 | | 99.53 |
| 10 | Drying 24 h | <0.05 | <0.05 | <0.05 | <0.05 | <0.05 | 0.06 | | 99.51 |

| | | F.I. | | | | | Cmpd. 2 Retention Time | | | | Cmpd. 6 |
|---|---|---|---|---|---|---|---|---|---|---|---|
| | | 16.18 | 17.19 | 17.96 | 18.12 | 18.25 | 18.46 | 18.72 | 22.39 | 23.30 | 24.68 |
| | | Relative Retention Time | | | | | | | | | |
| Lot # | Note | 1.00 | 1.06 | 1.11 | 1.12 | 1.13 | 1.14 | 1.15 | 1.38 | 1.44 | 1.53 |
| 1 | | 99.44 | | <0.05 | 0.22 | 0.24 | | | | | |
| 2 | | 97.15 | <0.05 | 0.32 | 1.48 | | | 0.28 | | | 0.30 |
| 3 | | 99.41 | <0.05 | <0.05 | 0.34 | <0.05 | | <0.05 | | | <0.05 |
| 4 | IPC 1 h | 93.76 | 0.15 | | 0.09 | | | 0.13 | <0.05 | | 5.77 |

TABLE 19-continued

In-Process Controls Measured by HPLC for Different Synthesis Methods

| | | | | | | | | |
|---|---|---|---|---|---|---|---|---|
| 5 | KF: 1.15% Filtrate after dried by $Na_2SO_4$ | 93.52 | 0.15 | <0.05 | <0.05 | 0.10 | <0.05 | 6.48 |
| 6 | KF: 0.76% (before drying) | 99.31 | <0.05 | | 0.11 | 0.05 | <0.05 | 0.48 |
| 7 | KF: 0.13% (EA wash one time) | 99.57 | <0.05 | | 0.11 | 0.05 | <0.05 | 0.27 |
| 8 | KF: 0.13% (EA wash twice time) | 99.63 | <0.05 | | 0.11 | <0.05 | <0.05 | 0.27 |
| 9 | Drying 10 h | 99.53 | | | 0.11 | 0.06 | | 0.25 |
| 10 | Drying 24 h | 99.51 | <0.05 | | 0.11 | 0.06 | <0.05 | 0.25 |

Example 7—Formula I Inhibits Hematological Tumor Cell Lines

The half-maximal inhibitory concentration(s) ($IC_{50}$) of Formula I as a single agent against a panel of human hematological tumor cell lines was investigated. All cell lines were grown in their respective proper growth media supplemented with 5-10% FBS and housed in an atmosphere of 5% $CO_2$ at 37° C.

TABLE 20

Single Agent Cell Viability Assay Parameters

| | |
|---|---|
| Test Agent Conditions | 100 µM high: 10 concentrations, 1:3 dilutions |
| Assay Exposure Time | 72 Hours continuous |
| Method | CellTiter-Glo Cell viability Assay |
| Replicates | 3 replicates per concentration; 2 technical replicates |

TABLE 21

Single Agent Cell Viability Assay Screen

| Cell Line | Tissue Type | Mean $IC_{50}$ (µM) Formula I | Mean $IC_{50}$ (µM) Adriamycin | Mean $IC_{50}$ (µM) Bortezomib |
|---|---|---|---|---|
| BC-1 | B-Cell Lymphoma | 20.35 | 0.02 | — |
| Jeko-1 | Mantle Cell Lymphoma | 30.65 | — | 0.40 |
| SU-DHL-10 | Diffuse Large B-Cell Lymphoma | 6.20 | 0.00085 | — |
| U266 | Myeloma | 54.60 | — | 0.0024 |

Single Agent Studies

Cell Viability Assay—72 Hours Continuous Exposure Time 1. 0 hr: Cells were plated in growth media in 96-well microtiter plates at a 200 µL volume. Cells were incubated for 24 hours at 37° C. in a humidified incubator.

2. 24 hr: The test agent's drug doses were achieved using HP D300 Digital Dispenser. Briefly, the digital dispenser added test agent in a DMSO solvent at precise volumes to media containing wells. Control wells received equivolumes of DMSO that test agents wells received. Following drugging, cells were exposed at the concentrations and dilutions described in Table 20 for 72 hours at 37° C. in a humidified incubator.

3. 72 hr: Following 72 hour exposure, 100 µl of a 1:1 mixture of sterile water and CellTiter-Glo® Reagent was added to each well. The plates are incubated for 60 minutes at room temperature. After incubation, luminescence was recorded using a luminometer. The results are shown below in Table 21 and in FIGS. 15A, 15B, 15C and 15D.

Endpoint $IC_{50}$ Determination:

Data is expressed as the percent cell growth of the untreated (vehicle) control calculated from the luminescence signals. The surviving fraction of cells was determined by dividing the mean luminescence values of the test agents by the mean luminescence values of untreated control. The inhibitory concentration value for the test agent(s) and control was estimated using Prism 6 software (GraphPad Software, Inc.) by curve-fitting the data using the non-linear regression analysis.

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A polymorphic form of fumagill-6-yl N-(trans-4-aminocyclohexyl)carbamate 1-hydroxy-2-naphthoic acid salt characterized by an X-ray powder diffraction pattern comprising peaks at 5.6, 8.9, 11.5, 12.1, 15.4, and 20.9 degrees 2θ using Cu Kα radiation.

2. The polymorphic form of claim 1, characterized by an X-ray powder diffraction pattern comprising peaks at 5.6, 8.9, 11.5, 12.1, 15.4, 15.9, 19.7, 20.9, and 23.3 degrees 2θ using Cu Kα radiation.

3. The polymorphic form of claim 1, characterized by an X-ray powder diffraction pattern comprising peaks at 5.6, 8.9, 11.5, 12.1, 14.6, 15.4, 15.9, 17.4, 18.1, 19.7, 20.9, and 23.3 degrees 2θ using Cu Kα radiation.

4. The polymorphic form of claim 1, characterized as having an X-ray diffraction pattern as set forth in FIG. 10A, 10B, 10C, or 10D.

5. The polymorphic form of claim 1, characterized by an endothermic onset at 181° C. and peak at 186° C. and an exotherm at 191° C. as measured by thermogravimetric analysis/differential thermal analysis.

6. The polymorphic form of claim 1, characterized by an endothermic onset at 182° C. and a peak at 186° C. as measured by differential scanning calorimetry.

7. A method of treating a disease selected from lymphoma and myeloma in a subject in need thereof, comprising administering to the subject in need thereof an effective amount of a polymorphic form of claim 1.

8. The method of claim 7 wherein the cancer is lymphoma.

9. The method of claim 7 wherein the cancer is myeloma.

10. A method of inhibiting MetAP2 in a subject in need thereof, comprising administering to the subject in need thereof an effective amount of a polymorphic form of claim 1.

11. A method of preparing the polymorphic form of claim 1, comprising crystallizing fumagill-6-yl N-(trans-4-aminocyclohexyl)carbamate 1-hydroxy-2-naphthoic acid salt from acetonitrile, ethyl acetate, methyl ethyl ketone, or tetrahydrofuran.

* * * * *